(12) United States Patent
Lee et al.

(10) Patent No.: US 9,006,187 B2
(45) Date of Patent: Apr. 14, 2015

(54) THIOPHENE DERIVATIVE AS SGLT2 INHIBITOR AND PHARMACEUTICAL COMPOSITION COMPRISING SAME

(75) Inventors: Jinhwa Lee, Yongin-si (KR); Kwang-Seop Song, Yongin-si (KR); Suk Ho Lee, Yongin-si (KR)

(73) Assignee: Green Cross Corporation, Yongin-Si (KR)

( * ) Notice: Subject to any disclaimer, the term of this patent is extended or adjusted under 35 U.S.C. 154(b) by 0 days.

(21) Appl. No.: 13/821,863

(22) PCT Filed: Sep. 9, 2011

(86) PCT No.: PCT/KR2011/006744
§ 371 (c)(1),
(2), (4) Date: Mar. 8, 2013

(87) PCT Pub. No.: WO2012/033390
PCT Pub. Date: Mar. 15, 2012

(65) Prior Publication Data
US 2013/0172278 A1    Jul. 4, 2013

Related U.S. Application Data

(60) Provisional application No. 61/381,613, filed on Sep. 10, 2010.

(51) Int. Cl.
| | |
|---|---|
| *C07H 7/06* | (2006.01) |
| *C07D 409/04* | (2006.01) |
| *C07H 17/00* | (2006.01) |
| *C07D 409/14* | (2006.01) |

(52) U.S. Cl.
CPC ............. *C07H 17/00* (2013.01); *C07D 409/04* (2013.01); *C07D 409/14* (2013.01)

(58) Field of Classification Search
CPC ................................ C07H 7/06; C07D 409/04
USPC .............................................. 514/23; 536/122
See application file for complete search history.

(56) References Cited

U.S. PATENT DOCUMENTS

| 7,202,350 B2 * | 4/2007 | Imamura et al. ............. 536/1.11 |
| 2005/0233988 A1 * | 10/2005 | Nomura et al. ................. 514/43 |
| 2006/0122126 A1 | 6/2006 | Imamura et al. |

OTHER PUBLICATIONS

Adachi et al., Metabolism, 49(8), Aug. 2000, 990-995.*
Wolff, Manfred E., "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, p. 596.*

* cited by examiner

*Primary Examiner* — Traviss C McIntosh, III
(74) *Attorney, Agent, or Firm* — Sughrue Mion, PLLC

(57) ABSTRACT

The present invention relates to a novel compound with thiophene ring having an inhibitory activity against sodium-dependent glucose cotransporter 2 (SGLT2) being present in the intestine and kidney, and a pharmaceutical composition comprising the same as an active ingredient, which is useful for preventing or treating metabolic disorders, particularly diabetes. The prevention also provides a method for preparing same, a pharmaceutical composition containing same, and a method for preventing or treating metabolic disorders, particularly diabetes.

16 Claims, 1 Drawing Sheet

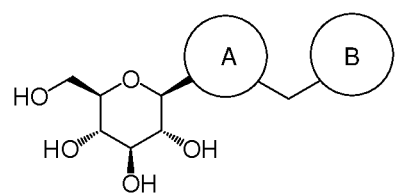

THIOPHENE DERIVATIVE AS SGLT2 INHIBITOR AND PHARMACEUTICAL COMPOSITION COMPRISING SAME

FIELD OF THE INVENTION

The present invention relates to a novel compound with thiophene ring having an inhibitory activity against sodium-dependent glucose cotransporter 2 (SGLT2) being present in the intestine and kidney, and a pharmaceutical composition comprising the same as an active ingredient, which is useful for preventing or treating diabetes.

BACKGROUND OF THE INVENTION

The prevalence of diabetes has become an increasing concern to the world's population. An estimated 285 million people, corresponding to 6.4% of the world's adult population, will live with diabetes in 2010. The number is expected to grow to 438 million by 2030, corresponding to 7.8% of the adult population. Diabetes is characterized by a chronic metabolic disorder that is caused by failure of the body to produce insulin and/or an inability of the body to respond adequately to circulating insulin. Secreted by the pancreas, insulin increases the ability of tissue to absorb blood glucose. Accordingly, disruption of insulin function results in the high level of blood glucose that is commonly associated with diabetic patients. There are two generally recognized form of diabetes: Type 1 diabetes, or insulin-dependent diabetes mellitus (IDDM), is characterized as an autoimmune disease involving pancreatic β-cells, while type 2 diabetes, or noninsulin-dependent diabetes mellitus (NIDDM), is characterized by β-cell dysfunction and insulin resistance. Type 2 diabetes is the most prevalent abnormality of glucose homeostasis, accounting for approximately 90 to 95% of all cases of diabetes. The diabetes has been widespread throughout the whole world due to ageing populations and rapid cultural changes such as increasing urbanization, dietary change, decreased physical activity and other unhealthy behavioral patterns.

The burden of diabetes is driven by vascular complications such as cardiovascular disease, stroke, nephropathy, retinopathy, renal failure, and lower limb infection and gangrene. Although these complications result from multiple metabolic disorders, hyperglycemia is considered as the main cause of both the vascular consequences of the disease and the progressive nature of diabetes itself. Most harmful of all is that high glucose levels aggravate insulin resistance, impair β-cell function and finally contribute to β-cell apoptosis. The loss of β-cell function deteriorates hyperglycemia, resulting in a vicious cycle that culminates in the abject destruction of the β-cells. The United Kingdom Prevention of Diabetes Study (UKPDS) showed that incremental reductions in glycosylated hemoglobin (HbA1C) lowered the risk of diabetes-related events [Stratton, I. M. et al. Br. Med. J., 2000, 321, 405-412]. Thus, it is recommended that patients with type 2 diabetes should reduce HbA1C values to 7% and less.

The most important strategy for treatment of type 2 diabetes involves lifestyle interventions that promote body weight loss, leading to an improvement in glycemic control. In case lifestyle interventions are not enough for the management of diabetes, an extensive range of antidiabetic drugs might be considered for the treatment of the condition (monotherapies and combination therapies). These therapies target the liver to reduce glucose output, small intestine to decrease glucose absorption, adipose deposits or muscle to elevate glucose cellular uptake or to promote glucose metabolism, serum proteases to prolong incretin action, and the pancreas to enhance insulin release. Despite the wide range of antihyperglycemic agent, it is difficult for many patients to achieve HbA1C target level. In a study reviewing diabetic patients for control of vascular risk factors, only 37.0% of participants achieved the target goal of HbA1C level of less than 7.0% [Saydah, S. H. et al. J. Am. Med. Assoc., 2004, 291, 335-342]. In addition, current therapies have limited durability and/or are associated with significant side effects such as gastrointestinal intolerance, hypoglycemia, weight gain, lactic acidosis and edema. Thus, significant unmet medical needs still remain for the treatment of diabetes. In particular, safer, better tolerated medications which provide increased efficacy and long-term durability are desired.

The obvious need for new approaches to treat patients with uncontrolled type 2 diabetes has promoted continuous exploration of alternative targets in organs involved in maintenance of glucose homeostasis. In the context of type 2 diabetes, renal glucose reabsorption contributes to plasma glucose levels and the concomitant microvascular complications. Evaluation of molecular targets available in the kidney (a major unexploited contributor to glucose homeostasis) stimulated interest in the development of a new class of antihyperglycemic agents that promote urinary glucose excretion. Inhibitors of the SGLT2 prevent renal glucose reabsorption from the glomerular filtrate and provide an insulin-independent way of controlling hyperglycemia.

Sodium-dependent glucose cotransporters (SGLTs) couple the transport of glucose against a concentration gradient with the simultaneous transport of $Na^+$ down a concentration gradient. Two important SGLT isoforms have been cloned and identified as SGLT1 and SGLT2. SGLT1 is located in the gut, kidney, and heart where its expression regulates cardiac glucose transport. SGLT1 is a high-affinity, low-capacity transporter and therefore accounts for only a small fraction of renal glucose reabsorption. In contrast, SGLT2 is a low-affinity, high-capacity transporter located exclusively at the apical domain of the epithelial cells in the early proximal convoluted tubule. In healthy individuals, greater than 99% of the plasma glucose that filtered in the kidney glomerulus is reabsorbed, resulting in less than 1% of the total filtered glucose being excreted in urine. It is estimated that 90% of renal glucose reabsorption is facilitated by SGLT2; the remaining 10% is likely mediated by SGLT1 in the late proximal straight tubule. Genetic mutations in SGLT2 lead to increased renal glucose excretion of as much as 140 g/day depending on the mutation with no apparent adverse effects on carbohydrate metabolism. Since SGLT2 appears to be responsible for the majority of renal glucose reabsorption based on human mutation studies, it has become target of therapeutic interest [Lee, J. et al. Bioorg. Med. Chem. 2010, 18, 2178-2194; van den Heuvel, L. P. et al. Hum. Genet. 2020, 111, 544-547].

Phlorizin was isolated from the root bark of the apple tree and evaluated as the first SGLT inhibitor. Despite antidiabetic potency of phlorizin, its metabolic instability due to β-glucosidase cleavage in the intestinal tract has prevented its development as a drug for the treatment of diabetes. Subsequently, T-1095, by Tanabe Seiyaku, was reported as the first orally absorbable SGLT2 inhibitor, overcoming the disadvantage of phlorizin. T-1095 was absorbed in the intestine and converted to an active form, T-1095A. Following the discovery of T-1095, O-aryl glucosides such as sergliflozin and remogliflozin advanced furthest in clinical trials. Again, concern regarding gut β-glucosidase-mediated degradation, resulted in developing sergliflozin A and remogliflozin A being administered as the ethyl carbonate prodrugs, sergliflozin and remogliflozin, respectively. Subsequent endeavors to identify SGLT2 inhibitors suitable for oral administration without the need for a prodrug led to the discovery of C-aryl glucoside-derived SGLT2 inhibitors. C-aryl glucoside appears to have drug-like properties with enhanced chemical stability of the glucosidic bond. Extensive SAR studies by Bristol-Myers Squibb identified dapagliflozin, a potent, selective SGLT2 inhibitor for the treatment of type 2 diabetes. At present, dapagliflozin is the most advanced SGLT2 inhibitor in clinical trials and is believed to be the first SGLT2 inhibitor to go to market [Meng, W. et al. *J. Med. Chem.* 2008, 51, 1145-1149]. On the other hand, Mitsubishi Tanabe Pharma, in collaboration with Johnson & Johnson, is developing canagliflozin, another novel C-aryl glucoside-derived SGLT2 inhibitor [Tanabe Seiyaku, WO 2008/013321].

Considering the important impact of diabetes on public health and unmet medical needs of current therapy, it is no surprise that SGLT2 inhibitors are currently interesting topics of studies, which were published in the following review articles [Washburn, W. N. *Expert Opin. Ther. Patents,* 2009, 19, 1485-1499; Washburn, W. N. *J. Med. Chem.* 2009, 52, 1785-1794].

SUMMARY OF THE INVENTION

It is a primary object of the present invention to provide a novel compound, a pharmaceutically acceptable salt thereof, or a prodrug thereof, which is effective as SGLT2 inhibitor, useful for the prevention and treatment of metabolic disorders, particularly diabetes.

It is another object of the present invention to provide a method for preparing the inventive compound.

It is another object of the present invention to provide a pharmaceutical composition comprising the inventive compound for preventing or treating metabolic disorders, particularly diabetes.

According to one aspect of the present invention, there is provided a compound of formula (I), or a pharmaceutically acceptable salt or a prodrug thereof:

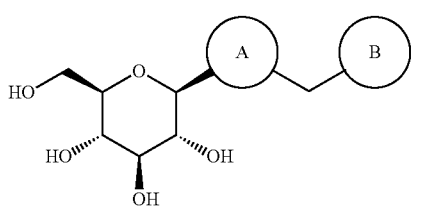

(I)

wherein, ring A and ring B have the meanings as defined in the following description.

According to another aspect of the present invention, there is provided a method for preparing the compound of formula (I).

According to a further aspect of the present invention, there is provided a pharmaceutical composition for treating or preventing metabolic disorders, comprising the compound of formula (I), or a pharmaceutically acceptable salt or a prodrug thereof, as an active ingredient, and a pharmaceutically acceptable carrier.

The inventive thiazole derivative of formula (I) or a pharmaceutically acceptable salt or a prodrug thereof is effective as an inhibitor against sodium-dependent glucose cotransporter (SGLT2), thereby preventing or treating diabetes.

BRIEF DESCRIPTION OF THE DRAWINGS

The above and other objects and features of the present invention will become apparent from the following description of the invention, when taken in conjunction with the accompanying drawing FIG. 1, which represents the compound of formula (I) according to the present invention.

DETAILED DESCRIPTION OF THE INVENTION

As used herein, the term "halogen" refers to fluorine (F), chlorine (Cl), bromine (Br), or iodine (I).

As used herein, the term "alkyl" refers to a straight or branched chain saturated hydrocarbon radical. Examples of "alkyl" as used herein include, but are not limited to, methyl, ethyl, n-propyl, isopropyl, n-butyl, isobutyl, t-butyl, n-pentyl, isopentyl, and hexyl. The "alkyl" is optionally substituted by one or more substituents selected from the group consisting of $C_{1-3}$ alkyl optionally having one to three fluorine substituents, $C_{2-3}$ alkenyl, $C_{2-3}$ alkynyl, $C_{1-2}$ alkoxy optionally having one to three fluorine substituents, sulfanyl, sulfinyl, sulfonyl, oxo, hydroxy, mercapto, amino, guanidino, carboxy, aminocarbonyl, aryl, aryloxy, heteroaryl, heteroaryloxy, heterocycloalkyl, aminosulfonyl, sulfonylamino, carboxyamide, ureido, nitro, cyano, and halogen.

As used herein, the term "alkenyl" refers to a straight or branched chain hydrocarbon radical having at least one carbon-carbon double bond. Examples of "alkenyl" as used herein include, but are not limited to, ethenyl and propenyl. The "alkenyl" has optional substituents selected from the group consisting of $C_{1-3}$ alkyl optionally having one to three fluorine substituents, amino, aryl, cyano, and halogen.

As used herein, the term "alkynyl" refers to a straight or branched chain hydrocarbon radical having at least one carbon-carbon triple bond. Examples of "alkynyl" as used herein include, but are not limited to, acetylenyl and 1-propynyl. The "alkynyl" optionally has one or more substituents selected from the group consisting of $C_{1-3}$ alkyl optionally having one to three fluorine substituents, amino, aryl, and halogen.

As used herein, the term "cycloalkyl" refers to a monocyclic or fused bicyclic hydrocarbon radical having non-aromaticity. The "cycloalkyl" may consist of three to ten carbon atoms. Exemplary "cycloalkyl" groups include, but are not limited to, cyclopropyl, cyclobutyl, cyclopentyl, cyclopentenyl, cyclohexyl, and cycloheptyl.

As used herein, the term "cycloalkenyl" refers to a monocyclic or fused bicyclic hydrocarbon radical having non-aromaticity. The "cycloalkenyl" contains at least one double bond in the ring structure and may consist of three to ten carbon atoms. Exemplary "cycloalkenyl" groups include, but are not limited to, cyclopropenyl, cyclobutenyl, cyclopentenyl, cyclopentenyl, cyclohexenyl, and cycloheptenyl.

The "cycloalkyl" or "cycloalkenyl" group is optionally substituted with one or more substituents selected from the group consisting of $C_{1-3}$ alkyl optionally having one to three fluorine substituents, $C_{2-3}$ alkenyl, $C_{2-3}$ alkynyl, $C_{1-2}$ alkoxy optionally having one to three fluorine substituents, sulfanyl, sulfinyl, sulfonyl, oxo, hydroxy, mercapto, amino, guanidino, carboxy, aminocarbonyl, aryl, aryloxy, heteroaryl, heterocycloalkyl, aminosulfonyl, sulfonylamino, carboxyamide, nitro, ureido, cyano, and halogen.

As used herein, the term "aryl" refers to an optionally substituted benzene ring or refers to a ring system which may result by fusing one or more optional substituents. Exemplary optional substituents include substituted $C_{1-3}$ alkyl, substituted $C_{2-3}$ alkenyl, substituted $C_{2-3}$ alkynyl, heteroaryl, heterocycloalkyl, aryl, alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, and ureido. Such a ring or ring system may be optionally fused to aryl rings (including benzene rings) optionally having one or more substituents, cycloalkyl rings or heterocycloalkyl rings. Examples of "aryl" groups include, but are not limited to, phenyl, naphthyl, tetrahydronaphthyl, biphenyl, indanyl, anthracyl, and phenanthryl, as well as substituted derivatives thereof.

As used herein, the term "heteroaryl" refers to an optionally substituted monocyclic five to six-membered aromatic ring containing one or more heteroatomic substitutions selected from S, SO, $SO_2$, O, N, and N-oxide, or refers to such an aromatic ring fused to one or more rings such as heteroaryl rings, aryl rings, heterocycloalkyl rings, or cycloalkyl rings (e.g., a bicyclic or tricyclic ring system), each having optional substituents. Examples of optional substituents are selected from the group consisting of substituted $C_{1-3}$ alkyl, substituted $C_{2-3}$ alkenyl, substituted $C_{2-3}$ alkynyl, heteroaryl, heterocycloalkyl, aryl, $C_{1-3}$ alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen or ureido. Examples of "heteroaryl" groups used herein include, but are not limited to, benzoimidazolyl, benzothiazolyl, benzoisothiazolyl, benzothiophenyl, benzopyrazinyl, benzotriazolyl, benzo[1,4]dioxanyl, benzofuranyl, 9H-a-carbolinyl, cinnolinyl, furanyl, furo[2,3-b]pyridinyl, imidazolyl, imidazolidinyl, imidazopyridinyl, isoxazolyl, isothiazolyl, isoquinolinyl, indolyl, indazolyl, indolizinyl, naphthyridinyl, oxazolyl, oxothiadiazolyl, oxadiazolyl, phthalazinyl, pyridyl, pyrrolyl, purinyl, pteridinyl, phenazinyl, pyrazolyl, pyridyl, pyrazolopyrimidinyl, pyrrolizinyl, pyridazyl, pyrazinyl, pyrimidyl, 4-oxo-1,2-dihydro-4H-pyrrolo[3,2,1-ij]-quinolin-4-yl, quinoxalinyl, quinazolinyl, quinolinyl, quinolizinyl, thiophenyl, triazolyl, triazinyl, tetrazolopyrimidinyl, triazolopyrimidinyl, tetrazolyl, thiazolyl, thiazolidinyl, and substituted versions thereof.

As used herein, the term "heterocycloalkyl" refers to a three to seven-membered ring containing one or more heteroatomic moieties selected from S, SO, $SO_2$, O, N, and N-oxide, optionally substituted with one or more substituents selected from the group which includes substituted $C_{1-3}$ alkyl, substituted $C_{2-3}$ alkenyl, substituted $C_{2-3}$ alkynyl, heteroaryl, heterocycloalkyl, aryl, $C_{1-3}$ alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, and ureido. Such a ring can be saturated or have one or more degrees of unsaturation. Such a ring may be optionally fused to one or more "heterocycloalkyl" ring(s), aryl ring(s), heteroaryl ring(s) or cycloalkyl ring(s), each having optional substituents. Examples of "heterocycloalkyl" moieties include, but are not limited to, 1,4-dioxanyl, 1,3-dioxanyl, pyrrolidinyl, pyrrolidin-2-onyl, piperidinyl, imidazolidine-2,4-dionepiperidinyl, piperazinyl, piperazine-2,5-dionyl, morpholinyl, dihydropyranyl, dihydrocinnolinyl, 2,3-dihydrobenzo[1,4]dioxinyl, 3,4-dihydro-2H-benzo[b][1,4]-dioxepinyl, tetrahydropyranyl, 2,3-dihydrofuranyl, 2,3-dihydrobenzofuranyl, dihydroisoxazolyl, tetrahydrobenzodiazepinyl, tetrahydroquinolinyl, tetrahydrofuranyl, tetrahydronaphthyridinyl, tetrahydropurinyl, tetrahydrothiopyranyl, tetrahydrothiophenyl, tetrahydroquinoxalinyl, tetrahydropyridinyl, tetrahydrocarbolinyl, 4H-benzo[1,3]-dioxinyl, benzo[1,3]dioxonyl, 2,2-difluorobenzo-[1,3]-dioxonyl, 2,3-dihydro-phthalazine-1,4-dionyl, and isoindole-1,3-dionyl.

As used herein, the term "alkoxy" refers to the group —$OR_a$, where $R_a$ is alkyl as defined above. Exemplary "alkoxy" groups useful in the present invention include, but are not limited to, methoxy, difluoromethoxy, trifluoromethoxy, ethoxy, n-propoxy, isopropoxy, n-butoxy and t-butoxy.

As used herein, the term "hydroxy" refers to the group —OH.

As used herein, the term "mercapto" refers to the group —SH.

As used herein, the term "cyano" refers to the group —CN.

As used herein, the term "oxo" refers to the group =O.

As used herein, the term "carboxy" refers to the group —C(O)OH. The carboxy group is optionally substituted by alkyl, cycloalkyl, aryl, heteroaryl or heterocycloalkyl, as defined above.

As used herein, the term "guanidino" refers to the group —NHC(=NH)$NH_2$.

As used herein, the term "ureido" refers to the group —NHC(O)NH, or refers to the group —NHC(O)NH $R_d$ wherein $R_d$ is hydrogen, alkyl, cycloalkyl or aryl as defined above.

As used herein, the term "sulfanyl" refers to the group —$SR_c$, wherein $R_c$ may be alkyl, cycloalkyl, aryl, heteroaryl or heterocycloalkyl, as defined above.

As used herein, the term "sulfinyl" refers to the group —S—(O)$R_c$, wherein $R_c$ may be alkyl, cycloalkyl, aryl, heteroaryl or heterocycloalkyl, as defined above.

As used herein, the term "sulfonyl" refers to the group —$S(O)_2R_c$, wherein $R_c$ may be alkyl, cycloalkyl, aryl, heteroaryl or heterocycloalkyl, as defined above.

As used herein, the term "amino" refers to the group —$NH_2$. The amino group is optionally substituted by alkyl, cycloalkyl, aryl, heteroaryl or heterocycloalkyl, as defined above.

As used herein, the term "sulfonylamino" refers to the group —$NHS(O)_2R_c$ wherein $R_c$ is alkyl, cycloalkyl, aryl, heteroaryl or heterocycloalkyl, as defined above.

As used herein, the term "aminocarbonyl" refers to the group —C(O)$NH_2$. The aminocarbonyl group is optionally substituted by alkyl, cycloalkyl, aryl, heteroaryl or heterocycloalkyl, as defined above.

As used herein, the term "acyl" refers to the group —C(O)$R_e$, wherein $R_e$ may be alkyl, cycloalkyl, or heterocycloalkyl as defined herein.

As used herein, the term "aroyl" refers to the group —C(O)$R_b$, wherein $R_b$ is aryl as defined herein.

As used herein, the term "heteroaroyl" refers to the group —C(O)$R_f$, wherein $R_f$ is heteroaryl as defined herein.

As used herein, the term "acyloxy" refers to the group —OC(O)$R_e$, wherein $R_e$ may be alkyl, cycloalkyl, or heterocycloalkyl as defined herein.

As used herein, the term "aroyloxy" refers to the group —OC(O)$R_b$, wherein $R_b$ is aryl as defined herein.

As used herein, the term "heteroaroyloxy" refers to the group —OC(O)$R_f$, wherein $R_f$ is heteroaryl as defined herein.

It is to be understood that the present invention also includes a pharmaceutically acceptable salt and an addition salt of the compound of formula (I), such as a hydrochloride, hydrobromide or trifluoroacetate addition salt and a sodium, potassium or magnesium salt.

The compounds of the present invention may contain one or more asymmetric carbon atoms and may exist in racemic and optically active forms. All of these compounds and diastereomers are incorporated within the scope of the present invention.

Further, the present invention also includes a prodrug form of the inventive compound. A prodrug is an active or inactive compound that is modified chemically through in vivo physiological action, such as hydrolysis, metabolism and the like, into a compound of the present invention following administration of the prodrug to a patient.

Preferably, the prodrug is carboxylate or aminoacetate of the compound of formula (I), the carboxylate or aminoacetate being optionally substituted with at least one substituent selected from the group consisting of $C_{1-7}$ alkyl, $C_{1-7}$ alkoxy, $C_{2-7}$ alkenyl, $C_{2-7}$ alkenyloxy, $C_{6-10}$ aryl, $C_{6-10}$ acyloxy, $C_{6-10}$ aryl-$C_{1-4}$alkyl, $C_{6-10}$ aryl-$C_{1-4}$alkoxy, and $C_{6-10}$ aryl substituted with at least one $C_{1-4}$ alkoxy.

In accordance with one aspect of the present invention, there is provided a compound of formula (I) or a pharmaceutically acceptable salt thereof or a prodrug thereof:

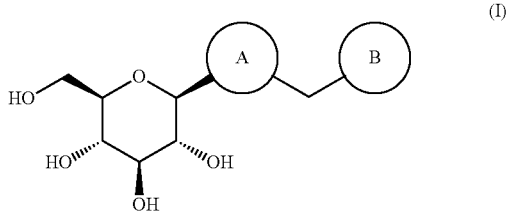

(I)

wherein, ring A is thiophene; and ring B is benzene, 5 to 10-membered heterocycloalkyl, or 5 to 13-membered heteroaryl, and in which said ring A and ring B are each independently optionally substituted with at least one substituent selected from the group consisting of halogen, hydroxy, mercapto, cyano, carboxy, nitro, guanidino, ureido, amino, $C_{1-7}$ alkyl, $C_{2-7}$ alkenyl, $C_{2-7}$ alkynyl, $C_{1-7}$ alkoxy-$C_{1-7}$ alkyl, $C_{1-7}$ alkoxy, $C_{1-7}$ alkoxy-$C_{1-7}$ alkoxy, $C_{2-7}$ alkenyloxy, $C_{2-7}$ alkynyloxy, 5 to 10-membered heterocycloalkyloxy, $C_{3-10}$ cycloalkyl, $C_{5-10}$ cycloalkenyl, $C_{3-10}$ cycloalkyloxy, phenyl-$C_{1-7}$ alkoxy, mono- or di-$C_{1-7}$ alkylamino, aminocarbonyl, $C_{2-8}$ acylamino, $C_{2-8}$ acyl, $C_{1-7}$ alkoxycarbonyl, mono- or di-$C_{1-7}$ alkylcarbamoyl, $C_{1-7}$ alkylsulfonylamino, phenylsulfonylamino, $C_{1-7}$ alkylsulfanyl, $C_{1-7}$ alkylsulfinyl, $C_{1-7}$ alkylsulfonyl, phenylsulfonyl, $C_{6-14}$ aryl, $C_{7-15}$ aroyl, 5 to 13-membered heteroaryl, 6 to 14-membered heteroaroyl, $C_{7-15}$ aroyloxy, $C_{2-8}$ acyloxy, 6 to 14-membered heteroaroyloxy, or 5 to 10-membered heterocycloalkyl, in which said alkyl, alkenyl, alkynyl, alkoxy, or acyl is optionally substituted with a substituent selected from the group consisting of halogen, hydroxy, cyano, nitro, amino, and mercapto; said cycloalkyl, cycloalkenyl, aryl, aroyl, heteroaryl, heteroaroyl, or heterocycloalkyl is optionally substituted with a substituent selected from the group consisting of halogen, hydroxy, cyano, nitro, amino, mercapto, $C_{1-4}$ alkyl, and $C_{1-4}$ alkoxy; and said heterocycloalkyl, heteroaryl, and heteroaroyl each independently contains at least one heteroatom selected from the group consisting of N, O and S.

Preferably, in the compound of the formula (I), the ring B is thiophene, oxazole, thiazole, oxadiazole, or thiadiazaole, in which said ring B is substituted with at least one substituent selected from the group consisting of halogen, hydroxy, mercapto, cyano, carboxy, amino, mono- or di-$C_{1-7}$ alkylamino, guanidino, ureido, $C_{1-7}$ alkoxy, $C_{1-7}$ alkoxy-$C_{1-7}$ alkoxy, $C_{2-7}$ alkenyloxy, $C_{2-7}$ alkynyloxy, $C_{3-10}$ cycloalkyloxy, 5 to 10-membered heterocycloalkyloxy, $C_{1-7}$ alkylsulfanyl, $C_{6-14}$ arylsulfanyl, $C_{1-7}$ alkyl, $C_{2-7}$ alkenyl, $C_{2-7}$ alkynyl, $C_{3-10}$ cycloalkyl, $C_{5-10}$ cycloalkenyl, $C_{6-14}$ aryl, 5 to 13-membered heteroaryl, $C_{2-8}$ acyl, $C_{2-8}$ acyloxy, 6 to 14-membered heteroaroyloxy, $C_{7-15}$ aroyl, $C_{7-15}$ aroyloxy, or 5 to 10-membered heterocycloalkyl, in which said alkyl, alkenyl, alkynyl, alkoxy, or acyl is optionally substituted with a substituent selected from the group consisting of halogen, hydroxy, cyano, nitro, amino, and mercapto; said cycloalkyl, cycloalkenyl, aryl, aroyl, heteroaryl, heteroaroyl, or heterocycloalkyl is optionally substituted with a substituent selected from the group consisting of halogen, hydroxy, cyano, nitro, amino, mercapto, $C_{1-4}$ alkyl, and $C_{1-4}$ alkoxy; and said heterocycloalkyl, heteroaryl, and heteroaroyl each independently contains at least one heteroatom selected from the group consisting of N, O and S.

Preferably, in the compound of the formula (I), the ring A is

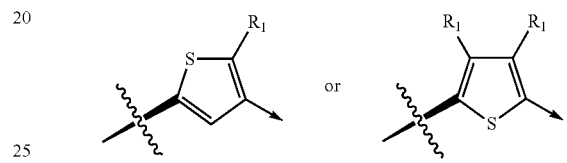

wherein $R_1$ is hydrogen, halogen, hydroxy, mercapto, cyano, carboxy, nitro, guanidino, ureido, amino, $C_{1-7}$ alkyl, $C_{2-7}$ alkenyl, $C_{2-7}$ alkynyl, hydroxyalkyl, $C_{1-7}$ alkoxy-$C_{1-7}$ alkyl, $C_{1-7}$ alkoxy, $C_{3-10}$ cycloalkyl, $C_{5-10}$ cycloalkenyl, $C_{3-10}$ cycloalkyloxy, phenyl-$C_{1-7}$ alkoxy, mono- or di-$C_{1-7}$ alkylamino, aminocarbonyl, $C_{2-8}$ acylamino, $C_{2-8}$ acyl, $C_{1-7}$ alkoxycarbonyl, mono- or di-$C_{1-7}$ alkylcarbamoyl, $C_{1-7}$ alkylsulfonylamino, phenylsulfonylamino, $C_{1-7}$ alkylsulfanyl, $C_{1-7}$ alkylsulfinyl, $C_{1-7}$ alkylsulfonyl, phenylsulfonyl, $C_{6-14}$ aryl, $C_{7-15}$ aroyl, 5 to 13-membered heteroaryl, 6 to 14-membered heteroaroyl, $C_{7-15}$ aroyloxy, $C_{2-8}$ acyloxy, 6 to 14-membered heteroaroyloxy, or 5 to 10-membered heterocycloalkyl; and the ring B is

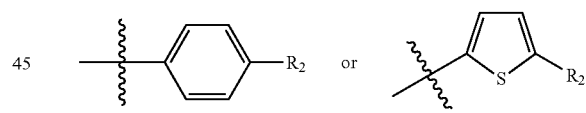

wherein $R_2$ is hydrogen, halogen, hydroxy, mercapto, cyano, carboxy, amino, mono- or di-$C_{1-7}$ alkylamino, guanidino, ureido, $C_{1-7}$ alkoxy, $C_{1-7}$ alkoxy-$C_{1-7}$ alkoxy, $C_{2-7}$ alkenyloxy, $C_{2-7}$ alkynyloxy, $C_{3-10}$ cycloalkyloxy, 5 to 10-membered heterocycloalkyloxy, $C_{1-7}$ alkylsulfanyl, $C_{6-14}$ arylsulfanyl, $C_{1-7}$ alkyl, $C_{2-7}$ alkenyl, $C_{2-7}$ alkynyl, $C_{3-10}$ cycloalkyl, $C_{5-10}$ cycloalkenyl, $C_{6-14}$ aryl, 5 to 13-membered heteroaryl, $C_{2-8}$ acyl, $C_{2-8}$ acyloxy, 6 to 14-membered heteroaroyloxy, $C_{7-15}$ aroyl, $C_{7-15}$ aroyloxy, or 5 to 10-membered heterocycloalkyl, in which said alkyl, alkenyl, alkynyl, alkoxy, or acyl is optionally substituted with a substituent selected from the group consisting of halogen, hydroxy, cyano, nitro, amino, and mercapto; said cycloalkyl, cycloalkenyl, aryl, aroyl, heteroaryl, heteroaroyl, or heterocycloalkyl is optionally substituted with a substituent selected from the group consisting of halogen, hydroxy, cyano, nitro, amino, mercapto, $C_{1-4}$ alkyl, and $C_{1-4}$ alkoxy; and said heterocycloalkyl, heteroaryl, and heteroaroyl each independently contains at least one heteroatom selected from the group consisting of N, O and S.

More preferably, in the compound of the formula (I), $R_1$ is halogen, $C_{1-7}$ alkyl, or $C_{1-7}$ alkoxy; and $R_2$ is halogen, hydroxy, $C_{1-7}$ alkyl, $C_{1-7}$ alkoxy, $C_{1-7}$ alkoxy-$C_{1-7}$ alkoxy, $C_{2-7}$ alkenyloxy, $C_{2-7}$ alkynyloxy, $C_{1-7}$ alkylsulfanyl, $C_{6-14}$ aryl, $C_{3-10}$ cycloalkyloxy, or 5 to 10-membered heterocycloalkyloxy, in which said alkyl or alkoxy is optionally substituted with a substituent selected from the group consisting of halogen, hydroxy, cyano, nitro, amino, and mercapto; said aryl, cycloalkyl, or heterocycloalkyl is optionally substituted with a substituent selected from the group consisting of halogen, hydroxy, cyano, nitro, amino, mercapto, $C_{1-4}$ alkyl, and $C_{1-4}$ alkoxy; and said heterocycloalkyl contains at least one heteroatom selected from the group consisting of N, O and S.

More preferably, in the compound of the formula (I), the ring A is

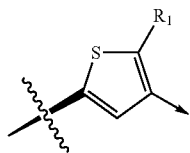

wherein $R_1$ is halogen or $C_{1-7}$ alkyl; or

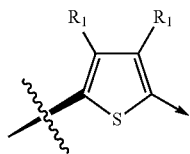

in which $R_1$ is $C_{1-7}$ alkyl, $C_{1-7}$ alkoxy, halogen; and the ring B is

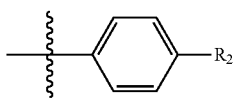

in which $R_2$ is hydroxy, halogen, $C_{1-7}$ alkyl, $C_{1-7}$ alkoxy, $C_{1-7}$ alkoxy-$C_{1-7}$ alkoxy, $C_{1-7}$ alkenyloxy, $C_{1-7}$ alkynyloxy, $C_{1-7}$ alkylthio, $C_{3-7}$ cycloalkyloxy, or 5 to 7-membered heterocycloalkyloxy; or

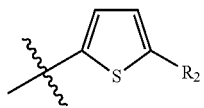

wherein $R_2$ is $C_{6-14}$ aryl substituted or unsubstituted with halogen, in which said heterocycloalkyl contains at least one heteroatom selected from the group consisting of N, O and S.

Preferable compounds in the present invention are selected from the group consisting of:
(1) (2R,3R,4S,5S,6R)-2-(5-chloro-4-(4-ethoxybenzyl)thiophen-2-yl)-6-(hydroxymethyl)-tetrahydro-2H-pyran-3,4,5-triol;
(2) (2R,3R,4S,5S,6R)-2-(5-chloro-4-(4-methoxybenzyl)thiophen-2-yl)-6-(hydroxymethyl)-tetrahydro-2H-pyran-3,4,5-triol;
(3) (2R,3R,4S,5S,6R)-2-(5-chloro-4-((5-(4-fluorophenyl)thiophen-2-yl)methyl)thiophen-2-yl)-6-(hydroxymethyl)-tetrahydro-2H-pyran-3,4,5-triol;
(4) (2R,3R,4S,5S,6R)-2-(4-(4-(allyloxy)benzyl-5-chlorothiophen-2-yl)-6-(hydroxymethyl)-tetrahydro-2H-pyran-3,4,5-triol;
(5) (2R,3R,4S,5S,6R)-2-(5-chloro-4-(4-propoxybenzyl)thiophen-2-yl)-6-(hydroxymethyl)-tetrahydro-2H-pyran-3,4,5-triol;
(6) (2R,3R,4S,5S,6R)-2-(5-chloro-4-(4-hydroxybenzyl)thiophen-2-yl)-6-(hydroxymethyl)-tetrahydro-2H-pyran-3,4,5-triol;
(7) (2R,3R,4S,5S,6R)-2-(5-chloro-4-(4-(ethylthio)benzyl)thiophen-2-yl)-6-(hydroxymethyl)-tetrahydro-2H-pyran-3,4,5-triol;
(8) (2R,3R,4S,5S,6R)-2-(5-chloro-4-(4-(prop-2-ynyloxy)benzyl)thiophen-2-yl)-6-(hydroxymethyl)-tetrahydro-2H-pyran-3,4,5-triol;
(9) (2R,3R,4S,5S,6R)-2-(5-chloro-4-(4-isopropoxybenzyl)thiophen-2-yl)-6-(hydroxymethyl)-tetrahydro-2H-pyran-3,4,5-triol;
(10) (2R,3R,4S,5S,6R)-2-(5-chloro-4-(4-(2-methoxyethoxy)benzyl)thiophen-2-yl)-6-(hydroxymethyl)-tetrahydro-2H-pyran-3,4,5-triol;
(11) (2R,3R,4S,5S,6R)-2-(5-chloro-4-(4-(cyclopentyloxy)benzyl)thiophen-2-yl)-6-(hydroxymethyl)-tetrahydro-2H-pyran-3,4,5-triol;
(12) (2R,3R,4S,5S,6R)-2-(5-chloro-4-(4-(methylthio)benzyl)thiophen-2-yl)-6-(hydroxymethyl)-tetrahydro-2H-pyran-3,4,5-triol;
(13) (2R,3R,4S,5S,6R)-2-(5-chloro-4-(4-(2-ethoxyethoxy)benzyl)thiophen-2-yl)-6-(hydroxymethyl)-tetrahydro-2H-pyran-3,4,5-triol;
(14) (2R,3R,4S,5S,6R)-2-(5-chloro-4-(4-methylbenzyl)thiophen-2-yl)-6-(hydroxymethyl)-tetrahydro-2H-pyran-3,4,5-triol;
(15) (2R,3R,4S,5S,6R)-2-(4-(4-(but-2-ynyloxy)benzyl)-5-chlorothiophen-2-yl)-6-(hydroxymethyl)-tetrahydro-2H-pyran-3,4,5-triol;
(16) (2R,3R,4S,5S,6R)-2-(5-chloro-4-(4-(tetrahydrofuran-3-yloxy)benzyl)thiophen-2-yl)-6-(hydroxymethyl)-tetrahydro-2H-pyran-3,4,5-triol;
(17) (2R,3R,4S,5S,6R)-2-(5-chloro-4-(4-ethylbenzyl)thiophen-2-yl)-6-(hydroxymethyl)-tetrahydro-2H-pyran-3,4,5-triol;
(18) (2R,3R,4S,5S,6R)-2-(5-chloro-4-(4-propylbenzyl)thiophen-2-yl)-6-(hydroxymethyl)-tetrahydro-2H-pyran-3,4,5-triol;
(19) (2R,3R,4S,5S,6R)-2-(4-(4-ethoxybenzyl)-5-methylthiophen-2-yl)-6-(hydroxymethyl)-tetrahydro-2H-pyran-3,4,5-triol;
(20) (2R,3S,4S,5R,6R)-2-(hydroxymethyl)-6-(4-(4-methoxybenzyl)-5-methylthiophen-2-yl)-tetrahydro-2H-pyran-3,4,5-triol;
(21) (2R,3R,4S,5S,6R)-2-(4-((5-(4-fluorophenyl)thiophen-2-yl)methyl)-5-methylthiophen-2-yl)-6-(hydroxymethyl)-tetrahydro-2H-pyran-3,4,5-triol;
(22) (2R,3R,4S,5S,6R)-2-(4-(4-(allyloxy)benzyl)-5-methylthiophen-2-yl)-6-(hydroxymethyl)-tetrahydro-2H-pyran-3,4,5-triol;
(23) (2R,3R,4S,5S,6R)-2-(4-(4-hydroxybenzyl)-5-methylthiophen-2-yl)-6-(hydroxymethyl)-tetrahydro-2H-pyran-3,4,5-triol;
(24) (2R,3S,4S,5R,6R)-2-(hydroxymethyl)-6-(4-methyl-5-(4-propylbenzyl)thiophen-2-yl)tetrahydro-2H-pyran-3,4,5-triol;

(25) (2R,3R,4S,5S,6R)-2-(5-(4-ethylbenzyl)-4-methylthiophen-2-yl)-6-(hydroxymethyl)tetrahydro-2H-pyran-3,4,5-triol;
(26) (2R,3S,4S,5R,6R)-2-(hydroxymethyl)-6-(4-methyl-5-(4-methylbenzyl)thiophen-2-yl)tetrahydro-2H-pyran-3,4,5-triol;
(27) (2R,3R,4S,5S,6R)-2-(5-(4-tert-butylbenzyl)-4-methylthiophen-2-yl)-6-(hydroxymethyl)tetrahydro-2H-pyran-3,4,5-triol;
(28) (2R,3R,4S,5S,6R)-2-(5-(4-chlorobenzyl)-4-methylthiophen-2-yl)-6-(hydroxymethyl)tetrahydro-2H-pyran-3,4,5-triol;
(29) (2R,3R,4S,5S,6R)-2-(5-(4-fluorobenzyl)-4-methylthiophen-2-yl)-6-(hydroxymethyl)tetrahydro-2H-pyran-3,4,5-triol;
(30) (2R,3S,4S,5R,6R)-2-(hydroxymethyl)-6-(5-(4-methoxybenzyl)-4-methylthiophen-2-yl)tetrahydro-2H-pyran-3,4,5-triol;
(31) (2R,3R,4S,5S,6R)-2-(5-(4-ethoxybenzyl)-4-methylthiophen-2-yl)-6-(hydroxymethyl)tetrahydro-2H-pyran-3,4,5-triol;
(32) (2R,3R,4S,5S,6R)-2-(3-bromo-5-(4-ethylbenzyl)-4-methylthiophen-2-yl)-6-(hydroxymethyl)tetrahydro-2H-pyran-3,4,5-triol;
(33) (2R,3R,4S,5S,6R)-2-(5-(4-ethylbenzyl)-3-methoxy-4-methylthiophen-2-yl)-6-(hydroxymethyl)tetrahydro-2H-pyran-3,4,5-triol; and
(34) (2R,3R,4S,5S,6R)-2-(5-(4-ethylbenzyl)-3,4-dimethylthiophen-2-yl)-6-(hydroxymethyl)tetrahydro-2H-pyran-3,4,5-triol.

Accordingly, the present invention provides a pharmaceutical composition for preventing or treating a metabolic disorder, which comprises the compound of formula (I), or a pharmaceutically acceptable salt or a prodrug thereof as an active ingredient and a pharmaceutically acceptable carrier.

The metabolic disorder may be diabetes, cardiovascular disease, or hypertension, preferably diabetes.

Further, the present invention provides a method for preventing or treating a metabolic disorder in a mammal, which comprises administering the compound of formula (I) or a pharmaceutically acceptable salt or a prodrug thereof to the mammal.

Also, the present invention provides a method for inhibiting SGLT2 in a mammal, which comprises administering the compound of formula (I) or a pharmaceutically acceptable salt or a prodrug thereof to the mammal.

The pharmaceutical composition may be administered orally or parenterally, e.g., intramuscularly or subcutaneously. The formulation for oral administration may take various forms such as a syrup, tablet, capsule, cream and lozenge. A syrup formulation will generally contain a suspension or solution of the compound or its salt in a liquid carrier, e.g., ethanol, peanut oil, olive oil, glycerine or water, optionally with a flavoring or coloring agent. When the composition is in the form of a tablet, any one of pharmaceutical carriers routinely used for preparing solid formulations may be used. Examples of such carriers include magnesium stearate, terra alba, talc, gelatin, acacia, stearic acid, starch, lactose and sucrose. When the composition is in the form of a capsule, any of the routine encapsulation procedures may be employed, e.g., using the aforementioned carriers in a hard gelatin capsule shell. When the composition is formulated in the form of a soft gelatin shell capsule, any of the pharmaceutical carrier routinely used for preparing dispersions or suspensions may be prepared using an aqueous gum, cellulose, silicate or oil. The formulation for intramuscular or subcutaneous administration may take a liquid form such as a solution, suspension and emulsion which includes aqueous solvents such as water, physiological saline and Ringer's solution; or lipophilic solvents such as fatty oil, sesame oil, corn oil and synthetic fatty acid ester.

Preferably the composition is formulated in a specific dosage form for a particular patient.

Each dosage unit for oral administration contains suitably from 0.1 mg to 500 mg, and preferably from 1 mg to 100 mg of the compound of formula (I) or its pharmaceutically acceptable salt or prodrug.

The suitable daily dosage for oral administration is about 0.01 mg/kg body weight to 40 mg/kg body weight of the compound of formula (I) or its pharmaceutically acceptable salt or prodrug, and may be administered 1 to 6 times a day, depending on the patient's condition.

The present invention further provides a use of the compound of formula (I) or a pharmaceutically acceptable salt or a prodrug thereof for the manufacture of a medicament for preventing or treating a metabolic disorder, particularly diabetes.

The present invention also provides a method for preparing the compound of formula (I), comprising (a) reacting a compound of formula (III) with a compound of formula (IV), followed by reduction, to obtain a compound of formula (V); and (b) reacting the compound of formula (V) with a compound of formula (II), followed by deprotection, to obtain the compound of formula (I):

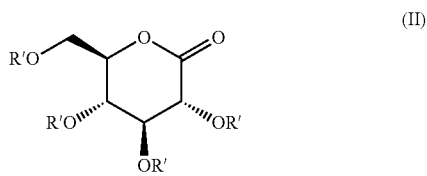

(II)

(III)

(IV)

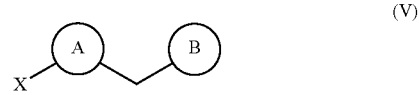

(V)

wherein, R' is tetramethylsilane or benzyl; X is halogen; X' is —C(=O)X" or —CH$_2$X"; X" is hydroxy, halogen, or C$_{1-7}$alkoxy; and ring A and ring B have the same meaning as defined above.

Further, the present invention provides a method for preparing the compound of formula (I), comprising (a) reacting a compound of formula (III) with a compound of formula (II), followed by reduction, to obtain a compound of formula (VI); and (b) reacting the compound of formula (VI) with a compound of formula (IV), followed by deprotection, to obtain the compound of formula (I):

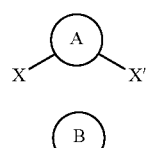

(II)

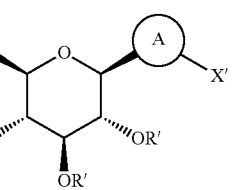

(III)

(IV)

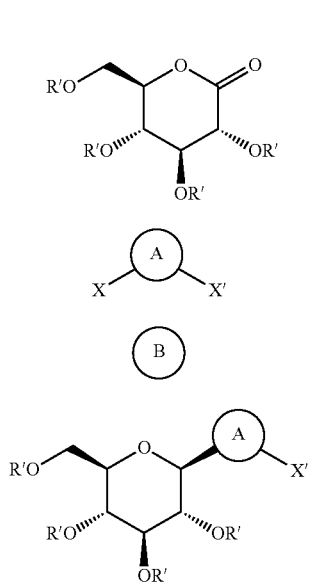

(VI)

wherein, R' is tetramethylsilane or benzyl; X is halogen; X' is —C(=O)X" or —CH$_2$X"; X" is hydroxy, halogen, or C$_{1-7}$alkoxy; and ring A and ring B have the same meaning as defined above.

The compounds of the present invention and the preparation thereof will be better understood in connection with the following synthetic schemes, which are merely illustrative of the methods by which the compounds of the invention may be prepared and are not intended to limit the scope of the invention as defined in the appended claims.

General Synthetic Sequence

Scheme 1

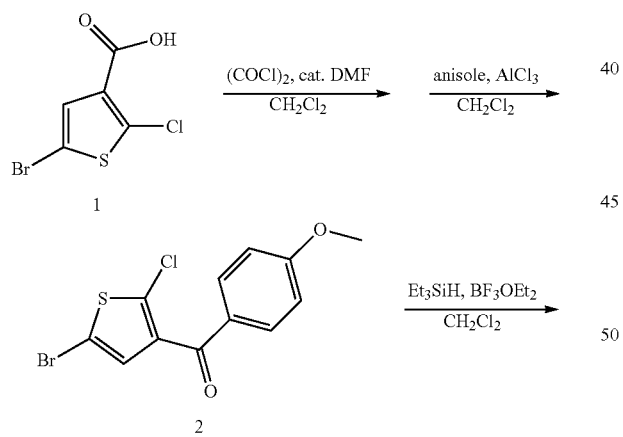

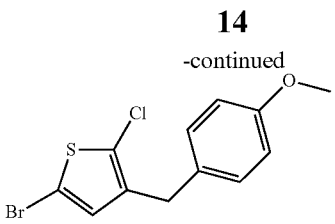

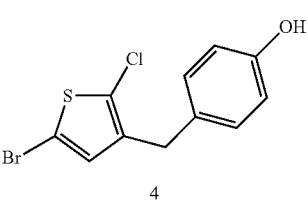

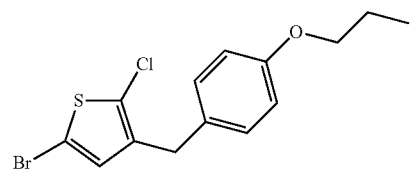

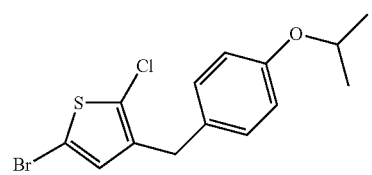

The synthesis of various thienyl bromides is as shown in Scheme 1. Friedel-Crafts acylation of anisole with 5-bromo-2-chlorothiophene-3-carbonyl chloride, formed form 5-bromo-2-chlorothiophene-3-carboxylic acid 1 with oxalyl chloride, generates the desired diarylketone 2 in about 98% yield. The reduction of diarylketone 2 by triethylsilane in the presence of boron trifluoride etherate provides aglycon 3 in about 82% yield. 4-((5-Bromo-2-chlorothiophen-3-yl)methyl)phenol, the key intermediate 4, is generated via demethylation with BBr$_3$ in quantitative yield. Alkylated aglycons such as 5 or 6 are generated via alkylation with alkyl halide in the presence of suitable base such as cesium carbonate or with corresponding alcohol with DIAD and PPh$_3$ under Mitsunobu reaction conditions.

Scheme 2

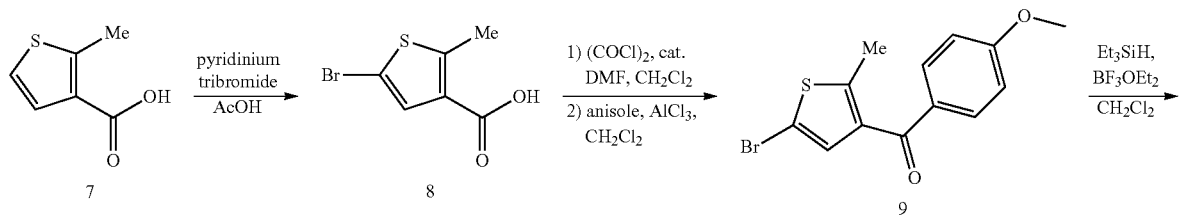

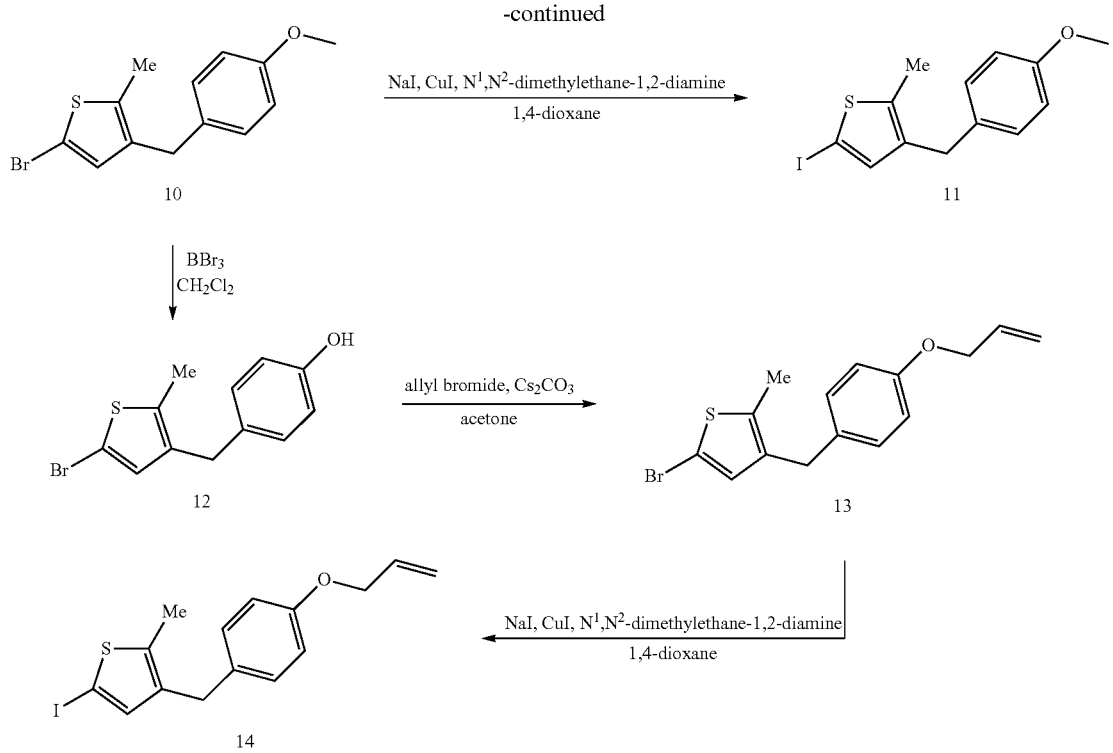

The synthesis of various thienyl iodides is shown in Scheme 2. 5-Bromo-2-methylthiophene-3-carboxylic acid 8 is obtained in good yield (about 84%) by bromination at the thiophene ring of 2-methylthiophene-3-carboxylic acid 7 using bromine generated from pyridinium tribromide in glacial acetic acid. Friedel-Crafts acylation of anisole with 5-bromo-2-methylthiophene-3-carbonyl chloride, formed from 5-bromo-2-chlorothiophene-3-carboxylic acid 8 with oxalyl chloride, generates the desired diarylketone 9 in about 83% yield. The reduction of diarylketone 9 by triethylsilane in the presence of boron trifluoride etherate provides aglycon 10 in quantitative yield. A copper-catalyzed halogen exchange reaction is performed to prepare thienyl iodides 11 from the corresponding bromides 10 using N,N'-dimethylethylenediamine ligand at high temperature, e.g., 120° C.

As in Scheme 2, phenol 12 is generated via demethylation of aglycon 10 with BBr$_3$. Alkylation of aglycon 11 with alkyl halide under basic conditions, followed by copper-catalyzed halogen exchange reaction in the presence of NaI, CuI and N,N'-dimethylethylenediamine ligand at high temperature, e.g., 120° C., produces the corresponding iodides 14 in high yield.

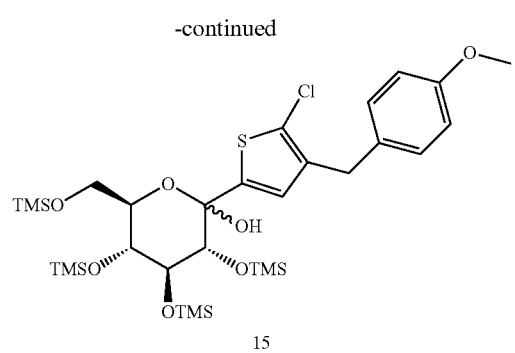

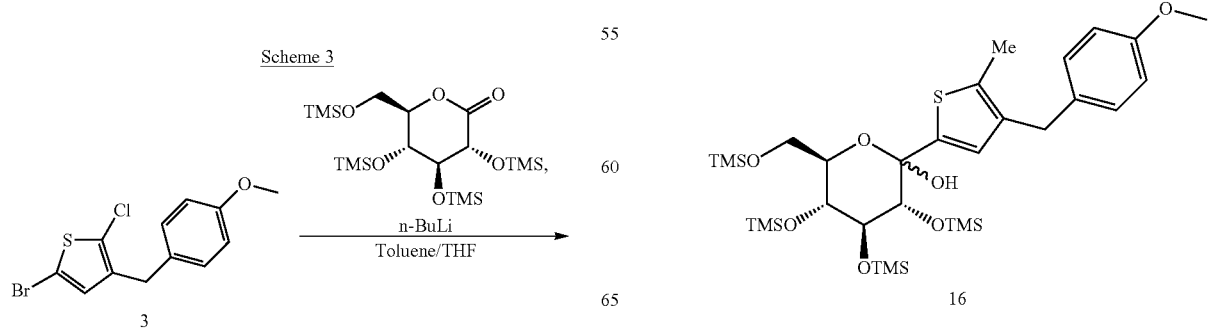

The general procedures for addition of organometallic compound to gluconolactone which are utilized in this invention are illustrated in Scheme 3. Thus, lithium-bromine exchange of bromide 3 using n-butyllithium, followed by addition of the nascent lithiated aromatic compound to gluconolactone, produces a mixture of the corresponding lactols 15. Alternatively, a mixture of lactols 16 is smoothly prepared via lithium-iodine exchange of 11 using (trimethylsilyl)methyllithium.

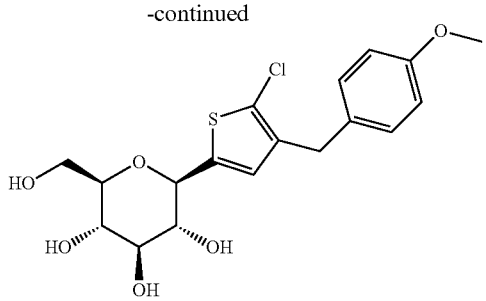

The synthesis of a target compound, β-anomer of tetraol 20 is illustrated in Scheme 4. First, the lactol 15 is converted in situ to the desilylated O-methyl lactols by treatment with methansulfonic acid in methanol at cold conditions, e.g., −78 to −50° C. The reduction of the anomeric methoxy group of lactol 17 using triethylsilane and boron trifluoride diethyl etherate is performed to generate the corresponding tetraol 18. Finally, peracetylation using Et$_3$N and acetic anhydride in the presence of DMAP, subsequently selective crystallization from ethanol, followed by hydrolysis using sodium methoxide yields the target compound 20 in about 48% yield for the five steps.

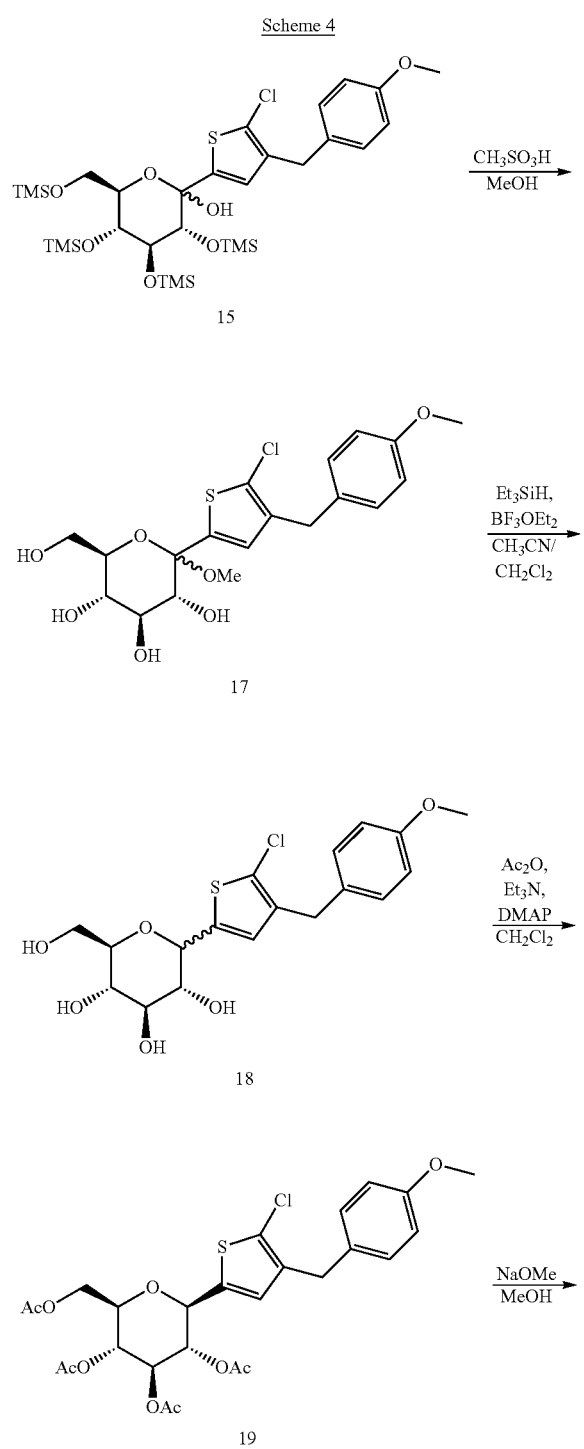

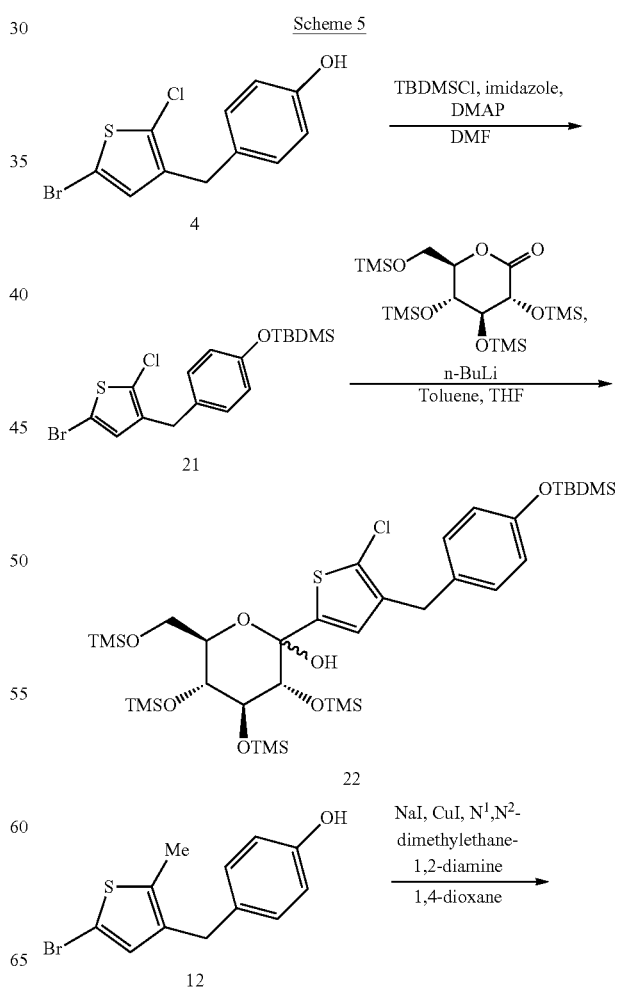

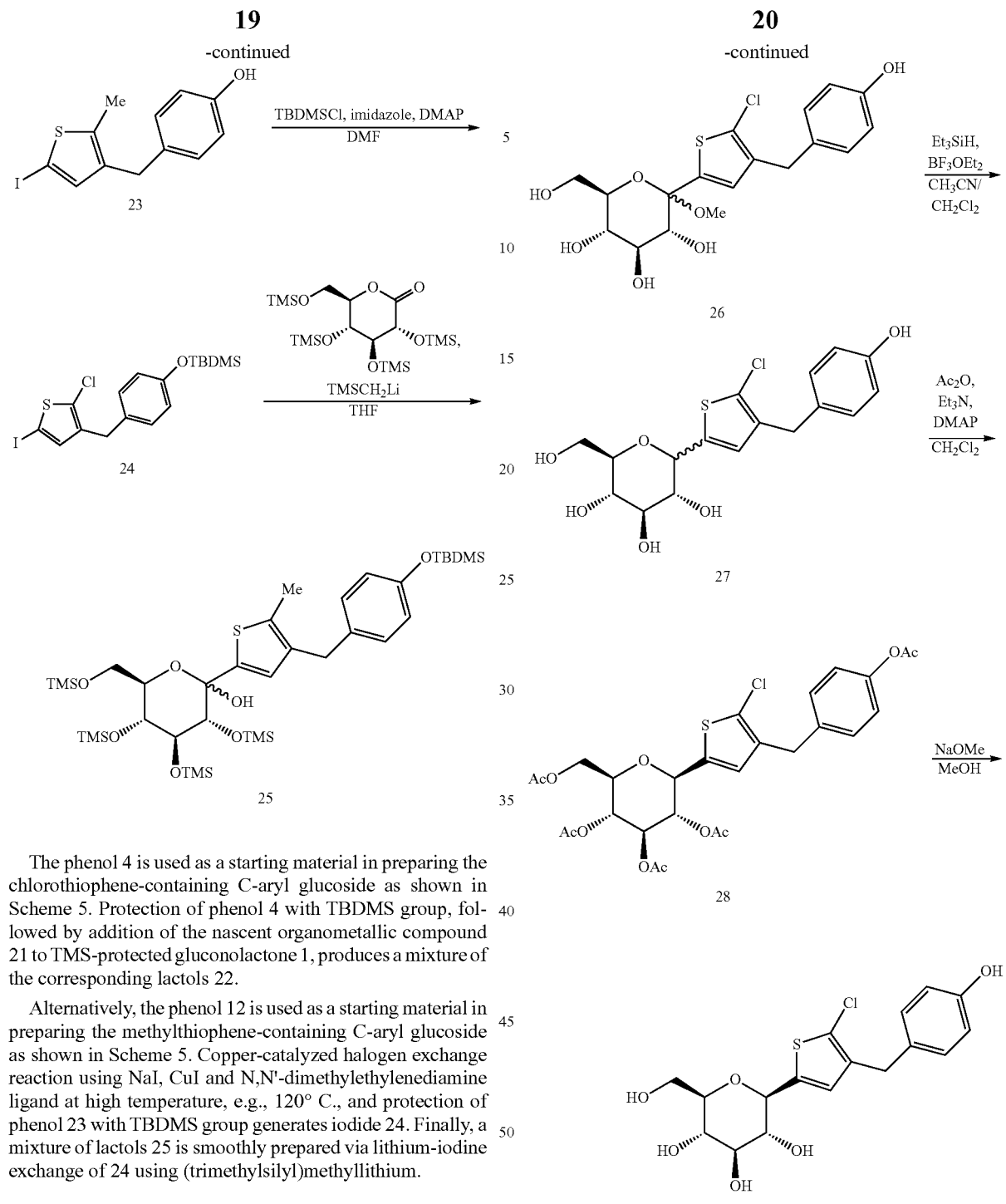

The phenol 4 is used as a starting material in preparing the chlorothiophene-containing C-aryl glucoside as shown in Scheme 5. Protection of phenol 4 with TBDMS group, followed by addition of the nascent organometallic compound 21 to TMS-protected gluconolactone 1, produces a mixture of the corresponding lactols 22.

Alternatively, the phenol 12 is used as a starting material in preparing the methylthiophene-containing C-aryl glucoside as shown in Scheme 5. Copper-catalyzed halogen exchange reaction using NaI, CuI and N,N'-dimethylethylenediamine ligand at high temperature, e.g., 120° C., and protection of phenol 23 with TBDMS group generates iodide 24. Finally, a mixture of lactols 25 is smoothly prepared via lithium-iodine exchange of 24 using (trimethylsilyl)methyllithium.

Scheme 6

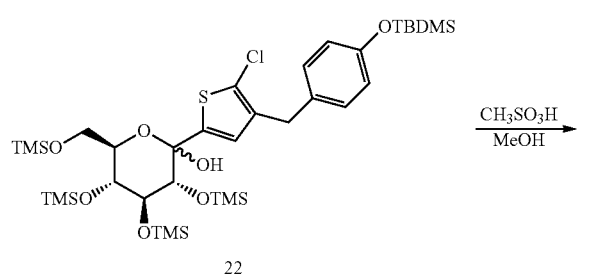

The synthesis of β-anomer of pentaol 29 is shown in Scheme 6. First, the lactol 22 is converted in situ to the desilylated O-methyl lactols 26 by treatment with methansulfonic acid in methanol at low temperature, e.g., −78 to −50° C. The reduction of the anomeric methoxy group of lactol 26 using triethylsilane and boron trifluoride diethyl etherate is performed to generate the corresponding mixture of pentaol 27. Finally, peracetylation using Et₃N and acetic anhydride in the presence of DMAP, selective crystallization from ethanol, followed by hydrolysis using sodium methoxide yields the pentaol 29 in 20% yield for the five steps.

Scheme 7
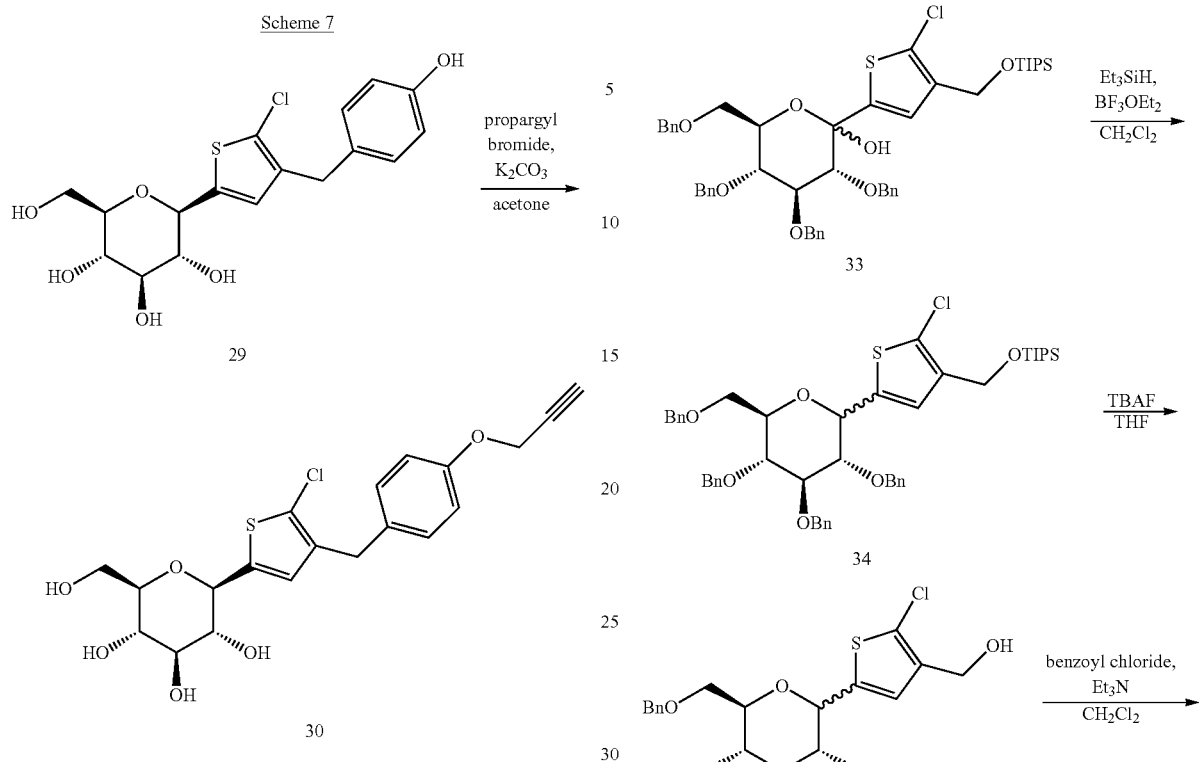
The derivatization of pentaol 29 is shown in Scheme 7. The phenol 29 is alkylated with alkyl halide under basic conditions to provide ether 30, albeit in low yield.
Scheme 8
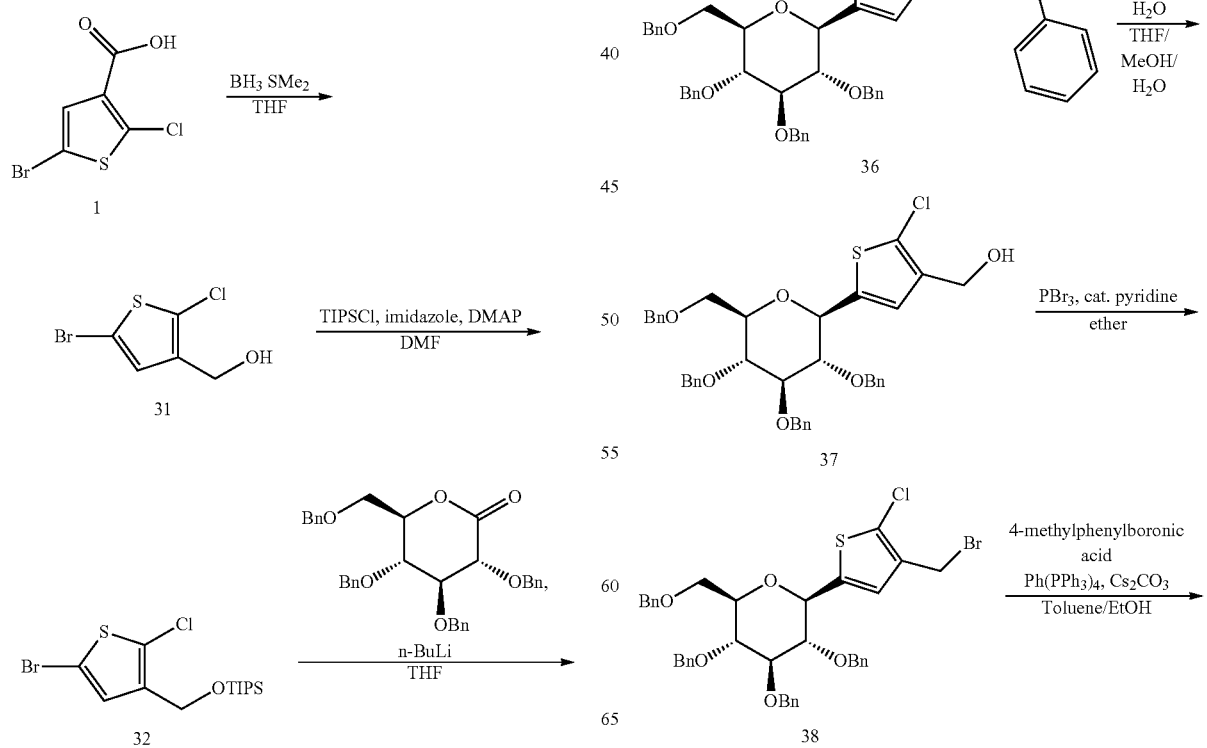

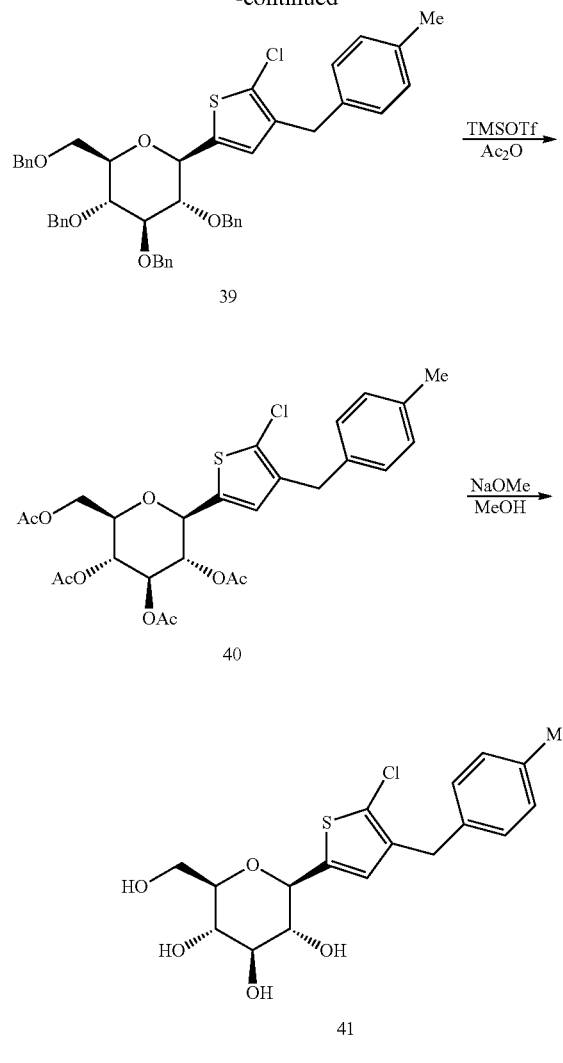

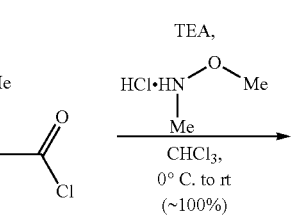

Scheme 9

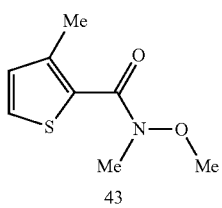

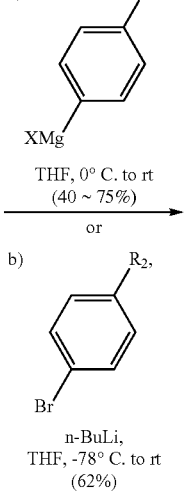

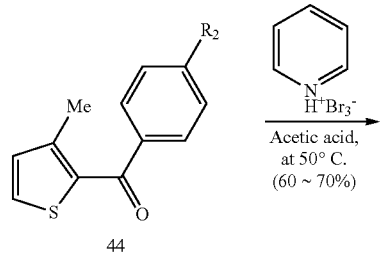

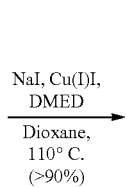

Another route of synthesis of chlorothiophene-containing C-aryl glucoside is shown in Scheme 8. Reduction of acid 1 with borane dimethylsulfide, followed by protection of the resulting alcohol 31 with TIPSCl produces bromide 32. Metal-halogen exchange of halogenated compound 32 with n-butyllithium, followed by addition of the nascent organometallic compound to perbenzylated gluconolactone, produces a mixture of the corresponding lactols 33, which are reduced using triethylsilane and boron trifluoride diethyl etherate, followed by desilylation, affords alcohol 35 in about 89% yield for three steps. The alcohol 35 is converted to benzoate with benzoyl chloride in the presence of Et₃N. A mixture of α,β-isomers of 36 is resolved after selective crystallization from ethanol to produce the required β-isomer 36 in high separation yield. Hydrolysis of benzoate 36 with lithium hydroxide monohydrate in aqueous ethanol and THF solution generates β-isomer of alcohol 37 in high yield. The alcohol 37 is converted to bromide 38 using phosphorus tribromide and pyridine. The bromide 38 is coupled with corresponding boronic acid in the presence of Pd catalyst and Cs₂CO₃. Finally, peracetylation using acetic anhydride in the presence of TMSOTf, followed by hydrolysis using sodium methoxide yields the target compound 41 in 17% yield for the two steps.

25
-continued

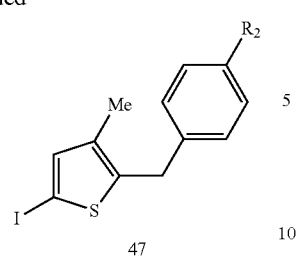

In Scheme 9, $R_2$ has the same meaning as defined in formula (I).

An efficient conversion of 3-methylthiophene-2-carbonyl chloride 42 into a Weinreb amide 43 is achieved by treatment of N,O-dimethylhydroxylamine hydrochloride and TEA under mild conditions in quantitative yield. Reaction of Weinreb amide 43 with proper organometallic nucleophiles, such as Grignard reagents (route a) and organolithium reagents (route b), produces the desired ketones 44. Bromothiophenyl intermediate 45 is obtained in good yield (60 to 70%) by bromination at the thiophene ring of 44 using bromine generated from pyridinium tribromide in glacial acetic acid. The reduction of diaryl ketone 45 to compound 46 is accomplished by treatment of excess triethylsilane in the presence of boron trifluoride etherate. The copper-catalyzed halogen exchange reaction is performed to produce thienyl iodides 47 from the corresponding bromides 46 using N,N'-dimethylethylenediamine ligand at high temperature, e.g., 110° C.

Scheme 10

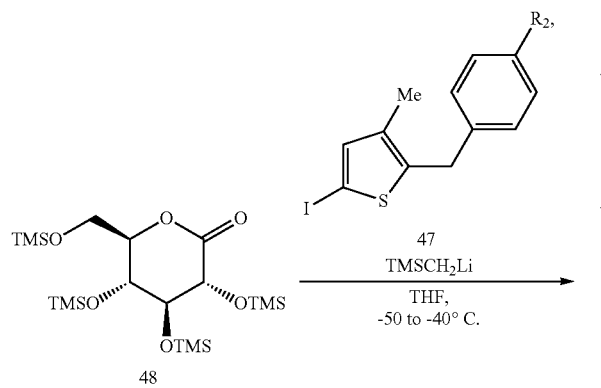

26
-continued

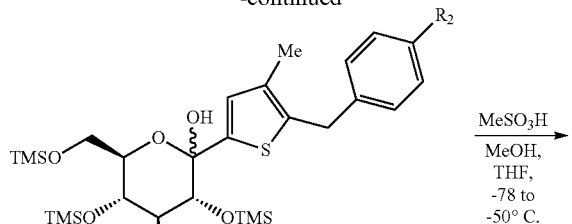

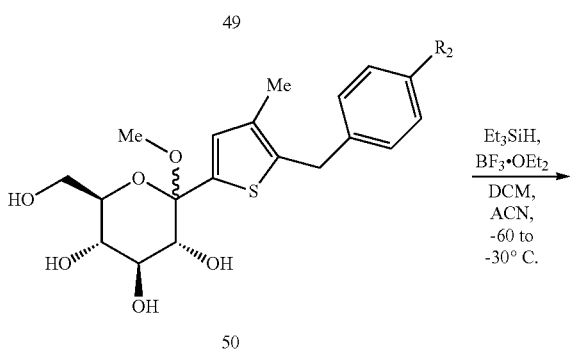

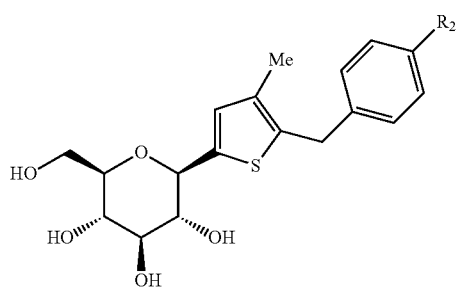

In Scheme 10, $R_2$ has the same meaning as defined in formula (I).

Lithiated thienyl moieties are prepared from the corresponding thienyl iodides 47 by treatment of (trimethylsilyl)methyllithium and coupled with persilylated lactone 48 at low temperature, e.g., −50 to −40° C. The resulting lactols 49 are converted in situ to the desilylated O-methyl lactols 50 by treatment with methanesulfonic acid in methanol at low temperature, e.g., −78 to −50° C. The anomeric methoxy group of 50 is reduced using triethylsilane and $BF_3$ etherate to generate the corresponding tetraol 51. The small amount of α-anomer and other impurities in the crude tetraols 51 are removed by reverse phase preparative HPLC to afford the target compounds 51.

Scheme 11

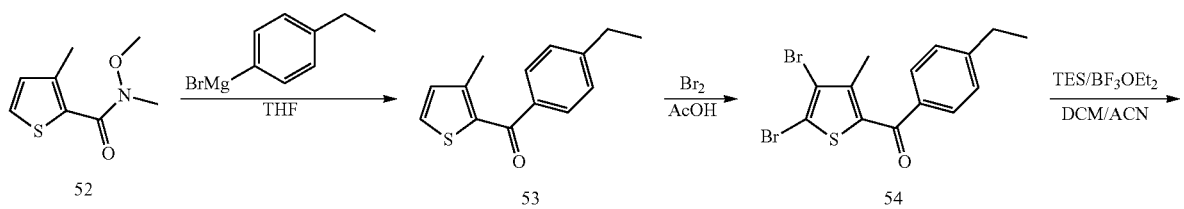

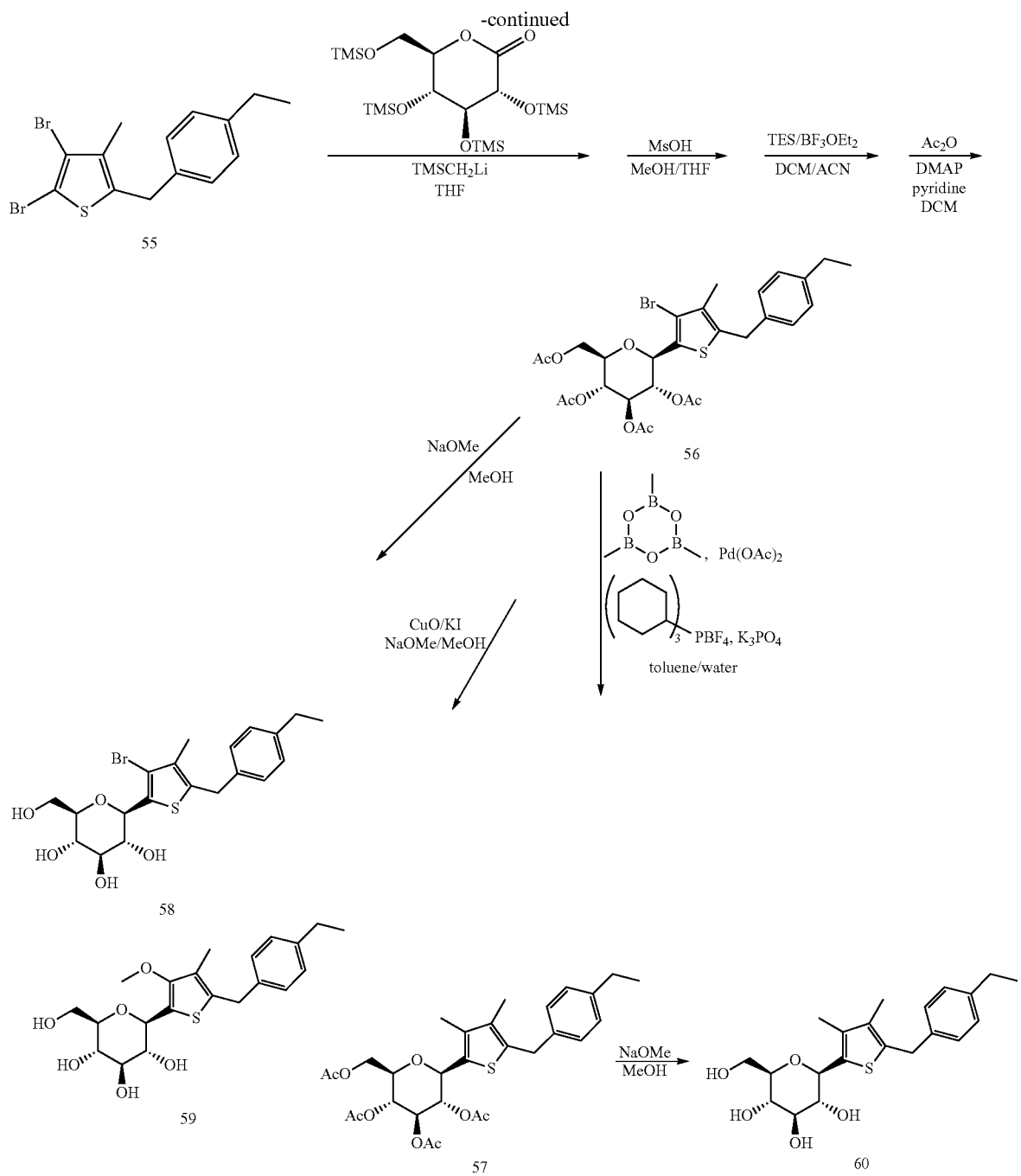

Another approach toward C-aryl glucoside 3-methylthiophene is described in Scheme 11. Thus, bromide 56 undergoes Suzuki-type coupling reaction (trimethylboroxine, tricyclohexylphosphine tetrafluoroborate, Pd(OAc)$_2$, K$_3$PO$_4$, aq. toluene, reflux for 18 h) to transform to dimethylthiophene 57 in 70% yield. Hydrolysis of 56 and 57 with sodium methoxide in methanol produces the desired 3-bromo-4-methylthiophenyl compound 58 and 3,4-dimethylthiophenyl compound 60, respectively. Also, bromide 56 undergoos Ullmann-type coupling and concomitant total deacetylation to provide 3-methoxy-4-methylthiophenyl compound 59.

EXPERIMENTAL SECTION

As used herein the symbols and conventions used describing the processes, schemes and examples of the present invention are consistent with those used in the contemporary scientific literature, for example, the *Journal of the American Chemical Society* or the *Journal of Biological Chemistry*.

Hz (Hertz)
T$_r$ (retention time)
MeOH (methanol)
TEA (triethylamine)
THF (tetrahydrofuran)
DMSO (dimethylsulfoxide)

DCM (dichlromethane)
DMF (N,N-dimethylformamide)
TBAF (tetra-n-butylammonium fluoride)
DMAP (4-dimethylaminopyridine)
HPLC (high pressure liquid chromatography)
TMSOTf (trimethylsilyl trifluoromethanesulfonate)
TLC (thin layer chromatography)
RP (reverse phase)
TFA (trifluoroacetic acid)
EtOH (ethanol)
EtOAc (ethyl acetate)
HOAc (acetic acid)
Ac (acetyl)
Bn (benzyl)
TIPS (triisopropylsilanyl)

All reactions are conducted under an inert atmosphere at room temperature, unless otherwise noted. n-Butyllithium (Aldrich) was titrated with N-benzylbenzamide as indicator. All reagents were purchased at the highest commercial quality and used without further purification, unless otherwise indicated. All experiment involving moisture- and/or air-sensitive compounds were performed in oven- and/or flame-dried glassware with rubber septa under a positive pressure of nitrogen using standard Schlenck technique. Microwave reaction was conducted with a Biotage Initiator microwave reactor. NMR spectra were obtained on a Varian 400-MR (400 MHz $^1$H, 100 MHz $^{13}$C) spectrometer. NMR spectra were recorded in ppm (δ) relative to tetramethylsilane (δ=0.00) as an internal standard unless stated otherwise and are reported as follows: chemical shift, multiplicity (s=singlet, d=doublet, t=triplet, q=quartet, quint=quintet, sext=sextet, m=multiplet, and br=broad), coupling constant, and integration. $^{13}$C NMR spectra were referenced to the residual chloroform-d$_1$ (δ=77.0) or DMSO-d$_6$ (δ=39.7). Mass spectra were obtained with an Agilent 6110 quadruple LC-MSD (ESI+). High resolution mass spectra were obtained on a Jeol JMS-700 Mstation (10 kV, HFAB). Optical rotations were obtained on a Rudolph Autopol III digital polarimeter. Preparative HPLC purifications were performed on a Gilson purification system. For preparative HPLC, ca. 100 mg of a product was injected in 1 mL of methanol onto a SunFire Prep C18 OBD 5 μm 30×100 mm Column with a 30 min gradient from 5 to 90% acetonitrile in water and a 45 mL/min flow rate. Biotage SP1 and Isolera purification systems were used for normal phase column chromatography with ethyl acetate and hexane. Flash chromatography was performed using E. Merck 230-400 mesh silica gel according to the procedure of Still et al. Reactions were monitored by either thin-layer chromatography (TLC) on 0.25 mm E. Merck silica gel plates (60F-254) using UV light and p-anisaldehyde solution as visualizing agents or HPLC analysis on an Agilent 1200 series system.

The following synthetic schemes are merely illustrative of the methods by which the compounds of the invention may be prepared and are not intended to limit the scope of the invention as defined in the appended claims.

Preparation Example 5-bromo-2-chlorothiophene-3-carboxylic acid (1)

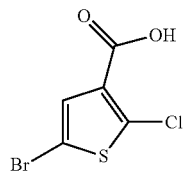

The title compound 1 was prepared from commercially available 2-chloro-3-methylthiophene according to the known procedure (U.S. Pat. No. 5,840,917 A1).

Preparation Example (5-bromo-2-chlorothiophen-3-yl)(4-methoxyphenyl)methanone (2)

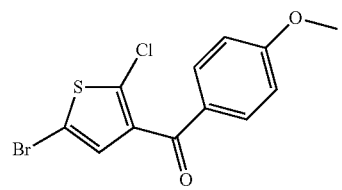

To a solution of acid 1 (2.0 g, 8.28 mmol) in CH$_2$Cl$_2$ (50 mL) were added oxalyl chloride (0.87 mL, 9.94 mmol) and catalytic amounts of DMF at room temperature. The mixture was stirred at room temperature for 3 hours. The mixture was evaporated in vacuo and dried under high vacuum. The crude acid chloride was dissolved with CH$_2$Cl$_2$ (30 mL) and cooled to 0° C. To the mixture was added anisole (0.9 mL, 8.28 mmol) at 0° C. and stirred at 0° C. for 5 min. To the reaction mixture was added AlCl$_3$ (1.2 g, 8.28 mmol) portionwise at 0° C. The mixture was stirred at 0° C. for 30 min, warmed up to room temperature and stirred at room temperature for 15 hours. The mixture was poured into ice-water and extracted with CH$_2$Cl$_2$ (50 mL×2). The combined organic layer was dried over MgSO$_4$, filtered, and concentrated in vacuo. The residue was purified by silica column chromatography (Biotage) to provide the title compound 2 (2.68 g, 98%).

$^1$H NMR (400 MHz, CDCl$_3$) δ 7.83 (d, J=8.4 Hz, 2H), 7.01 (s, 1H), 6.96 (d, J=8.4 Hz, 2H), 3.90 (s, 3H).

Preparation Example 5-bromo-2-chloro-3-(4-methoxybenzyl)thiophene (3)

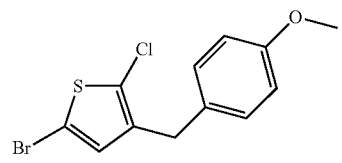 [SMILES: COc1ccc(Cc2cc(Br)sc2Cl)cc1]

To a solution of methanone 2 (2.68 g, 8.08 mmol) in CH$_2$Cl$_2$/CH$_3$CN (20 mL/20 mL) were added triethylsilane (3.9 mL, 24.2 mmol) and boron trifluoride diethyl etherate (3.1 mL, 24.2 mmol) at 0° C. The mixture was warmed up to room temperature slowly and stirred at room temperature for 15 hours. To the mixture was added aq. saturated K$_2$CO$_3$ solution (50 mL) slowly and extracted with EtOAc (50 mL×2). The combined organic layer was dried over MgSO$_4$, filtered, and concentrated in vacuo. The residue was purified by silica column chromatography (Biotage) to provide the desired product 3 (2.09 g, 82%).

$^1$H NMR (400 MHz, CDCl$_3$) δ 7.09 (d, J=8.0 Hz, 2H), 6.83 (d, J=8.0 Hz, 2H), 6.66 (s, 1H), 3.80 (s, 2H), 3.78 (s, 3H).

Preparation Example 4-((5-bromo-2-chlorothiophen-3-yl)methyl)phenol (4)

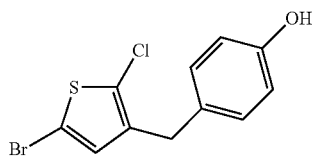 [SMILES: Oc1ccc(Cc2cc(Br)sc2Cl)cc1]

To a solution of thiophene 3 (5.44 g, 17.1 mmol) in CH$_2$Cl$_2$ (50 mL) was added boron tribromide (20 mL, 1M in CH$_2$Cl$_2$) at 0° C. The mixture was warmed up to room temperature slowly and stirred at room temperature for 3 hours. To the mixture was added aq. 1N HCl solution (35 mL) dropwise at 0° C. and H$_2$O was added to the mixture. The mixture was extracted with EtOAc (50 mL×2). The combined organic layer was dried over MgSO$_4$, filtered, and concentrated in vacuo. The crude product 4 was dried under high vacuum and used without further purification. (5.1 g, 99%)

Preparation Example 5-bromo-2-chloro-3-(4-propoxybenzyl)thiophene (5)

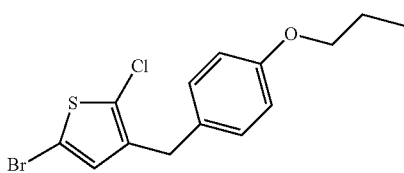 [SMILES: CCCOc1ccc(Cc2cc(Br)sc2Cl)cc1]

To a solution of phenol 4 (500 mg, 1.65 mmol) in acetone (25 mL) were added 1-iodopropane (0.5 mL, 4.95 mmol) and Cs$_2$CO$_3$ (460 mg, 4.95 mmol) at room temperature. The mixture was stirred at 60° C. for 12 hours. The reaction mixture was cooled to room temperature and filtered off through celite. The filtrate was concentrated in vacuo. The residue was purified by silica column chromatography (Biotage) to provide the title compound 5 (600 mg, 99%).

$^1$H NMR (400 MHz, CDCl$_3$) δ 7.06 (d, J=8.0 Hz, 2H), 6.84 (d, J=8.0 Hz, 2H), 6.66 (s, 1H), 3.89 (t, J=6.8 Hz, 2H), 3.79 (s, 2H), 1.79 (sextet, J=7.2 Hz, 2H), 1.03 (t, J=7.2 Hz, 3H).

Preparation Example 5-bromo-2-chloro-3-(4-isopropoxybenzyl)thiophene (6)

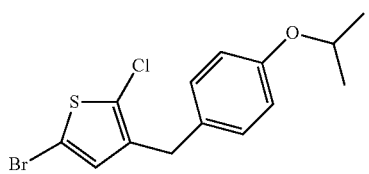 [SMILES: CC(C)Oc1ccc(Cc2cc(Br)sc2Cl)cc1]

To a solution of phenol 4 (1 g, 3.29 mmol) and PPh$_3$ (1.8 g, 6.58 mmol) in THF (25 mL) was added DIAD (1.3 mL, 6.58 mmol) at room temperature. The mixture was stirred at room temperature for 30 min. 2-Propanol (0.4 mL, 4.94 mmol) was added to the reaction mixture. The reaction mixture was stirred at room temperature for 20 hours. The mixture was extracted with EtOAc/H$_2$O (50 mL/50 mL) and was dried over MgSO$_4$, filtered, and concentrated in vacuo. The residue was purified by silica column chromatography (Biotage) to provide the desired product 6 (913 mg, 80%).

$^1$H NMR (400 MHz, CDCl$_3$) δ 7.06 (d, J=8.4 Hz, 2H), 6.81 (d, J=8.4 Hz, 2H), 6.67 (s, 1H), 4.54-4.47 (m, 1H), 3.79 (s, 2H), 1.38 (d, J=6.0 Hz, 6H).

Preparation Example 5-bromo-2-methylthiophene-3-carboxylic acid (8)

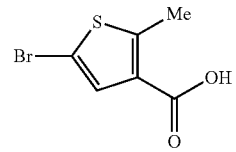

To a solution of 2-methylthiophene-3-carboxylic acid (2.44 g, 17.2 mmol, prepared from commercially available thiophene-3-carboxylic acid according to the known procedure (U.S. Pat. No. 5,840,917 A1)) was added pyridium tribromide (6.3 g) in AcOH (30 mL) at room temperature. The mixture was stirred at 40° C. for 4 hours. The mixture was cooled to room temperature and poured into H$_2$O (350 mL) with stirring. The product was precipitated and the suspension was stirred at room temperature for 1 hour. The precipitated solid was filtered, washed with H$_2$O (500 mL) and dried under high vacuum at 45° C. The crude product was used without further purification (3.18 g, 84%).

$^1$H NMR (400 MHz, CDCl$_3$) δ 7.38 (s, 1H), 2.70 (s, 3H); MH+ 221.

Preparation Example (5-bromo-2-methylthiophen-3-yl)(4-methoxyphenyl)methanone (9)

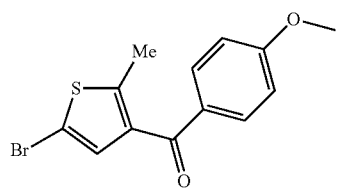 [SMILES: COc1ccc(C(=O)c2cc(Br)sc2C)cc1]

To a solution of acid 8 (10 g, 45.2 mmol) in CH$_2$Cl$_2$ (200 mL) were added oxalyl chloride (4.8 mL, 54.3 mmol) and catalytic amounts of DMF at room temperature. The mixture was stirred at room temperature for 2 hours. The mixture was concentrated in vacuo and dried under high vacuum. The crude acid chloride was dissolved with CH$_2$Cl$_2$ (200 mL) and cooled to 0° C. To the mixture was added anisole (5.0 mL, 45.2 mmol) at 0° C. and stirred at 0° C. for 5 min. To the reaction mixture was added AlCl$_3$ (6.0 g, 45.2 mmol) portionwise at 0° C. The mixture was stirred at 0° C. for 2 hours, warmed up to room temperature and stirred at room temperature for 15 hours. The mixture was poured into ice-water and extracted with CH$_2$Cl$_2$ (100 mL×2). The combined organic layer was dried over MgSO$_4$, filtered, and concentrated in vacuo. The crude product was triturated with MeOH (100 mL) and stirred at 0° C. for 1 hour. The precipitated solid was filtered and washed with MeOH (50 mL). The solid was dried under high vacuum and used without further purification (11.7 g, 83%).

$^1$H NMR (400 MHz, CDCl$_3$) δ 7.78 (d, J=6.8 Hz, 2H), 7.26 (s, 1H), 6.95 (d, J=6.8 Hz, 2H), 3.88 (s, 3H), 2.53 (s, 3H); MH+ 311.

Preparation Example 5-bromo-3-(4-methoxybenzyl)-2-methylthiophene (10)

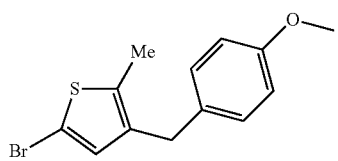 [SMILES: COc1ccc(Cc2cc(Br)sc2C)cc1]

To a solution of methanone 9 (11.7 g, 37.6 mmol) in CH$_2$Cl$_2$/CH$_3$CN (90 mL/90 mL) were added triethylsilane (15.0 mL, 94.0 mmol) and boron trifluoride diethyl etherate (12.0 mL, 94.0 mmol) at 0° C. The mixture was warmed up to room temperature slowly and stirred at room temperature for 15 hours. To the mixture was added aq. saturated K$_2$CO$_3$ solution (100 mL) slowly and extracted with EtOAc (100 mL×2). The combined organic layer was dried over MgSO$_4$, filtered, and concentrated in vacuo. The residue was purified by silica column chromatography (Biotage) to provide the desired product 10 (11.2 g, 100%).

$^1$H NMR (400 MHz, CDCl$_3$) δ 7.03 (d, J=8.8 Hz, 2H), 6.83 (d, J=8.8 Hz, 2H), 3.78 (s, 3H), 3.74 (s, 2H), 2.31 (s, 2H).

Preparation Example 5-iodo-3-(4-methoxybenzyl)-2-methylthiophene (11)

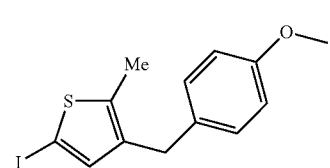 [SMILES: COc1ccc(Cc2cc(I)sc2C)cc1]

To a solution of bromide 10 (1.5 g, 5.05 mmol) in 1.4-dioxane (10 mL) were added NaI (1.5 g, 10.1 mmol), CuI (0.1 g, 0.51 mmol) and N$^1$,N$^2$-dimethylethane-1,2-diamine (0.11 mL, 1.01 mmol) at room temperature. The reaction mixture was evacuated and backfilled with nitrogen. The mixture was stirred 120° C. for 18 hours. The mixture was cooled to room temperature and filtered off through celite. The filtrate was extracted with EtOAc/H$_2$O (50 mL/50 mL). The organic layer was dried over MgSO$_4$, filtered, and concentrated in vacuo. The crude product 11 was dried under high vacuum and used without further purification (2.32 g, 79%).

Preparation Example 4-((5-bromo-2-methylthiophen-3-yl)methyl)phenol (12)

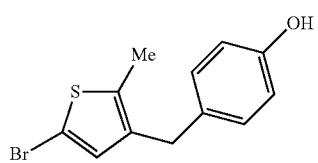 [SMILES: Cc1sc(Br)cc1Cc1ccc(O)cc1]

To a solution of bromide 10 (9.7 g, 32.6 mmol) in CH$_2$Cl$_2$ (100 mL) was added boron tribromide (40 mL, 39.2 mmol, 1M in CH$_2$Cl$_2$) dropwise at 0° C. The mixture was warmed up to room temperature slowly and stirred at room temperature for 3 hours. To the mixture was added aq. 1N HCl solution (200 mL) dropwise at 0° C. The mixture was extracted with CH$_2$Cl$_2$ (150 mL×2). The combined organic layer was dried over MgSO$_4$, filtered, and concentrated in vacuo. The residue was purified by silica column chromatography (Biotage) to provide the desired product 12 (5.64 g, 61%).

$^1$H NMR (400 MHz, CDCl$_3$) δ 6.99 (d, J=6.0 Hz, 2H), 6.75 (d, J=6.0 Hz, 1H), 6.65 (s, 1H), 4.73 (s, 1H), 3.73 (s, 2H), 2.31 (s, 3H).

Preparation Example 3-(4-(allyloxy)benzyl)-5-bromo-2-methylthiophene (13)

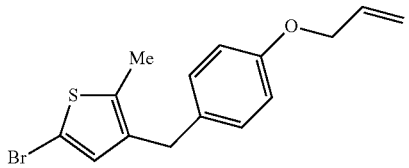 [SMILES: C=CCOc1ccc(Cc2cc(Br)sc2C)cc1]

To a solution of phenol 12 (860 mg, 3.04 mmol) in acetone (20 mL) were added allyl bromide (0.5 mL, 4.56 mmol) and Cs$_2$CO$_3$ (2.0 g, 6.08 mmol) at room temperature. The mixture was stirred at 60° C. for 2 hours. The reaction mixture was cooled to room temperature and filtered off through celite. The filtrate was concentrated in vacuo. The residue was purified by silica column chromatography (Biotage) to provide the title compound 13 (906 mg, 92%).

$^1$H NMR (400 MHz, CDCl$_3$) δ 7.07 (d, J=8.4 Hz, 2H), 6.85 (d, J=8.4 Hz, 2H), 6.19-5.99 (m, 1H), 5.40 (doublet and doublet, J=17.2, 1.6 Hz, 1H), 5.27 (doublet and doublet, J=10.8, 1.2 Hz, 1H), 4.51 (d, J=5.2 Hz, 2H), 3.80 (s, 2H), 2.31 (s, 3H).

Preparation Example 5-iodo-3-(4-methoxybenzyl)-2-methylthiophene (14)

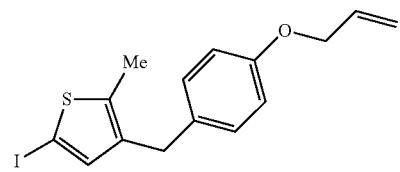 [SMILES: C=CCOc1ccc(Cc2cc(I)sc2C)cc1]

To a solution of bromide 13 (906 mg, 2.80 mmol) in 1,4-dioxane (10 mL) were added NaI (841 mg, 5.61 mmol), CuI (54 mg, 0.28 mmol) and $N^1,N^2$-dimethylethane-1,2-diamine (0.06 mL, 0.56 mmol) at room temperature. The reaction mixture was evacuated and backfilled with nitrogen. The mixture was stirred 120° C. for 18 hours. The mixture was cooled to room temperature and filtered off through celite. The filtrate was extracted with EtOAc/H$_2$O (50 mL/50 mL). The organic layer was dried over MgSO$_4$, filtered, and concentrated in vacuo. The crude product 14 was dried under high vacuum and used without further purification (846 mg, 81%).

Preparation Example (3R,4S,5R,6R)-2-(5-chloro-4-(4-methoxybenzyl)thiophen-2-yl)-3,4,5-tris(trimethylsilyloxy)-6-((trimethylsilyloxy)methyl)-tetrahydro-2H-pyran-2-ol (15)

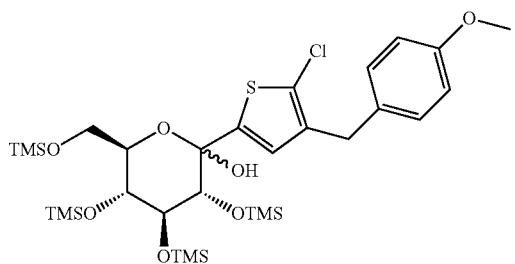

To a solution of bromide 3 (2.09 g, 5.06 mmol) in toluene/THF (30 mL/15 mL) at −78° C. under an atmosphere of nitrogen was added dropwise n-butyllithium (2.5 M in hexanes, 2.6 mL, 6.58 mmol), and the mixture was stirred for 40 min at the same temperature. Then a solution of TMS-protected gluconolactone (2.4 g, 6.58 mmol) in toluene (20 mL) was added dropwise, and the mixture was stirred for 1 hour at the same temperature. The reaction mixture was quenched by addition of saturated ammonium chloride. After complete addition, the solution was gradually raised to room temperature. The organic layer was separated and the aqueous layer was extracted with EtOAc. The combined organic layers were washed with brine, dried over anhydrous MgSO$_4$, filtered and concentrated in vacuo to yield the title compound 15, which was carried on to the next step without further purification.

Preparation Example (3R,4S,5R,6R)-2-(4-(4-methoxybenzyl)-5-methylthiophen-2-yl)-3,4,5-tris(trimethylsilyloxy)-6-((trimethylsilyloxy)methyl)-tetrahydro-2H-pyran-2-ol (16)

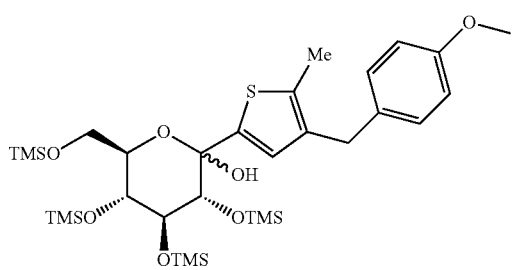

A mixture of TMS-protected gluconolactone (2.6 g, 5.47 mmol) and iodide 11 (1.57 g, 4.56 mmol) in THF (30 mL) was added trimethylsilylmethyl lithium (1.0 M in pentane, 9.6 mL, 9.58 mmol) at −65° C. The mixture was allowed to slowly warm to −45° C. over 2 hours. To a mixture was added aq. saturated NaHCO$_3$ solution to quench the reaction. After dilution with water, the mixture was stirred at room temperature for 30 min and extracted with EtOAc. The organic layer was dried over anhydrous MgSO$_4$, filtered and concentrated in vacuo. The crude title compound 16 was carried on to the next step without further purification.

Preparation Example (2R,3R,4S,5R,6R)-2-(acetoxymethyl)-6-(5-chloro-4-(4-methoxybenzyl)thiophen-2-yl)-tetrahydro-2H-pyran-3,4,5-triyl triacetate (19)

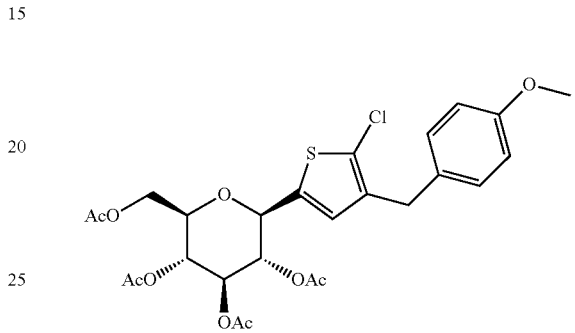

Step 1)

To a solution of crude alcohol 15 (3.57 g, 5.06 mmol) in THF (50 mL) were added CH$_3$SO$_3$H (0.6N in MeOH, 17 mL, 10.1 mmol) at −78° C. The mixture was allowed to slowly warm to −40° C. To a mixture was added aq. saturated NaHCO$_3$ solution (50 mL) to quench the reaction. After dilution with water, the mixture was stirred at room temperature for 30 min and extracted with EtOAc (100 mL). The organic layer was dried over anhydrous MgSO$_4$, filtered and concentrated in vacuo. The crude (3R,4S,5S,6R)-2-(5-chloro-4-(4-methoxybenzyl)thiophen-2-yl)-6-(hydroxymethyl)-2-methoxy-tetrahydro-2H-pyran-3,4,5-triol 17 (2.43 g) was carried on to the next step without further purification.

Step 2)

To a solution of compound 17 (2.43 g) in CH$_2$Cl$_2$/CH$_3$CN (25 mL/25 mL) were added triethylsilane (1.8 mL, 11.3 mmol) and boron trifluoride diethyl etherate (1.5 mL, 11.3 mmol) at −60° C. The mixture was allowed to slowly warm to −5° C. To a mixture was added aq. saturated NaHCO$_3$ solution (20 mL) to quench the reaction and extracted with EtOAc (100 mL). The combined organic layer was dried over MgSO$_4$, filtered, and concentrated in vacuo. The crude (3R,4S,5S,6R)-2-(5-chloro-4-(4-methoxybenzyl)thiophen-2-yl)-6-(hydroxymethyl)-2-methoxy-tetrahydro-2H-pyran-3,4,5-triol 18 (2.17 g) was carried on to the next step without further purification.

Step 3)

To a solution of compound 18 (2.17 g) in CH$_2$Cl$_2$ (50 mL) were added Ac$_2$O (5.1 mL, 54.1 mmol), Et$_3$N (7.5 mL, 54.1 mmol) and catalytic amount of DMAP at 0° C. The mixture was stirred at 0° C. for 15 min and at room temperature for 15 hours. The mixture was concentrated under reduced pressure to remove volatiles. The residue was diluted with EtOAc (50 mL), washed with H$_2$O (100 mL), aq. 1N HCl solution (100 mL) and brine (100 mL) successively. The organic layer was dried over MgSO$_4$, filtered, and concentrated in vacuo. The residue was purified by silica column chromatography (Biotage) to provide the mixture of anomers of the title compound 19 (1.9 g). The anomeric mixture of 19 was recrystallized with EtOH (50 mL). The precipitate was collected by filtration and washed with cold EtOH (30 mL) and dried under high vacuum to obtain the title compound 19 (1.37 g, 48% (5-steps)).

$^1$H NMR (400 MHz, CDCl$_3$) δ 7.05 (d, J=8.8 Hz, 2H), 7.82 (d, J=8.8 Hz, 2H), 6.57 (s, 1H), 5.27-5.12 (m, 2H), 5.04 (t, J=9.6 Hz, 1H), 4.50 (d, J=9.6 Hz, 1H), 4.27-4.13 (m, 2H), 3.83-3.71 (m, 6H), 2.08 (s, 3H), 2.03 (s, 3H), 1.99 (s, 3H), 1.78 (s, 3H); M+Na+ 591.

Preparation Example (2R,3R,4S,5S,6R)-2-(5-chloro-4-(4-methoxybenzyl)thiophen-2-yl)-6-(hydroxymethyl)-tetrahydro-2H-pyran-3,4,5-triol (20)

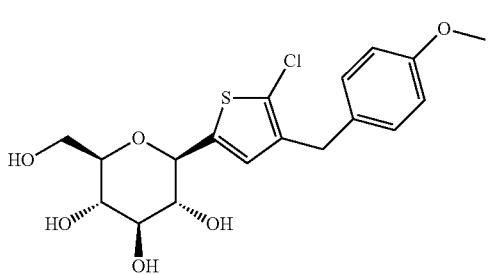 [SMILES: COc1ccc(Cc2cc([C@@H]3O[C@H](CO)[C@@H](O)[C@H](O)[C@H]3O)sc2Cl)cc1]

To a suspension of acetate 19 (1.37 g, 2.41 mmol) in MeOH (20 mL) was added NaOMe (25 wt % in MeOH, 0.3 mL) at room temperature. The mixture was stirred at room temperature for 1 hour. Glacial AcOH was added to the mixture to acidify the mixture. The mixture was concentrated under reduced pressure. The residue was purified by prep HPLC (C18) to provide the title compound 20 (604 mg, 63%).

$^1$H NMR (400 MHz, DMSO-d$_6$) δ 7.13 (d, J=8.4 Hz, 2H), 6.86 (d, J=8.4 Hz, 2H), 6.82 (s, 1H), 5.18 (d, J=6.0 Hz, 1H), 4.99 (d, J=5.2 Hz, 1H), 4.94 (d, J=5.6 Hz, 1H), 4.46 (t, J=6.0 Hz, 1H), 4.17 (d, J=9.2 Hz, 1H), 3.77 (s, 2H), 3.73-3.63 (m, 4H), 3.40 (quintet, J=6.0 Hz, 1H), 3.27-3.16 (m, 2H), 3.11-3.01 (m, 2H); M+Na+ 423.

Preparation Example (4-((5-bromo-2-chlorothiophen-3-yl)methyl)phenoxy)(tert-butyl)dimethylsilane (21)

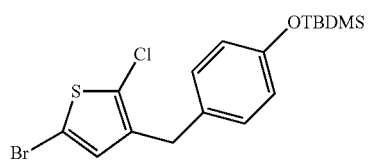 [SMILES: CC(C)(C)[Si](C)(C)Oc1ccc(Cc2cc(Br)sc2Cl)cc1]

To a solution of phenol 4 (3.0 g, 9.88 mmol) in DMF (20 mL) were added TBDMSCl (1M in CH$_2$Cl$_2$, 20 mL, 19.8 mmol), imidazole (2.1 g, 29.6 mmol) and DMAP (0.25 g, 1.98 mmol) at room temperature. The mixture was stirred at ambient temperature for 14 hours. The mixture was extracted with EtOAc/H$_2$O (75 mL/250 mL). The organic layer was dried over MgSO$_4$, filtered, and concentrated in vacuo. The residue was purified by silica column chromatography (Biotage) to provide the title compound 21 (4.12 g, 99%).

$^1$H NMR (400 MHz, CDCl$_3$) δ 6.99-6.91 (m, 2H), 6.83 (s, 1H), 6.81-6.72 (m, 2H), 3.64 (s, 2H), 0.96 (s, 9H), 0.15 (s, 6H).

Preparation Example (3R,4S,5R,6R)-2-(4-(4-(tert-butyldimethylsilyloxy)benzyl)-5-chlorothiophen-2-yl)-3,4,5-tris(trimethylsilyloxy)-6-((trimethylsilyloxy)methyl)-tetrahydro-2H-pyran-2-ol (22)

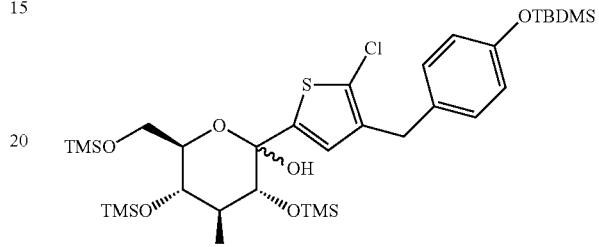

To a solution of bromide 21 (4.12 g, 9.86 mmol) in toluene/THF (40 mL/20 mL) at −78° C. under an atmosphere of nitrogen was added dropwise n-butyllithium (2.5 M in hexanes, 4.0 mL, 9.86 mmol), and the mixture was stirred for 45 min at the same temperature. Then a solution of TMS-protected gluconolactone (3.8 g, 8.22 mmol) in toluene (20 mL) was added dropwise, and the mixture was stirred for 1 hour at the same temperature. The reaction mixture was quenched by addition of saturated ammonium chloride. After complete addition, the solution was gradually raised to room temperature. The organic layer was separated and the aqueous layer was extracted with EtOAc. The combined organic layers were washed with brine, dried over anhydrous MgSO$_4$, filtered and concentrated in vacuo to yield the title compound 22, which was carried on to the next step without further purification.

Preparation Example 4-((5-iodo-2-methylthiophen-3-yl)methyl)phenol (23)

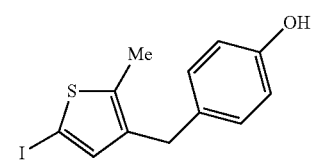 [SMILES: Cc1sc(I)cc1Cc1ccc(O)cc1]

To a solution of bromide 12 (960 mg, 3.39 mmol) in 1.4-dioxane (10 mL) were added NaI (1.1 g, 6.78 mmol), CuI (100 mg, 0.34 mmol) and N$^1$,N$^2$-dimethylethane-1,2-diamine (0.1 mL, 0.68 mmol) at room temperature. The reaction mixture was evacuated and backfilled with nitrogen. The mixture was stirred 120° C. for 18 hours. The mixture was cooled to room temperature and filtered off through celite. The filtrate was extracted with EtOAc/H$_2$O (50 mL/50 mL). The organic layer was dried over MgSO$_4$, filtered, and concentrated in vacuo. The crude product 23 was dried under high vacuum and used without further purification (540 mg, 48%).

Preparation Example tert-butyl(4-((5-iodo-2-methylthiophen-3-yl)methyl)phenoxy)dimethylsilane (24)

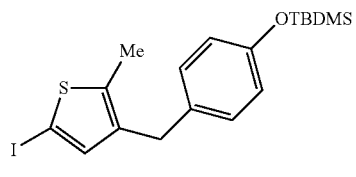 [SMILES: Cc1sc(I)cc1Cc1ccc(O[Si](C)(C)C(C)(C)C)cc1]

To a solution of phenol 23 (0.54 g, 1.64 mmol) in DMF (15 mL) were added TBDMSCl (1M in CH$_2$Cl$_2$, 3.5 mL, 3.28 mmol), imidazole (0.35 g, 4.92 mmol) and DMAP (50 mg, 0.33 mmol) at room temperature. The mixture was stirred at ambient temperature for 15 hours. The mixture was extracted with EtOAc/H$_2$O (50 mL/150 mL). The organic layer was dried over MgSO$_4$, filtered, and concentrated in vacuo. The residue was purified by silica column chromatography (Biotage) to provide the title compound 24 (0.65 g, 89%).

$^1$H NMR (400 MHz, CDCl$_3$) δ 7.00-6.91 (m, 2H), 6.83 (s, 1H), 6.77-6.71 (m, 2H), 3.75 (s, 2H), 2.34 (s, 3H), 0.97 (s, 9H), 0.17 (s, 6H).

Preparation Example (3R,4S,5R,6R)-2-(4-(4-(tert-butyldimethylsilyloxy)benzyl)-5-methylthiophen-2-yl)-3,4,5-tris(trimethylsilyloxy)-6-((trimethylsilyloxy)methyl)-tetrahydro-2H-pyran-2-ol (25)

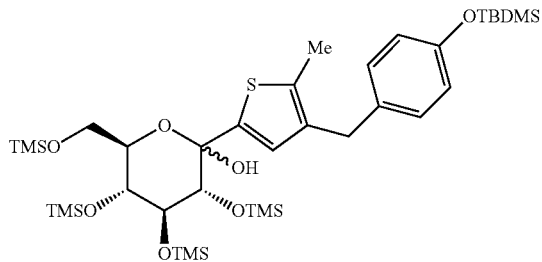

A mixture of TMS-protected gluconolactone (0.65 g, 1.46 mmol) and iodide 24 (0.82 g, 1.75 mmol) in THF (20 mL) was added trimethylsilylmethyl lithium (1.0 M in pentane, 3.1 mL, 3.07 mmol) at −65° C. The mixture was allowed to slowly warm to −45° C. over 1 hour. To a mixture was added aq. saturated NaHCO$_3$ solution to quench the reaction. After dilution with water, the mixture was stirred at room temperature for 30 min and extracted with EtOAc. The organic layer was dried over anhydrous MgSO$_4$, filtered and concentrated in vacuo. The crude title compound 25 was carried on to the next step without further purification.

Preparation Example (2R,3R,4S,5R,6R)-2-(4-(4-acetoxybenzyl)-5-chlorothiophen-2-yl)-6-(acetoxymethyl)-tetrahydro-2H-pyran-3,4,5-triyl triacetate (28)

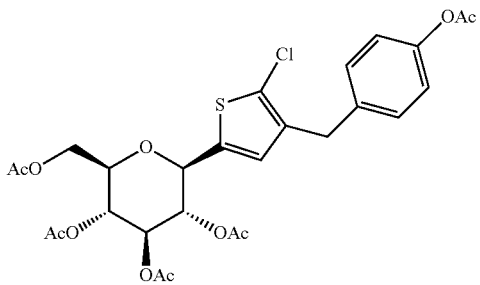 [SMILES: CC(=O)OC[C@H]1O[C@@H](c2cc(Cc3ccc(OC(C)=O)cc3)c(Cl)s2)[C@H](OC(C)=O)[C@@H](OC(C)=O)[C@@H]1OC(C)=O]

Step 1)
To a solution of crude alcohol 22 (1.51 g, 1.88 mmol) in THF (50 mL) were added CH$_3$SO$_3$H (0.6N in MeOH, 6.3 mL, 3.76 mmol) at −78° C. The mixture was allowed to slowly warm to −40° C. To a mixture was added aq. saturated NaHCO$_3$ solution (50 mL) to quench the reaction. After dilution with water, the mixture was stirred at room temperature for 30 min and extracted with EtOAc (100 mL). The organic layer was dried over anhydrous MgSO$_4$, filtered and concentrated in vacuo. The crude (3R,4S,5S,6R)-2-(5-chloro-4-(4-hydroxybenzyl)thiophen-2-yl)-6-(hydroxymethyl)-2-methoxy-tetrahydro-2H-pyran-3,4,5-triol 26 (1.1 g) was carried on to the next step without further purification.

Step 2)
To a solution of compound 26 (1.1 g) in CH$_2$Cl$_2$/CH$_3$CN (20 mL/20 mL) were added triethylsilane (0.70 mL, 4.14 mmol) and boron trifluoride diethyl etherate (0.55 mL, 4.14 mmol) at −60° C. The mixture was allowed to slowly warm to −5° C. To a mixture was added aq. saturated NaHCO$_3$ solution (25 mL) to quench the reaction and extracted with EtOAc (100 mL). The combined organic layer was dried over MgSO$_4$, filtered, and concentrated in vacuo. The crude (3R,4S,5S,6R)-2-(5-chloro-4-(4-hydroxybenzyl)thiophen-2-yl)-6-(hydroxymethyl)-tetrahydro-2H-pyran-3,4,5-triol 27 (0.85 g) was carried on to the next step without further purification.

Step 3)
To a solution of compound 27 (0.85 g) in CH$_2$Cl$_2$ (20 mL) were added Ac$_2$O (2.1 mL, 22.0 mmol), Et$_3$N (3.1 mL, 22.0 mmol) and catalytic amount of DMAP at 0° C. The mixture was stirred at 0° C. for 15 min and at room temperature for 12 hours. The mixture was concentrated under reduced pressure to remove volatiles. The residue was diluted with EtOAc (50 mL), washed with H$_2$O (100 mL), aq. 1N HCl solution (100 mL) and brine (100 mL) successively. The organic layer was dried over MgSO$_4$, filtered, and concentrated in vacuo. The residue was purified by silica column chromatography (Biotage) to provide the mixture of anomers of the title compound 28 (0.67 g). The anomeric mixture of 19 was recrystallized with EtOH (20 mL). The precipitate was collected by filtration and washed with cold EtOH (20 mL) and dried under high vacuum to obtain anomer of the title compound 28 (0.41 g, 33% (4-steps)).

$^1$H NMR (400 MHz, CDCl$_3$) δ 7.15 (d, J=8.4 Hz, 2H), 6.99 (d, J=8.4 Hz, 2H), 6.59 (s, 1H), 5.27-5.13 (m, 2H), 5.04 (d, J=9.6 Hz, 1H), 4.51 (d, J=10.0 Hz, 1H), 4.27-4.13 (m, 2H), 3.89-3.77 (m, 3H), 2.28 (s, 3H), 2.08 (s, 3H), 2.04 (s, 3H), 1.99 (s, 3H), 1.77 (s, 3H); M+Na+ 619.

Preparation Example (2R,3R,4S,5S,6R)-2-(5-chloro-4-(4-hydroxybenzyl)thiophen-2-yl)-6-(hydroxymethyl)-tetrahydro-2H-pyran-3,4,5-triol (29)

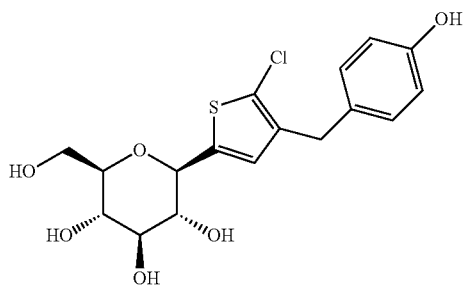 [SMILES: OC[C@H]1O[C@@H](c2cc(Cc3ccc(O)cc3)c(Cl)s2)[C@H](O)[C@@H](O)[C@@H]1O]

To a suspension of acetate 28 (413 mg, 0.617 mmol) in MeOH (15 mL) was added NaOMe (25 wt % in MeOH, 0.2 mL) at room temperature. The mixture was stirred at room temperature for 1 hour. Glacial AcOH was added to the mixture to acidify the mixture. The mixture was concentrated under reduced pressure. The residue was purified by prep HPLC (C18) to provide the title compound 29 (130 mg, 55%).

$^1$H NMR (400 MHz, DMSO-$d_6$) δ 7.00 (d, J=8.4 Hz, 2H), 6.81 (s, 1H), 6.67 (d, J=8.0 Hz, 2H), 5.19 (br s, 1H), 4.98 (br s, 2H), 4.47 (br s, 1H), 4.17 (d, J=9.2 Hz, 1H), 3.73-3.62 (m, 3H), 3.43-3.37 (m, 1H), 3.24-3.14 (m, 3H), 3.12-3.02 (m, 2H); M+Na+ 409.

Preparation Example (2R,3R,4S,5S,6R)-2-(5-chloro-4-(4-(prop-2-ynyloxy)benzyl)thiophen-2-yl)-6-(hydroxymethyl)-tetrahydro-2H-pyran-3,4,5-triol (30)

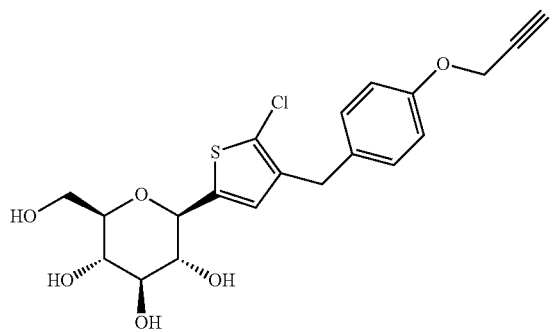 [SMILES: C#CCOc1ccc(Cc2cc([C@@H]3O[C@H](CO)[C@@H](O)[C@H](O)[C@H]3O)sc2Cl)cc1]

To a solution of phenol 29 (124 mg, 0.320 mmol) in acetone (10 mL) were added propargyl bromide (80 wt % in toluene, 1.7 g, 11.2 mmol) and Cs$_2$CO$_3$ (1.5 g, 11.2 mmol) at room temperature. The mixture was stirred at 50° C. for 20 hours. The reaction mixture was cooled to room temperature and filtered off through celite. The filtrate was concentrated in vacuo. The residue was purified by prep HPLC (C18) to provide the title compound 30 (51 mg, 38%).

$^1$H NMR (400 MHz, DMSO-$d_6$) δ 7.14 (d, J=8.8 Hz, 2H), 6.92 (d, J=8.8 Hz, 2H), 6.84 (s, 1H), 5.20 (d, J=5.6 Hz, 1H), 5.02 (d, J=4.8 Hz, 1H), 4.97 (d, J=5.2 Hz, 1H), 4.74 (d, J=2.4 Hz, 2H), 4.46 (d, J=5.6 Hz, 1H), 4.17 (d, J=9.2 Hz, 1H), 3.78 (s, 2H), 3.71-3.64 (m, 1H), 3.56-3.51 (m, 1H), 3.40 (quintet, J=6.0 Hz, 1H), 3.25-3.16 (m, 2H), 3.13-3.02 (m, 2H); M+Na+ 447.

Preparation Example (5-bromo-2-chlorothiophen-3-yl)methanol (31)

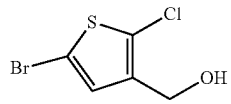

To a solution of acid 1 (3.0 g, 12.4 mmol) in THF (50 mL) were added borane dimethylsulfide complex (10M in THF, 3.2 mL, 31.1 mmol) at 0° C. The mixture was stirred at 0° C. for 15 min, at room temperature for 45 min, and at 65° C. for 2 hours. The reaction mixture was cooled to 0° C. To the mixture were added MeOH (30 mL), H$_2$O (250 mL) dropwise at 0° C. The mixture was extracted with EtOAc (100 mL). The organic layer was dried over MgSO$_4$, filtered, and concentrated in vacuo to obtain the title compound 31 (2.8 g, 99%). The crude alcohol 31 was carried on to the next step without further purification.

Preparation Example (5-bromo-2-chlorothiophen-3-yl)methoxy)triisopropylsilane (32)

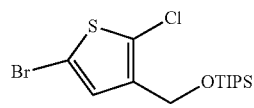

To a solution of alcohol 31 (2.8 g, 12.3 mmol) in DMF (25 mL) were added TIPSCl (5.3 mL, 24.6 mmol), imidazole (2.5 g, 36.9 mmol) and DMAP (0.3 g, 2.46 mmol) at room temperature. The mixture was stirred at ambient temperature for 14 hours. The mixture was extracted with EtOAc/H$_2$O (75 mL/250 mL). The organic layer was dried over MgSO$_4$, filtered, and concentrated in vacuo. The residue was purified by silica column chromatography (Biotage) to provide the title compound 32 (4.0 g, 85%).

$^1$H NMR (400 MHz, CDCl$_3$) δ 7.01 (s, 1H), 4.66 (s, 2H), 1.19-1.11 (m, 3H), 1.07 (d, J=9.2 Hz, 18H).

Preparation Example (3R,4S,5R,6R)-3,4,5-tris(benzyloxy)-6-(benzyloxymethyl)-2-(5-chloro-4-((triisopropylsilyloxy)methyl)thiophen-2-yl)-tetrahydro-2H-pyran-2-ol (33)

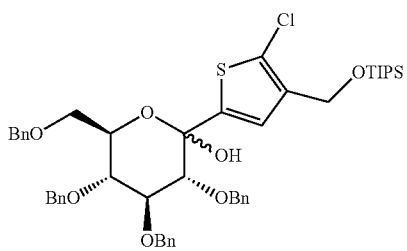

To a solution of bromide 32 (4.0 g, 5.06 mmol) in THF (40 mL) at −78° C. under an atmosphere of nitrogen was added dropwise n-butyllithium (2.5 M in hexanes, 4.2 mL, 10.5 mmol), and the mixture was stirred for 40 min at the same temperature. Then a solution of benzyl-protected gluconolactone (4.7 g, 8.75 mmol) in THF (20 mL) was added dropwise, and the mixture was stirred for 2.5 hours at the same temperature. The reaction mixture was quenched by addition of saturated ammonium chloride. After complete addition, the solution was gradually raised to room temperature. The organic layer was separated and the aqueous layer was extracted with EtOAc. The combined organic layers were washed with brine, dried over anhydrous MgSO₄, filtered and concentrated in vacuo to yield the title compound 33, which was carried on to the next step without further purification.

Preparation Example ((2-chloro-5-((3R,4S,5R,6R)-3,4,5-tris(benzyloxy)-6-(benzyloxymethyl)-tetrahydro-2H-pyran-2-yl)thiophen-3-yl)methoxy)triisopropylsilane (34)

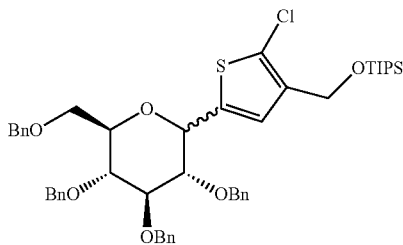

To a solution of alcohol 33 (8.53 g, 10.1 mmol) in CH₂Cl₂ (50 mL) were added triethylsilane (3.3 mL, 20.2 mmol) and boron trifluoride diethyl etherate (2.6 mL, 20.2 mmol) at −60° C. The mixture was allowed to slowly warm to −20° C. To a mixture was added aq. saturated K₂CO₃ solution (50 mL) to quench the reaction. The mixture was evaporated under reduced pressure to remove CH₂Cl₂ and extracted with EtOAc (100 mL). The combined organic layer was dried over MgSO₄, filtered, and concentrated in vacuo to yield the title compound 34 (8.22 g), which was carried on to the next step without further purification.

Preparation Example (2-chloro-5-((3R,4S,5R,6R)-3,4,5-tris(benzyloxy)-6-(benzyloxymethyl)-tetrahydro-2H-pyran-2-yl)thiophen-3-yl)methanol (35)

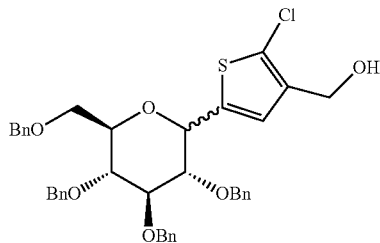 [SMILES: OCc1cc(C2O[C@H](COCc3ccccc3)[C@@H](OCc3ccccc3)[C@H](OCc3ccccc3)[C@H]2OCc2ccccc2)sc1Cl]

To a solution of compound 34 (8.22 g) in THF (50 mL) was added TBAF (1M in THF, 20 mL, 19.9 mmol) dropwise at 0° C. The mixture was stirred at room temperature for 2 hours. The mixture was extracted with EtOAc/H₂O (100 mL/250 mL). The organic layer was dried over MgSO₄, filtered, and concentrated in vacuo. The residue was purified by silica column chromatography (Biotage) to provide the title compound 35 (5.2 g, 89% (3-steps)).
M+Na+ 693.

Preparation Example (2-chloro-5-((2R,3R,4S,5R,6R)-3,4,5-tris(benzyloxy)-6-(benzyloxymethyl)-tetrahydro-2H-pyran-2-yl)thiophen-3-yl)methyl benzoate (36)

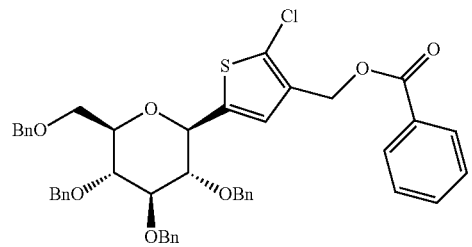 [SMILES: O=C(OCc1cc([C@@H]2O[C@H](COCc3ccccc3)[C@@H](OCc3ccccc3)[C@H](OCc3ccccc3)[C@H]2OCc2ccccc2)sc1Cl)c1ccccc1]

To a solution of alcohol 35 (5.2 g, 7.75 mmol) in CH₂Cl₂ (50 mL) were added Et₃N (3.5 mL, 23.3 mmol) and benzoyl chloride (1.2 mL, 10.1 mmol) at 0° C. The mixture was allowed to slowly warm to room temperature and stirred at room temperature for 15 hours. The mixture was washed with aq. saturated NaHCO₃ solution. The organic layer was dried over MgSO₄, filtered, and concentrated in vacuo. The residue was purified by silica column chromatography (Biotage) to provide the mixture of anomers of the title compound (6.1 g). The anomeric mixture of 36 was recrystallized with EtOH (50 mL). The precipitate was collected by filtration and washed with cold EtOH (30 mL) and dried under high vacuum to obtain β-anomer of the title compound 36 (4.64 g, 77%).
¹H NMR (400 MHz, CDCl₃) δ 8.01 (d, J=8.4 Hz, 2H), 7.58-7.52 (m, 1H), 7.44-7.36 (m, 2H), 7.35-7.24 (m, 13H), 7.21-7.11 (m, 5H), 7.08-7.01 (m, 3H), 5.27 (s, 2H), 4.94 (s, 2H), 4.67-4.53 (m, 3H), 4.42 (d, J=9.2 Hz, 1H), 4.24 (d, J=10.4 Hz, 1H), 3.81-3.69 (m, 4H), 3.62-3.52 (m, 1H), 3.50-3.42 (m, 1H); M+Na+ 797.

Preparation Example (2-chloro-5-((2R,3R,4S,5R,6R)-3,4,5-tris(benzyloxy)-6-(benzyloxymethyl)-tetrahydro-2H-pyran-2-yl)thiophen-3-yl)methanol (37)

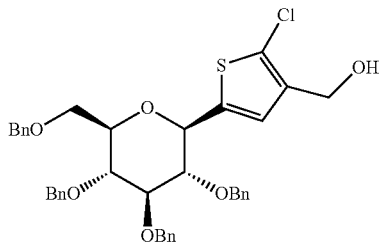 [SMILES: OCc1cc([C@@H]2O[C@H](COCc3ccccc3)[C@@H](OCc3ccccc3)[C@H](OCc3ccccc3)[C@H]2OCc2ccccc2)sc1Cl]

To a solution of benzoate 36 (4.5 g, 5.80 mmol) in THF/MeOH/H₂O (30 mL/10 mL/10 mL) was added LiOH monohydrate (0.73 g, 17.4 mmol) at room temperature. The mixture was stirred at room temperature for 5 hours. The mixture was extracted with EtOAc/aq. saturated NH₄Cl solution (100 mL/100 mL). The organic layer was dried over anhydrous MgSO₄, filtered and concentrated in vacuo to yield the title compound 37 (3.86 g, 99%), which was carried on to the next step without further purification.

¹H NMR (400 MHz, CDCl₃) δ 7.38-7.22 (m, 17H), 7.21-7.15 (m, 2H), 7.13-7.05 (m, 2H), 6.98 (s, 1H), 4.94-4.82 (m, 3H), 4.69-4.62 (m, 3H), 4.59-4.52 (m, 3H), 4.40 (d, J=9.2 Hz, 1H), 4.22 (d, J=7.2 Hz, 1H), 3.80-3.68 (m, 4H), 3.62-3.55 (m, 1H), 3.46 (t, J=8.8 Hz, 1H); M+Na+ 693.

Preparation Example (2R,3R,4S,5R,6R)-3,4,5-tris(benzyloxy)-2-(benzyloxymethyl)-6-(4-(bromomethyl)-5-chlorothiophen-2-yl)-tetrahydro-2H-pyran (38)

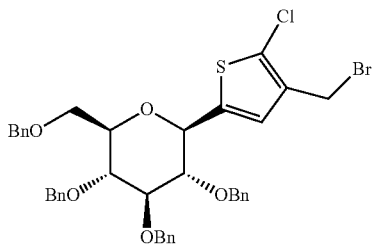 [SMILES: Clc1sc([C@@H]2O[C@H](COCc3ccccc3)[C@@H](OCc3ccccc3)[C@H](OCc3ccccc3)[C@H]2OCc2ccccc2)cc1CBr]

To a solution of alcohol 37 (3.86 g, 5.75 mmol) in ether (50 mL) were added phosphorus tribromide (0.3 mL, 2.88 mmol) and catalytic amount of pyridine at 0° C. The mixture was allowed to warm to room temperature and stirred at room temperature for 2 hours. The mixture was extracted with EtOAc/H₂O (100 mL/150 mL). The organic layer was dried over MgSO₄, filtered, and concentrated in vacuo. The organic layer was dried over anhydrous MgSO₄, filtered and concentrated in vacuo to yield the title compound 38 (4.1 g, 97%), which was carried on to the next step without further purification.

Preparation Example (2R,3R,4S,5R,6R)-3,4,5-tris(benzyloxy)-2-(benzyloxymethyl)-6-(5-chloro-4-(4-methylbenzyl)thiophen-2-yl)-tetrahydro-2H-pyran (39)

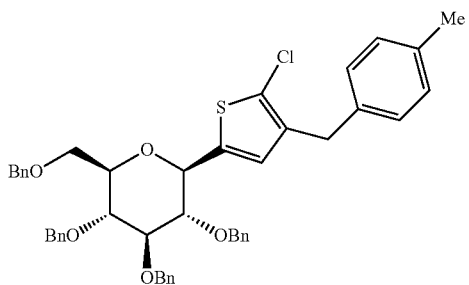 [SMILES: Cc1ccc(Cc2cc([C@@H]3O[C@H](COCc4ccccc4)[C@@H](OCc4ccccc4)[C@H](OCc4ccccc4)[C@H]3OCc3ccccc3)sc2Cl)cc1]

To a solution of bromide 38 (850 mg, 1.16 mmol) in toluene/EtOH (18 mL/2 mL) were added 4-methylphenylboronic acid (200 mg, 1.39 mmol), tetrakis(triphenylphosphin)palladium (70 mg, 0.058 mmol) and Cs₂CO₃ (770 mg, 2.32 mmol) at room temperature. The mixture was stirred at 120° C. The mixture was cooled to room temperature and filtered off thorough silica gel to remove insoluble materials. The filtrate was ure was extracted with EtOAc/H₂O (100 mL/150 mL). The organic layer was dried over MgSO₄, filtered, and concentrated in vacuo. The residue was purified by silica column chromatography (Biotage) to provide the title compound 39 (611 mg, 71%).

M+Na+ 767.

Preparation Example (2R,3R,4S,5R,6R)-2-(acetoxymethyl)-6-(5-chloro-4-(4-methylbenzyl)thiophen-2-yl)-tetrahydro-2H-pyran-3,4,5-triyl triacetate (40)

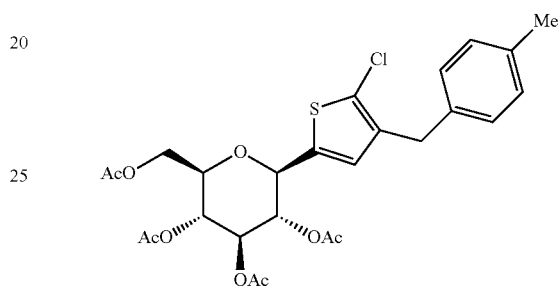

To a solution of compound 39 (611 mg, 0.819 mmol) in acetic anhydride (15 mL) was added TMSOTf (1.2 mL, 6.55 mmol) at −30° C. The mixture was allowed to slowly warm to room temperature and stirred at room temperature for 2 hours. The mixture was cooled to 0° C. and aq. saturated NaHCO₃ solution (50 mL) was added to the mixture at 0° C. to quench the reaction. The mixture was diluted with EtOAc (50 mL) and washed with aq. saturated NaHCO₃ solution (50 mL×3). The organic layer was dried over MgSO₄, filtered, and concentrated in vacuo. The residue was purified by silica column chromatography (Biotage) to provide the title compound 40 (339 mg, 75%).

M+Na+ 575.

Preparation Example (2R,3R,4S,5S,6R)-2-(5-chloro-4-(4-methylbenzyl)thiophen-2-yl)-6-(hydroxymethyl)-tetrahydro-2H-pyran-3,4,5-triol (41)

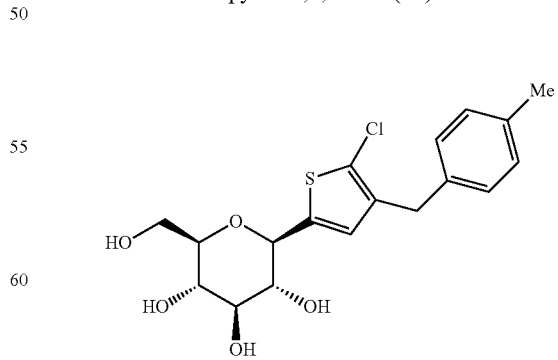

To a suspension of acetate 40 (339 mg, 0.612 mmol) in MeOH (15 mL) was added NaOMe (25 wt % in MeOH, 0.2 mL) at room temperature. The mixture was stirred at room temperature for 1 hour. Glacial AcOH was added to the mixture to acidify the mixture. The mixture was concentrated under reduced pressure. The residue was purified by prep HPLC (C18) to provide the title compound 41 (55 mg, 23%).

$^1$H NMR (400 MHz, DMSO-$d_6$) δ 7.10 (s, 4H), 6.82 (s, 1H), 5.19 (d, J=5.6 Hz, 1H), 5.00 (d, J=4.8 Hz, 1H), 4.95 (d, J=5.2 Hz, 1H), 4.46 (t, J=5.6 Hz, 1H), 4.17 (d, J=9.2 Hz, 1H), 3.79 (s, 2H), 3.60-3.51 (m, 1H), 3.40 (quintet, J=6.0 Hz, 1H), 3.25-3.16 (m, 2H), 3.11-3.02 (m, 2H), 2.25 (s, 3H); M+Na+ 407.

Preparation Example

N-Methoxy-N,3-dimethylthiophene-2-carboxamide (43)

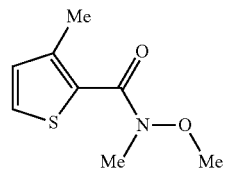 [SMILES: CON(C)C(=O)c1sccc1C]

To a mixture of N,O-dimethylhydroylamine hydrochloride (5.85 g, 60 mmol) and TEA (16.7 mL, 120 mmol) in chloroform was added 3-methylthiophene-2-carbonyl chloride (42, 4.89 mL, 40 mmol) at 0° C. Then, the reaction temperature was raised to room temperature, and maintained for overnight. The reaction mixture was subsequently washed with a HCl solution (1M, 50 mL) and brine. The organic phase was dried MgSO$_4$ and evaporated under vacuum to provide the title compound 43 (7.47 g, ~100%) as a yellow oil, which was used without further purification.

$^1$H NMR (400 MHz, CDCl$_3$) δ 7.37 (d, J=5.2 Hz, 1H), 6.90 (d, J=5.2 Hz, 1H), 3.71 (s, 3H), 3.34 (s, 3H), 2.55 (s, 3H); MH+ 186.

Preparation Example (3-Methylthiophen-2-yl)(4-propylphenyl)methanone (44, Via Route a)

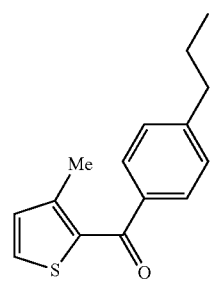 [SMILES: CCCc1ccc(C(=O)c2sccc2C)cc1]

To a solution of the Weinreb amide (3.78 g, 20.4 mmol) in anhydrous THF (61.3 mL) was added dropwise (over a 10-min period) a solution of n-4-propylphenylmagnesium bromide (81.6 mL, 0.5 M in THF) under nitrogen atmosphere at 0° C. The reaction mixture was allowed to warm to room temperature and stirred for 16 hours. The mixture was poured into a 1 M HCl solution (50 mL) and extracted with EtOAc (100 mL). The organic phase was subsequently washed with brine, dried over MgSO$_4$ and evaporated under vacuum. The residue was further purified by silica column chromatography (Biotage) to provide (3-methylthiophen-2-yl)(4-propylphenyl)methanone (44, 3.15 g, 12.9 mmol, 63%).

$^1$H NMR (400 MHz, CDCl$_3$) δ 7.76 (d, J=8.4 Hz, 2H), 7.47 (d, J=5.2 Hz, 1H), 7.27 (d, J=8.0 Hz, 2H), 7.00 (d, J=4.8 Hz, 1H), 2.66 (t, J=7.2 Hz, 2H), 2.48 (s, 3H), 1.73-1.64 (m, 2H), 0.96 (t, J=7.2 Hz, 3H); MH+ 245.

Preparation Example (5-Bromo-3-methylthiophen-2-yl)(4-propylphenyl)methanone (45)

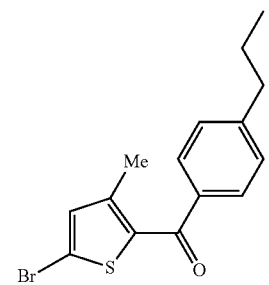 [SMILES: CCCc1ccc(C(=O)c2sc(Br)cc2C)cc1]

To a solution of (3-methylthiophen-2-yl)(4-propylphenyl)methanone (44, 1.12 g, 4.58 mmol) in acetic acid (4.67 mL) was added pyridinium tribromide (3.67 g, 11.5 mmol). The reaction mixture was heated to 50° C. for 3 hours. After cooling to room temperature, the mixture was poured into water (50 mL) and extracted with EtOAc (100 mL). The organic phase was dried over MgSO$_4$ and evaporated under vacuum. The residue was further purified by silica column chromatography (Biotage) to provide (5-bromo-3-methylthiophen-2-yl)(4-propylphenyl)methanone (45, 0.95 g, 2.95 mmol, 64%).

$^1$H NMR (400 MHz, CDCl$_3$) δ 7.72 (d, J=8.4 Hz, 2H), 7.27 (d, J=8.0 Hz, 2H), 6.98 (s, 1H), 2.66 (t, J=7.6 Hz, 2H), 2.43 (s, 3H), 1.73-1.64 (m, 2H), 0.96 (t, J=7.6 Hz, 3H); MH+ 323 and 325.

Preparation Example

5-Bromo-3-methyl-2-(4-propylbenzyl)thiophene (46)

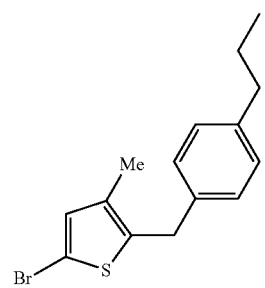 [SMILES: CCCc1ccc(Cc2sc(Br)cc2C)cc1]

To a solution of (5-bromo-3-methylthiophen-2-yl)(4-propylphenyl)methanone (45, 0.95 g, 2.95 mmol) in DCM (9.4 mL) and ACN (9.4 mL) was added triethylsilane (1.42 mL, 8.85 mmol) followed by BF$_3$ etherate (1.11 mL, 8.85 mmol) under nitrogen atmosphere at 0° C. The reaction mixture was allowed warmed to room temperature and stirred for 16 hours. The mixture was poured into a saturated K$_2$CO$_3$ solution (50 mL) and extracted with EtOAc (100 mL). The organic phase was dried over MgSO$_4$ and evaporated under vacuum. The residue was further purified by silica column chromatography (Biotage) to provide 5-bromo-3-methyl-2-(4-propylbenzyl) thiophene (46, 0.86 g, 2.77 mmol, 94%).

$^1$H NMR (400 MHz, CDCl$_3$) δ 7.10 (s, 4H), 6.75 (s, 1H), 3.95 (s, 2H), 2.55 (t, J=7.6 Hz, 2H), 2.12 (s, 3H), 1.67-1.57 (m, 2H), 0.93 (t, J=7.6 Hz, 3H); MH+ 309 and 311.

Preparation Example

5-Iodo-3-methyl-2-(4-propylbenzyl)thiophene (47)

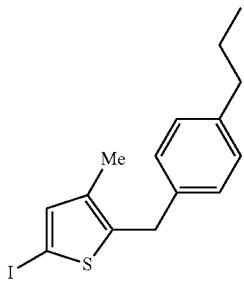 [SMILES: CCCc1ccc(Cc2sc(I)cc2C)cc1]

To a mixture of 5-bromo-3-methyl-2-(4-propylbenzyl) thiophene (46, 0.86 g, 2.77 mmol), sodium iodide (0.83 g, 5.53 mmol) and copper(I) iodide (0.053 g, 0.277 mmol) in dioxane (5.2 mL) was added N,N'-dimethylethylenediamine (0.060 mL, 0.553 mmol). The resulting mixture was heated to 110° C. and stirred for 16 hours. After cooling to room temperature, the reaction mixture was filtered through a plug of Celite® and then washed with EtOAc (50 mL). The filtrate was washed with brine and dried over MgSO$_4$. The organic phase was evaporated under vacuum to provide 5-iodo-3-methyl-2-(4-propylbenzyl)thiophene 47 (0.95 g, 2.66 mmol, 96%) as a yellow oil, which was used without further purification.

M+ 356.

Preparation Example (4-Ethoxyphenyl)(3-methylthiophen-2-yl)methanone Intermediate (44, Via Route b)

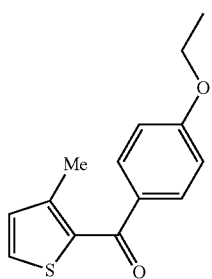 [SMILES: CCOc1ccc(C(=O)c2sccc2C)cc1]

To a solution of 4-bromophenetole (1.86 mL, 13.0 mmol) in anhydrous THF (15 mL) was added dropwise (over a 5-min period) a solution of n-BuLi (6.0 mL, 2.5 M in hexane) under nitrogen atmosphere at −78° C. The resulting mixture was stirred at −78° C. for 1 hour, and then a solution of the Weinreb amide 43 (1.85 g, 10.0 mmol) in anhydrous THF (5.0 mL) was added dropwise (over a 10-min period). The reaction mixture was allowed to warm to room temperature and stirred for 16 hours. The mixture was poured into a 1 M HCl solution (25 mL) and extracted with EtOAc (50 mL). The organic phase was subsequently washed with brine, dried over MgSO$_4$ and evaporated under vacuum. The residue was further purified by silica column chromatography (Biotage) to provide (4-ethoxyphenyl)(3-methylthiophen-2-yl)methanone (44, 1.52 g, 6.16 mmol, 62%).

$^1$H NMR (400 MHz, CDCl$_3$) δ 7.84 (d, J=8.8 Hz, 2H), 7.45 (d, J=5.2 Hz, 1H), 7.98 (d, J=4.8 Hz, 1H), 6.94 (d, J=9.2 Hz, 2H), 4.11 (q, J=6.8 Hz, 2H), 2.40 (s, 3H), 1.45 (t, J=6.8 Hz, 3H); MH+ 247.

Preparation Example (2R,3S,4S,5R,6R)-2-(hydroxymethyl)-6-(4-methyl-5-(4-propylbenzyl)thiophen-2-yl)tetrahydro-2H-pyran-3,4,5-triol (51)

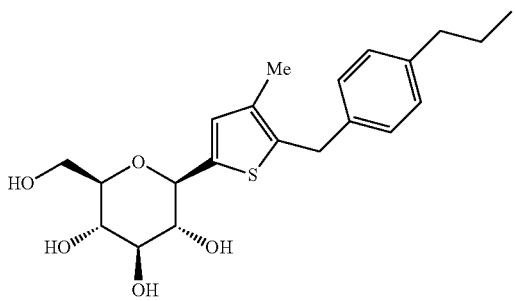

Step 1)

To a solution of 5-iodo-3-methyl-2-(4-propylbenzyl) thiophene (47, 0.95 g, 2.66 mmol) and (3R,4S,5R,6R)-3,4,5-tris(trimethylsilyloxy)-6-((trimethylsilyloxy)methyl)tetrahydro-2H-pyran-2-one (200, 1.37 g, 2.93 mmol) in THF (8.53 mL) was added dropwise (over a 5-min period) a (trimethylsilyl)lithium solution (5.32 mL, 1.0 M in pentane) under nitrogen atmosphere at −50° C. The reaction temperature was maintained −40 to −50° C. for 2 hours. The reaction was quenched with a saturated NaHCO$_3$ solution (20 mL), and then extracted with EtOAc (50 mL). The organic phase was dried over MgSO$_4$ and evaporated under vacuum to provide the crude intermediate 49 ((3R,4S,5R,6R)-2-(4-methyl-5-(4-propylbenzyl)thiophen-2-yl)-3,4,5-tris(trimethylsilyloxy)-6-((trimethylsilyloxy)methyl)tetrahydro-2H-pyran-2-ol).

Step 2)

The crude 49 ((3R,4S,5R,6R)-2-(4-methyl-5-(4-propylbenzyl)thiophen-2-yl)-3,4,5-tris(trimethylsilyloxy)-6-((trimethylsilyloxy)methyl)tetrahydro-2H-pyran-2-ol) was dissolved in anhydrous THF (13.6 mL). To the resulting solution was added dropwise a solution of methanesulfonic acid (0.31 mL in 8 mL MeOH) under nitrogen atmosphere at −78° C. The reaction temperature was maintained −50 to −78° C. for 2 hours. The reaction was quenched with a saturated NaHCO$_3$ solution (20 mL), and then extracted with EtOAc (50 mL). The organic phase was dried over MgSO$_4$ and evaporated under vacuum to provide the crude intermediate 50 ((3R,4S, 5S,6R)-6-(hydroxymethyl)-2-methoxy-2-(4-methyl-5-(4-propylbenzyl)thiophen-2-yl)tetrahydro-2H-pyran-3,4,5-triol), which was used without further purification.

(M-OMe)+ 391.

Step 3)

To a solution of crude (3R,4S,5S,6R)-6-(hydroxymethyl)-2-methoxy-2-(4-methyl-5-(4-propylbenzyl)thiophen-2-yl)tetrahydro-2H-pyran-3,4,5-triol (50) in DCM (11.8 mL) and ACN (11.8 mL) was added triethylsilane (0.786 mL, 4.90 mmol) followed by BF$_3$ etherate (0.611 mL, 4.90 mmol) under nitrogen atmosphere at −60° C. The reaction temperature was maintained −60 to −30° C. for 2 hours. The reaction was quenched with a saturated NaHCO$_3$ solution (20 mL), and then extracted with EtOAc (50 mL). The organic phase was dried over MgSO$_4$ and evaporated under vacuum. The residue was further purified by prep HPLC (C18) to provide the title compound 51 (391 mg, 0.996 mmol, 37%).

$^1$H NMR (400 MHz, CD$_3$OD) δ 6.97 (s, 4H), 6.73 (s, 1H), 4.19 (d, J=9.6 Hz, 1H), 3.89 (s, 2H), 3.75 (d, J=10.0 Hz, 1H), 3.57-3.51 (m, 1H), 3.33-3.24 (m, 4H), 2.44 (t, J=7.6 Hz, 2H), 2.03 (s, 3H), 1.54-1.46 (m, 2H), 0.82 (t, J=7.2 Hz, 3H); [M-OH]+ 375.

Preparation Example (2R,3R,4S,5R,6R)-2-(acetoxymethyl)-6-(3-bromo-5-(4-ethylbenzyl)-4-methylthiophen-2-yl)-tetrahydro-2H-pyran-3,4,5-triyl triacetate (56)

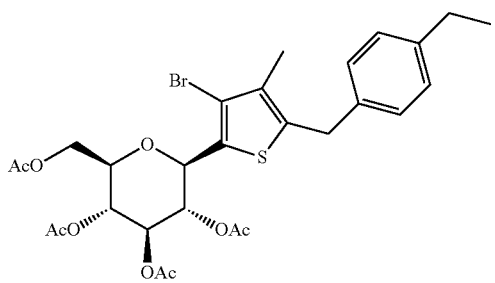 [SMILES: CCc1ccc(Cc2sc([C@@H]3O[C@H](COC(C)=O)[C@@H](OC(C)=O)[C@H](OC(C)=O)[C@H]3OC(C)=O)c(Br)c2C)cc1]

Step 1)

To a solution of N-methoxy-N,3-dimethylthiophene-2-carboxamide (52) (*J. Med. Chem.*, 2001, 44, 863) (5.00 g, 27.0 mmole) in THF (30 mL) was added 4-ethylphenylmagnesium bromide (0.5M in THF, 108 mL, 54.0 mmole) at 0° C. The resulting solution was stirred at ambient temperature overnight. The reaction mixture was quenched by adding MeOH (20 mL) and concentrated in vacuo. The crude residue was purified on Biotage® purification apparatus to yield the compound 53 (4-ethylphenyl)(3-methylthiophen-2-yl)methanone (4.42 g, 19.2 mmole, 71%) as brown oil.

$^1$H NMR (400 MHz, CDCl$_3$) δ 7.77 (dd, J=6.4, 2.0 Hz, 2H), 7.47 (d, J=4.8 Hz, 1H), 7.29 (dd, J=8.0, 0.4 Hz, 2H), 7.00 (dd, J=4.8, 0.4 Hz, 1H), 2.73 (q, J=7.6 Hz, 2H), 2.48 (s, 3H), 1.28 (t, J=7.6 Hz, 3H).

Step 2)

To a solution of (4-ethylphenyl)(3-methylthiophen-2-yl)methanone (53) (4.42 g, 19.2 mmole) in AcOH (30 mL) was added bromine (3.9 mL, 76.8 mmole) slowly. The resulting solution was stirred at ambient temperature overnight. The reaction mixture was quenched by adding saturated Na$_2$S$_2$O$_3$ solution (20 mL) and extracted with EtOAc (2×50 mL). The organic layer was washed with brine and dried over MgSO$_4$, filtered, and concentrated in vacuo. The crude residue was purified on Biotage® purification apparatus to yield the compound 54 (4,5-dibromo-3-methylthiophen-2-yl)(4-ethylphenyl)methanone (4.28 g, 10.6 mmole, 55%) as a yellow solid.

$^1$H NMR (400 MHz, CDCl$_3$) δ 7.72 (dd, J=6.4, 2.0 Hz, 2H), 7.31 (dd, J=6.4, 2.0 Hz, 2H), 2.74 (q, J=7.6 Hz, 2H), 2.45 (s, 3H), 1.28 (t, J=7.6 Hz, 3H); [M+H]+ 387.

Step 3)

To a solution of (4,5-dibromo-3-methylthiophen-2-yl)(4-ethylphenyl)methanone (54) (4.28 g, 10.6 mmole) in DCM/CH$_3$CN (30 mL/30 mL) were added triethylsilane (5.1 mL, 31.9 mmole) and borontrifluoride diethyletherate (3.1 mL, 25.4 mmole) at 0° C. The resulting solution was stirred at ambient temperature overnight. The reaction mixture was quenched by adding MeOH (10 mL) and concentrated in vacuo. The crude residue was purified on Biotage® purification apparatus to yield the compound 55 2,3-dibromo-5-(4-ethylbenzyl)-4-methylthiophene (3.65 g, 9.76 mmole, 92%) as yellow oil.

$^1$H NMR (400 MHz, CDCl$_3$) δ 7.12 (ABq, Δν$_{AB}$=18.2 Hz, J$_{AB}$=8.4 Hz, 4H), 4.00 (s, 2H), 2.63 (q, J=7.6 Hz, 2H), 2.19 (s, 3H), 1.22 (t, J=7.6 Hz, 3H).

Step 4)

To a solution of 2,3-dibromo-5-(4-ethylbenzyl)-4-methylthiophene (55) (3.65 g, 9.76 mmole) and (3R,4S,5R,6R)-3,4,5-tris(trimethylsilyloxy)-6-((trimethylsilyloxy)methyl)-tetrahydropyran-2-one (5.01 g, 10.7 mmole) in THF (50 mL) was added (trimethylsilyl)methyllithium (1M solution in pentane, 20 mL, 19.5 mmole) at −50° C. The resulting solution was stirred at −50~−40° C. for 2 hr. After addition of saturated NaHCO$_3$ solution (20 mL), the mixture was extracted with EtOAc (3×30 mL). The organic layer was washed with brine, dried over MgSO$_4$, filtered, and concentrated in vacuo. The crude residue was dissolved in THF (30 mL) and cooled to −78° C. To this solution was added a solution of methanesulfonic acid (1.5 mL, 23.4 mmole) in MeOH at −78° C. The resulting mixture was warmed to −50° C. over a period of 2 hrs and then saturated NaHCO$_3$ solution (30 mL) was added to the solution. After extraction of the reaction mixture with EtOAc (50 mL×3), the organic layer was washed with brine, dried over MgSO$_4$, filtered, and concentrated in vacuo. The crude residue was dissolved in DCM/CH$_3$CN (20 mL/20 mL) and cooled to −60° C. To this solution were added triethylsilane (3.5 mL, 22.2 mmole) and borontrifluoride diethyletherate (2.2 mL, 17.7 mmole). The resulting mixture was warmed to −30° C. over a period of 2 hrs and then saturated NaHCO$_3$ solution (20 mL) was added to the solution. After extraction of the reaction mixture with EtOAc (50 mL×3), the organic layer was washed with brine, dried over MgSO$_4$, filtered, and concentrated in vacuo. The crude residue was dissolved in DCM (20 mL). To this solution were added dimethylaminopyridine (106 mg, 0.870 mmole), pyridine (4.2 mL, 52.2 mmole), and acetic anhydride (4.1 mL, 43.5 mmole). The resulting mixture was stirred at ambient temperature overnight and then water (30 mL) was added to the solution. After extraction of the reaction mixture with EtOAc (50 mL×2), the organic layer was washed with brine, dried over MgSO$_4$, filtered, and concentrated in vacuo. The crude residue was purified on Biotage® purification apparatus to yield the compound 56 (2R,3R,4S,5R,6R)-2-(acetoxymethyl)-6-(3-bromo-5-(4-ethylbenzyl)-4-methylthiophen-2-yl)-tetrahydro-2H-pyran-3,4,5-triyl triacetate (1.22 g, 1.95 mmole, 20%) as a yellow solid.

$^1$H NMR (400 MHz, CDCl$_3$) δ 7.10 (ABq, Δν$_{AB}$=20.8 Hz, J$_{AB}$=8.4 Hz, 4H), 5.33 (t, J=7.2 Hz, 1H), 5.20-5.13 (m, 2H), 4.88 (d, J=10.0 Hz, 1H), 4.23-4.13 (m, 2H), 4.02 (d, J=3.2 Hz,

2H), 3.86-3.81 (m, 1H), 2.62 (q, J=7.6 Hz, 2H), 2.11 (s, 3H), 2.07 (s, 3H), 2.04 (s, 3H), 2.00 (s, 3H), 1.90 (s, 3H), 1.22 (t, J=7.6 Hz, 3H); [M+Na]+ 647.

Preparation Example (2R,3R,4S,5R,6R)-2-(acetoxymethyl)-6-(5-(4-ethylbenzyl)-3,4-dimethylthiophen-2-yl)tetrahydro-2H-pyran-3,4,5-triyl triacetate (57)

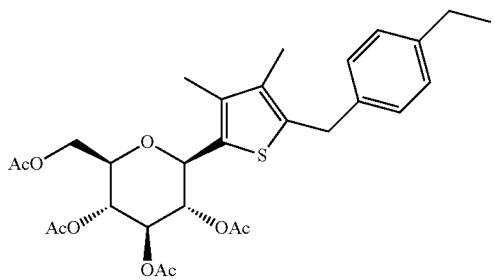 [SMILES: CCc1ccc(Cc2sc([C@@H]3O[C@H](COC(C)=O)[C@@H](OC(C)=O)[C@H](OC(C)=O)[C@H]3OC(C)=O)c(C)c2C)cc1]

To a solution of (2R,3R,4S,5R,6R)-2-(acetoxymethyl)-6-(3-bromo-5-(4-ethylbenzyl)-4-methylthiophen-2-yl)-tetrahydro-2H-pyran-3,4,5-triyl triacetate (56) (200 mg, 0.320 mmole) in toluene/water (4 mL/2 mL) were added trimethylboroxine (134 μL, 0.960 mmole), Pd(OAc)$_2$ (7.2 mg, 0.0320 mmole), tricylcohexylphosphine tetrafluoroborate (23.6 mg, 0.0640 mmole), and K$_3$PO$_4$ (272 mg, 1.28 mmole). The mixture was stirred at 100° C. overnight. The reaction mixture was filtered through celite bed and concentrated in vacuo. The crude residue was purified on Biotage® purification apparatus to yield the title compound 57 (125 mg, 0.223 mmole, 70%) as a yellow solid. [M+Na]+ 583.

Preparation Example (2R,3R,4S,5S,6R)-2-(3-bromo-5-(4-ethylbenzyl)-4-methylthiophen-2-yl)-6-(hydroxymethyl)tetrahydro-2H-pyran-3,4,5-triol (58)

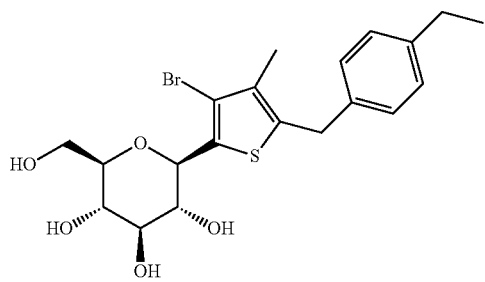 [SMILES: CCc1ccc(Cc2sc([C@@H]3O[C@H](CO)[C@@H](O)[C@H](O)[C@H]3O)c(Br)c2C)cc1]

To a suspension of acetate (56) (200 mg, 0.320 mmol) in MeOH (5 mL) was added NaOMe (25 wt % in MeOH, 0.1 mL) at room temperature. The mixture was stirred at room temperature for 1 hr. Glacial AcOH was added to the mixture to acidify the mixture. The mixture was concentrated under reduced pressure. The residue was purified by prep HPLC (C$_{18}$) to provide the title compound 58 (80 mg, 55%).

$^1$H NMR (400 MHz, CD$_3$OD$_3$) δ 7.10 (s, 4H), 4.60 (d, J=9.2 Hz, 1H), 4.04 (d, J=3.2 Hz, 2H), 3.86-3.80 (m, 1H), 3.63-3.58 (m, 1H), 3.44-3.40 (m, 2H), 3.39-3.32 (m, 2H), 2.58 (q, J=7.6 Hz, 2H), 2.14 (s, 3H), 1.18 (t, J=7.6 Hz, 3H); [M-OH]+ 441.

Preparation Example (2R,3R,4S,5S,6R)-2-(5-(4-ethylbenzyl)-3-methoxy-4-methylthiophen-2-yl)-6-(hydroxymethyl)tetrahydro-2H-pyran-3,4,5-triol (59)

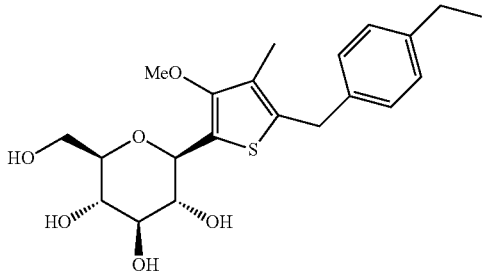 [SMILES: CCc1ccc(Cc2sc([C@@H]3O[C@H](CO)[C@@H](O)[C@H](O)[C@H]3O)c(OC)c2C)cc1]

To a solution of (2R,3R,4S,5R,6R)-2-(acetoxymethyl)-6-(3-bromo-5-(4-ethylbenzyl)-4-methylthiophen-2-yl)-tetrahydro-2H-pyran-3,4,5-triyl triacetate (56) (200 mg, 0.320 mmole) in NaOMe (25 wt % in MeOH, 10 mL, 43.2 mmole) were added cupric oxide (25.5 mg, 0.320 mmole) and KI (53.1 mg, 0.320 mmole). The resulting solution was stirred at 120° C. overnight. The reaction mixture was filtered through Celite® bed and concentrated in vacuo. The crude residue was purified on reverse phase preparative HPLC to yield the title compound 59 (24.3 mg, 0.0595 mmole, 19%) as a yellow solid.

$^1$H NMR (400 MHz, MeOD) δ 7.11-7.09 (m, 4H), 4.52 (dd, J=6.4, 2.4 Hz, 1H), 3.96 (ABq, Δv$_{AB}$=14.0 Hz, J$_{AB}$=16.0 Hz, 2H), 3.84 (dd, J=12.0, 2.0 Hz, 1H), 3.79 (s, 3H), 3.60 (dd, J=12.0, 6.0 Hz, 1H), 3.43 (dd, J=6.4, 2.4 Hz, 2H), 3.39-3.35 (m, 2H), 2.60 (q, J=7.6 Hz, 2H), 2.04 (s, 3H), 1.20 (t, J=7.6 Hz, 3H); [M+Na]+ 431.

Preparation Example (2R,3R,4S,5S,6R)-2-(5-(4-ethylbenzyl)-3,4-dimethylthiophen-2-yl)-6-(hydroxymethyl)tetrahydro-2H-pyran-3,4,5-triol (60)

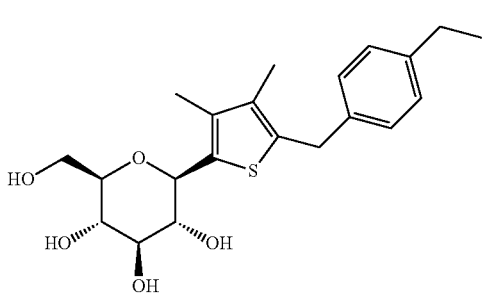 [SMILES: CCc1ccc(Cc2sc([C@@H]3O[C@H](CO)[C@@H](O)[C@H](O)[C@H]3O)c(C)c2C)cc1]

To a solution of (2R,3R,4S,5R,6R)-2-(acetoxymethyl)-6-(5-(4-ethylbenzyl)-3,4-dimethylthiophen-2-yl)tetrahydro-2H-pyran-3,4,5-triyl triacetate (57) (125 mg, 0.223 mmole) in MeOH (5 mL) was added NaOMe (25 wt % in MeOH, 310 μL, 1.34 mmole). The reaction mixture was stirred at ambient temperature for 2 h before AcOH (2 mL) was added. Purification by reverse phase preparative HPLC provided the title compound 60 (24.8 mg, 0.0632 mmole, 28%) as a brown solid.

$^1$H NMR (400 MHz, MeOD) δ 7.08 (s, 4H), 4.50 (d, J=9.2 Hz, 1H), 3.99 (ABq, Δν$_{AB}$=10.4 Hz, J$_{AB}$=16.0 Hz, 2H), 3.84 (dd, J=12.0, 2.0 Hz, 1H), 3.62 (dd, J=12.0, 6.0 Hz, 1H), 3.45-3.35 (m, 4H), 2.59 (q, J=7.6 Hz, 2H), 2.12 (s, 3H), 2.05 (s, 3H), 1.19 (t, J=7.6 Hz, 3H); [M+Na]$^+$ 415.

Example 1

(2R,3R,4S,5S,6R)-2-(5-chloro-4-(4-ethoxybenzyl)thiophen-2-yl)-6-(hydroxymethyl)-tetrahydro-2H-pyran-3,4,5-triol

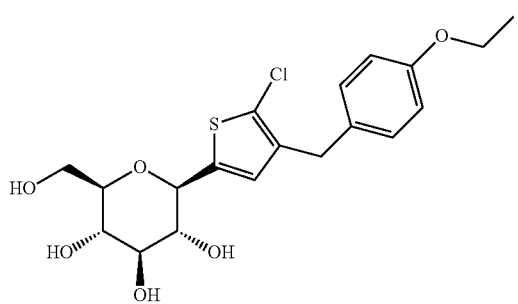

The title compound was obtained in the same manner as in Preparation Example of the compound 20 by using a corresponding starting compound.

$^1$H NMR (400 MHz, DMSO-d$_6$) δ 7.11 (d, J=8.8 Hz, 2H), 6.86-6.81 (m, 3H), 5.18 (d, J=5.6 Hz, 1H), 4.99 (d, J=5.2 Hz, 1H), 4.94 (d, J=5.2 Hz, 1H), 4.46 (t, J=5.6 Hz, 1H), 4.17 (d, J=9.6 Hz, 1H), 3.98 (quartet, J=7.2 Hz, 2H), 3.77 (s, 2H), 3.71-3.63 (m, 1H), 3.40 (quintet, J=6.0 Hz, 1H), 3.26-3.17 (m, 2H), 3.11-3.02 (m, 2H), 1.30 (t, J=7.2 Hz, 3H); M+Na+ 437.

Example 2

(2R,3R,4S,5S,6R)-2-(5-chloro-4-(4-methoxybenzyl)thiophen-2-yl)-6-(hydroxymethyl)-tetrahydro-2H-pyran-3,4,5-triol

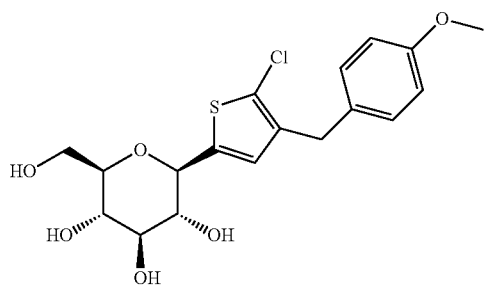 [SMILES: COc1ccc(Cc2cc([C@@H]3O[C@H](CO)[C@@H](O)[C@H](O)[C@H]3O)sc2Cl)cc1]

The title compound was obtained in the same manner as in Preparation Example of the compound 20.

$^1$H NMR (400 MHz, DMSO-d$_6$) δ 7.13 (d, J=8.4 Hz, 2H), 6.86 (d, J=8.4 Hz, 2H), 6.82 (s, 1H), 5.18 (d, J=6.0 Hz, 1H), 4.99 (d, J=5.2 Hz, 1H), 4.94 (d, J=5.6 Hz, 1H), 4.46 (t, J=6.0 Hz, 1H), 4.17 (d, J=9.2 Hz, 1H), 3.77 (s, 2H), 3.73-3.63 (m, 4H), 3.40 (quintet, J=6.0 Hz, 1H), 3.27-3.16 (m, 2H), 3.11-3.01 (m, 2H); M+Na+ 423.

Example 3

(2R,3R,4S,5S,6R)-2-(5-chloro-4-((5-(4-fluorophenyl)thiophen-2-yl)methyl)thiophen-2-yl)-6-(hydroxymethyl)-tetrahydro-2H-pyran-3,4,5-triol

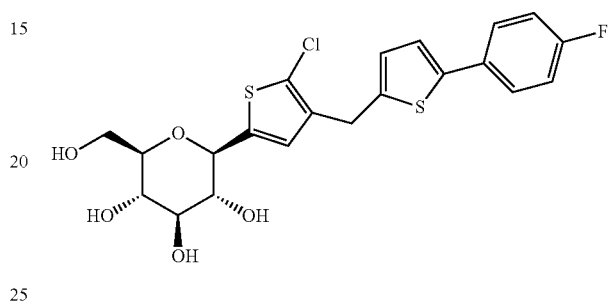

The title compound was obtained in the same manner as in Preparation Example of the compound 20 by using a corresponding starting compound.

$^1$H NMR (400 MHz, DMSO-d$_6$) δ 7.65-7.57 (m, 2H), 7.29 (d, J=3.6 Hz, 1H), 7.25-7.18 (m, 2H), 6.95 (s, 1H), 6.90 (d, J=3.2 Hz, 1H), 5.23 (d, J=5.2 Hz, 1H), 5.01 (d, J=4.8 Hz, 1H), 4.96 (d, J=4.8 Hz, 1H), 4.47 (t, J=6.0 Hz, 1H), 4.21 (d, J=9.2 Hz, 1H), 4.05 (s, 2H), 3.74-3.65 (m, 1H), 3.47-3.35 (m, 1H), 3.28-3.18 (m, 2H), 3.15-3.03 (m, 2H); M+Na+ 493.

Example 4

(2R,3R,4S,5S,6R)-2-(4-(4-(allyloxy)benzyl)-5-chlorothiophen-2-yl)-6-(hydroxymethyl)-tetrahydro-2H-pyran-3,4,5-triol

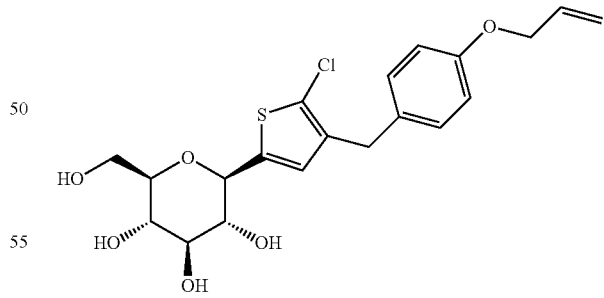

The title compound was obtained in the same manner as in Preparation Example of the compound 30 by using a corresponding starting compound.

$^1$H NMR (400 MHz, DMSO-d$_6$) δ 7.12 (d, J=8.4 Hz, 2H), 6.88 (d, J=8.4 Hz, 2H), 6.83 (s, 1H), 6.08-5.96 (m, 1H), 5.37 (doublet and quartet, J=17.2, 1.6 Hz, 1H), 5.27-5.17 (m, 2H), 5.01 (d, J=4.8 Hz, 1H), 4.96 (d, J=5.2 Hz, 1H), 4.56-4.51 (m, 2H), 4.47 (t, J=5.6 Hz, 1H), 4.17 (d, J=9.6 Hz, 1H), 3.77 (s, 2H), 3.71-3.63 (m, 1H), 3.40 (quintet, J=6.0 Hz, 1H), 3.26-3.16 (m, 2H), 3.11-3.02 (m, 2H); M+Na+ 449.

Example 5

(2R,3R,4S,5S,6R)-2-(5-chloro-4-(4-propoxybenzyl)thiophen-2-yl)-6-(hydroxymethyl)-tetrahydro-2H-pyran-3,4,5-triol

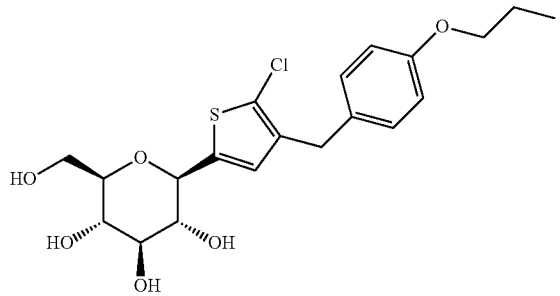 [SMILES: CCCOc1ccc(Cc2cc([C@@H]3O[C@H](CO)[C@@H](O)[C@H](O)[C@H]3O)sc2Cl)cc1]

The title compound was obtained in the same manner as in Preparation Example of the compound 30 by using a corresponding starting compound.

$^1$H NMR (400 MHz, DMSO-d$_6$) δ 7.11 (d, J=8.4 Hz, 2H), 6.88-6.81 (m, 3H), 5.21 (d, J=6.0 Hz, 1H), 5.03 (d, J=4.0 Hz, 1H), 4.97 (d, J=5.2 Hz, 1H), 4.47 (t, J=6.0 Hz, 1H), 4.17 (d, J=9.2 Hz, 1H), 3.87 (t, J=7.6 Hz, 2H), 3.77 (s, 2H), 3.69-3.62 (m, 1H), 3.41 (quintet, J=6.0 Hz, 1H), 3.24-3.17 (m, 2H), 3.13-3.02 (m, 2H), 1.70 (sextet, J=7.2 Hz, 2H), 0.96 (t, J=7.2 Hz, 3H); M+Na+ 451.

Example 6

(2R,3R,4S,5S,6R)-2-(5-chloro-4-(4-hydroxybenzyl)thiophen-2-yl)-6-(hydroxymethyl)-tetrahydro-2H-pyran-3,4,5-triol

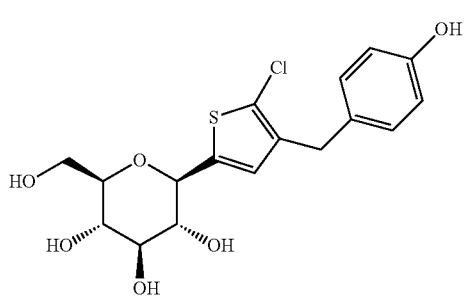 [SMILES: OC[C@H]1O[C@@H](c2cc(Cc3ccc(O)cc3)c(Cl)s2)[C@H](O)[C@@H](O)[C@@H]1O]

The title compound was obtained in the same manner as in Preparation Example of the compound 29.

$^1$H NMR (400 MHz, DMSO-d$_6$) δ 7.00 (d, J=8.4 Hz, 2H), 6.81 (s, 1H), 6.67 (d, J=8.0 Hz, 2H), 5.19 (br s, 1H), 4.98 (br s, 2H), 4.47 (br s, 1H), 4.17 (d, J=9.2 Hz, 1H), 3.73-3.62 (m, 3H), 3.43-3.37 (m, 1H), 3.24-3.14 (m, 3H), 3.12-3.02 (m, 2H); M+Na+ 409.

Example 7

(2R,3R,4S,5S,6R)-2-(5-chloro-4-(4-(ethylthio)benzyl)thiophen-2-yl)-6-(hydroxymethyl)-tetrahydro-2H-pyran-3,4,5-triol

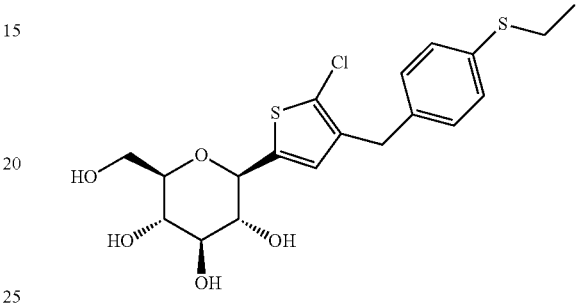

The title compound was obtained in the same manner as in Preparation Example of the compound 20 by using a corresponding starting compound.

$^1$H NMR (400 MHz, DMSO-d$_6$) δ 7.25 (d, J=8.0 Hz, 2H), 7.16 (d, J=8.0 Hz, 2H), 6.85 (s, 1H), 5.20 (d, J=6.0 Hz, 1H), 5.06-4.91 (m, 2H), 4.46 (t, J=5.6 Hz, 1H), 4.18 (d, J=9.6 Hz, 1H), 3.81 (s, 2H), 3.71-3.63 (m, 1H), 3.40 (quintet, J=6.0 Hz, 1H), 3.26-3.17 (m, 2H), 3.12-3.02 (m, 2H), 2.93 (quartet, J=7.2 Hz, 2H), 2.93 (t, J=7.2 Hz, 3H); M+Na+ 453.

Example 8

(2R,3R,4S,5S,6R)-2-(5-chloro-4-(4-(prop-2-ynyloxy)benzyl)thiophen-2-yl)-6-(hydroxymethyl)-tetrahydro-2H-pyran-3,4,5-triol

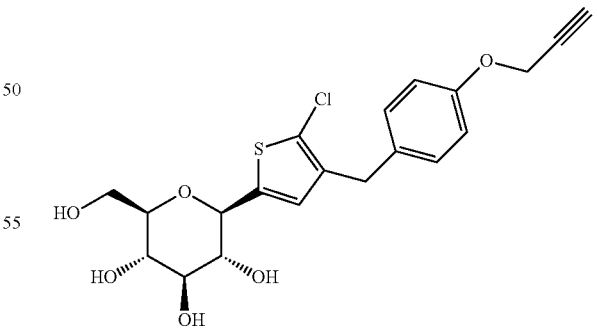

The title compound was obtained in the same manner as in Preparation Example of the compound 30.

$^1$H NMR (400 MHz, DMSO-d$_6$) δ 7.14 (d, J=8.8 Hz, 2H), 6.92 (d, J=8.8 Hz, 2H), 6.84 (s, 1H), 5.20 (d, J=5.6 Hz, 1H), 5.02 (d, J=4.8 Hz, 1H), 4.97 (d, J=5.2 Hz, 1H), 4.74 (d, J=2.4 Hz, 2H), 4.46 (d, J=5.6 Hz, 1H), 4.17 (d, J=9.2 Hz, 1H), 3.78

(s, 2H), 3.71-3.64 (m, 1H), 3.56-3.51 (m, 1H), 3.40 (quintet, J=6.0 Hz, 1H), 3.25-3.16 (m, 2H), 3.13-3.02 (m, 2H); M+Na+ 447.

Example 9

(2R,3R,4S,5S,6R)-2-(5-chloro-4-(4-isopropoxybenzyl)thiophen-2-yl)-6-(hydroxymethyl)-tetrahydro-2H-pyran-3,4,5-triol

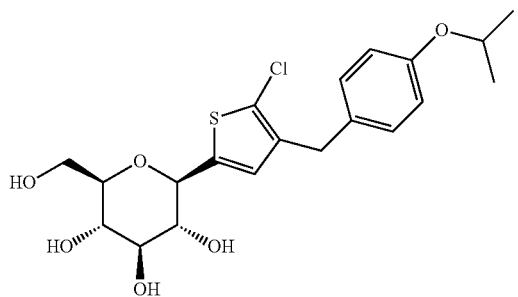 [SMILES: CC(C)Oc1ccc(Cc2cc([C@@H]3O[C@H](CO)[C@@H](O)[C@H](O)[C@H]3O)sc2Cl)cc1]

The title compound was obtained in the same manner as in Preparation Example of the compound 20 by using a corresponding starting compound.

$^1$H NMR (400 MHz, DMSO-$d_6$) δ 7.10 (d, J=8.4 Hz, 2H), 6.86-6.79 (m, 3H), 5.18 (d, J=6.0 Hz, 1H), 4.99 (d, J=6.0 Hz, 1H), 4.94 (d, J=5.6 Hz, 1H), 4.54 (septet, J=6.0 Hz, 1H), 4.46 (t, J=6.0 Hz, 1H), 4.17 (d, J=9.2 Hz, 1H), 3.76 (s, 2H), 3.71-3.63 (m, 1H), 3.40 (quintet, J=6.0 Hz, 1H), 3.26-3.17 (m, 2H), 3.13-3.03 (m, 2H), 1.23 (d, J=6.0 Hz, 6H); M+Na+ 451.

Example 10

(2R,3R,4S,5S,6R)-2-(5-chloro-4-(4-(2-methoxyethoxy)benzyl)thiophen-2-yl)-6-(hydroxymethyl)-tetrahydro-2H-pyran-3,4,5-triol

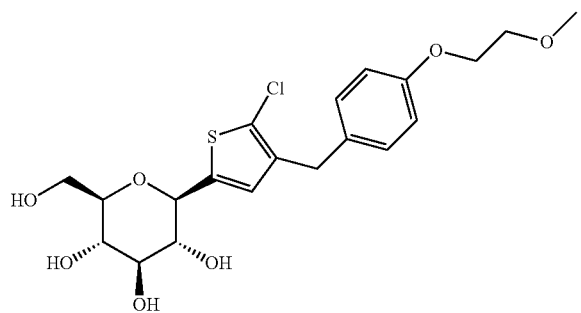 [SMILES: COCCOc1ccc(Cc2cc([C@@H]3O[C@H](CO)[C@@H](O)[C@H](O)[C@H]3O)sc2Cl)cc1]

The title compound was obtained in the same manner as in Preparation Example of the compound 30 by using a corresponding starting compound.

$^1$H NMR (400 MHz, DMSO-$d_6$) δ 7.10 (d, J=8.4 Hz, 2H), 6.86 (d, J=8.8 Hz, 2H), 6.83 (s, 1H), 5.18 (d, J=6.0 Hz, 1H), 5.00 (d, J=4.8 Hz, 1H), 4.95 (d, J=5.6 Hz, 1H), 4.46 (t, J=6.0 Hz, 1H), 4.17 (d, J=9.2 Hz, 1H), 4.07-4.02 (m, 2H), 3.77 (s, 2H), 3.71-3.49 (m, 3H), 3.39 (quintet, J=6.0 Hz, 1H), 3.29 (s, 3H), 3.25-3.17 (m, 2H), 3.12-3.02 (m, 2H); M+Na+ 467.

Example 11

(2R,3R,4S,5S,6R)-2-(5-chloro-4-(4-(cyclopentyloxy)benzyl)thiophen-2-yl)-6-(hydroxymethyl)-tetrahydro-2H-pyran-3,4,5-triol

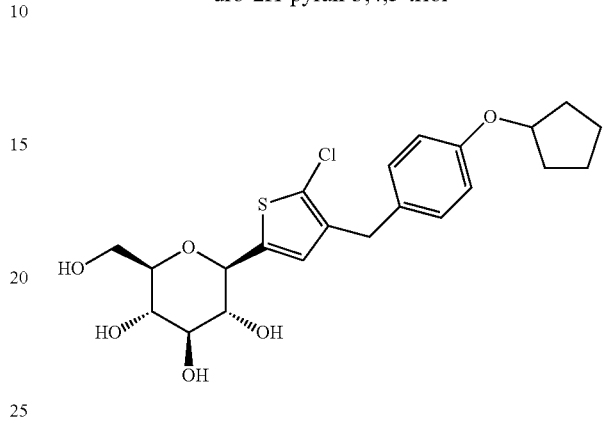

The title compound was obtained in the same manner as in Preparation Example of the compound 20 by using a corresponding starting compound.

$^1$H NMR (400 MHz, DMSO-$d_6$) δ 7.10 (d, J=8.8 Hz, 2H), 6.82 (d, J=8.8 Hz, 2H), 6.79 (s, 1H), 5.18 (d, J=5.6 Hz, 1H), 4.99 (d, J=4.8 Hz, 1H), 4.94 (d, J=5.2 Hz, 1H), 4.75 (quintet, J=6.0 Hz, 1H), 4.45 (t, J=6.0 Hz, 1H), 4.17 (d, J=9.2 Hz, 1H), 3.76 (s, 2H), 3.70-3.54 (m, 1H), 3.39 (quintet, J=6.0 Hz, 1H), 3.26-3.17 (m, 2H), 3.13-3.03 (m, 2H), 1.94-1.82 (m, 2H), 1.73-1.63 (m, 4H), 1.61-1.52 (m, 2H); M+Na+ 477.

Example 12

(2R,3R,4S,5S,6R)-2-(5-chloro-4-(4-(methylthio)benzyl)thiophen-2-yl)-6-(hydroxymethyl)-tetrahydro-2H-pyran-3,4,5-triol

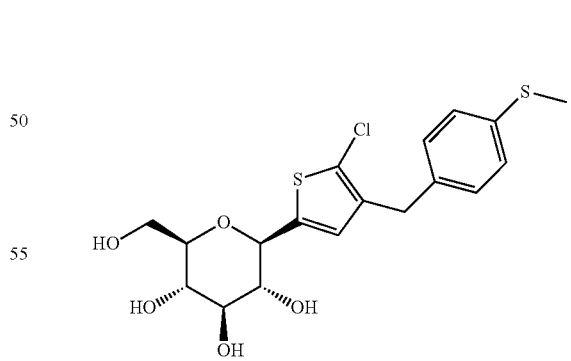

The title compound was obtained in the same manner as in Preparation Example of the compound 20 by using a corresponding starting compound.

$^1$H NMR (400 MHz, DMSO-$d_6$) δ 7.23-7.14 (m, 4H), 6.84 (s, 1H), 5.19 (d, J=5.6 Hz, 1H), 4.99 (d, J=5.2 Hz, 1H), 4.94 (d, J=5.2 Hz, 1H), 4.45 (t, J=6.0 Hz, 1H), 4.17 (d, J=9.2 Hz,

1H), 3.81 (s, 2H), 3.72-3.63 (m, 1H), 3.40 (quintet, J=6.0 Hz, 1H), 3.25-3.16 (m, 2H), 3.11-3.01 (m, 2H), 2.43 (s, 3H); M+Na+ 439.

Example 13

(2R,3R,4S,5S,6R)-2-(5-chloro-4-(4-(2-ethoxyethoxy)benzyl)thiophen-2-yl)-6-(hydroxymethyl)-tetrahydro-2H-pyran-3,4,5-triol

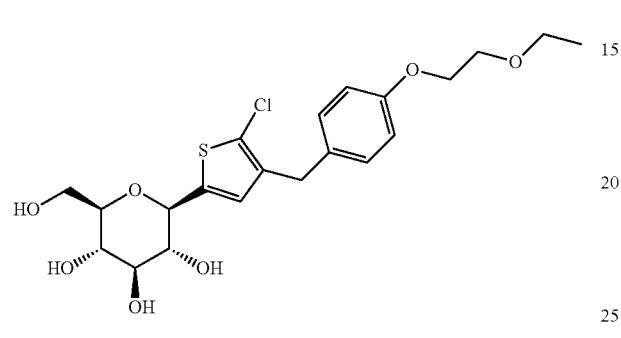

The title compound was obtained in the same manner as in Preparation Example of the compound 30 by using a corresponding starting compound.

¹H NMR (400 MHz, DMSO-d₆) δ 7.12 (d, J=8.4 Hz, 2H), 6.86 (d, J=8.8 Hz, 2H), 6.82 (s, 1H), 5.19 (d, J=5.6 Hz, 1H), 5.00 (d, J=4.4 Hz, 1H), 4.95 (d, J=5.2 Hz, 1H), 4.46 (t, J=5.6 Hz, 1H), 4.17 (d, J=9.2 Hz, 1H), 4.08-4.02 (m, 2H), 3.77 (s, 2H), 3.71-3.62 (m, 3H), 3.48 (quartet, J=7.2 Hz, 2H), 3.39 (quintet, J=6.0 Hz, 1H), 3.27-3.15 (m, 2H), 3.12-3.03 (m, 2H), 1.12 (t, J=7.2 Hz, 3H); M+Na+ 481.

Example 14

(2R,3R,4S,5S,6R)-2-(5-chloro-4-(4-methylbenzyl)thiophen-2-yl)-6-(hydroxymethyl)-tetrahydro-2H-pyran-3,4,5-triol

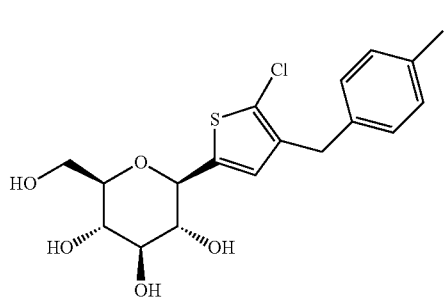 [SMILES: Cc1ccc(Cc2cc([C@@H]3O[C@H](CO)[C@@H](O)[C@H](O)[C@H]3O)sc2Cl)cc1]

The title compound was obtained in the same manner as in Preparation Example of the compound 41.

¹H NMR (400 MHz, DMSO-d₆) δ 7.10 (s, 4H), 6.82 (s, 1H), 5.19 (d, J=5.6 Hz, 1H), 5.00 (d, J=4.8 Hz, 1H), 4.95 (d, J=5.2 Hz, 1H), 4.46 (t, J=5.6 Hz, 1H), 4.17 (d, J=9.2 Hz, 1H), 3.79 (s, 2H), 3.60-3.51 (m, 1H), 3.40 (quintet, J=6.0 Hz, 1H), 3.25-3.16 (m, 2H), 3.11-3.02 (m, 2H), 2.25 (s, 3H); M+Na+ 407.

Example 15

(2R,3R,4S,5S,6R)-2-(4-(4-(but-2-ynyloxy)benzyl)-5-chlorothiophen-2-yl)-6-(hydroxymethyl)-tetrahydro-2H-pyran-3,4,5-triol

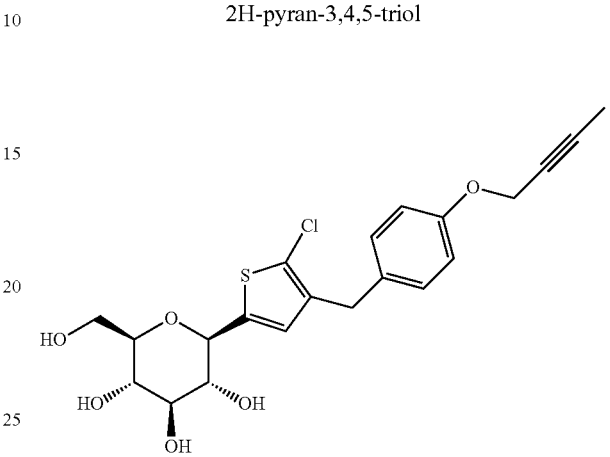

The title compound was obtained in the same manner as in Preparation Example of the compound 30 by using a corresponding starting compound.

¹H NMR (400 MHz, DMSO-d₆) δ 7.13 (d, J=8.4 Hz, 2H), 6.88 (d, J=8.4 Hz, 2H), 6.84 (s, 1H), 5.18 (d, J=4.8 Hz, 1H), 4.98 (d, J=4.8 Hz, 1H), 4.93 (d, J=5.2 Hz, 1H), 4.68 (quartet, J=2.4 Hz, 2H), 4.45 (t, J=5.2 Hz, 1H), 4.17 (t, J=9.2 Hz, 1H), 3.78 (s, 2H), 3.71-3.62 (m, 1H), 3.40 (quintet, J=6.0 Hz, 1H), 3.25-3.17 (m, 2H), 3.13-3.02 (m, 2H), 3.40 (t, J=1.8 Hz, 3H); M+Na+ 461.

Example 16

(2R,3R,4S,5S,6R)-2-(5-chloro-4-(4-(tetrahydrofuran-3-yloxy)benzyl)thiophen-2-yl)-6-(hydroxymethyl)-tetrahydro-2H-pyran-3,4,5-triol

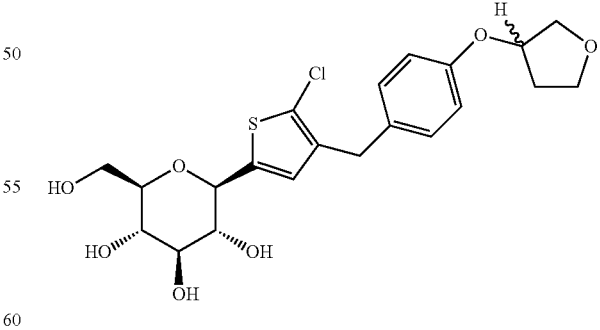

The title compound was obtained in the same manner as in Preparation Example of the compound 20 by using a corresponding starting compound.

¹H NMR (400 MHz, DMSO-d₆) δ 7.12 (d, J=8.4 Hz, 2H), 6.87-6.79 (m, 3H), 5.18 (d, J=5.2 Hz, 1H), 5.02-4.91 (m, 2H), 4.45 (t, J=5.2 Hz, 1H), 4.17 (t, J=9.6 Hz, 1H), 3.88-3.63 (m,

8H), 3.40 (quintet, J=6.0 Hz, 1H), 3.26-3.17 (m, 2H), 3.12-3.01 (m, 2H), 2.23-2.12 (m, 1H), 1.98-1.88 (m, 1H); M+Na+ 479.

Example 17

(2R,3R,4S,5S,6R)-2-(5-chloro-4-(4-ethylbenzyl)thiophen-2-yl)-6-(hydroxymethyl)-tetrahydro-2H-pyran-3,4,5-triol

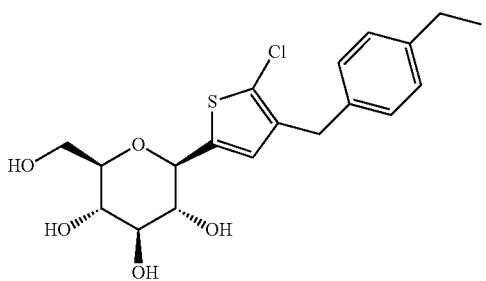 [SMILES: CCc1ccc(Cc2cc([C@@H]3O[C@H](CO)[C@@H](O)[C@H](O)[C@H]3O)sc2Cl)cc1]

The title compound was obtained in the same manner as in Preparation Example of the compound 41 by using a corresponding starting compound.

$^1$H NMR (400 MHz, DMSO-d$_6$) δ 7.13 (s, 4H), 6.84 (s, 1H), 5.17 (d, J=6.0 Hz, 1H), 4.99 (d, J=5.2 Hz, 1H), 4.93 (d, J=5.2 Hz, 1H), 4.45 (t, J=6.0 Hz, 1H), 4.17 (d, J=9.6 Hz, 1H), 3.80 (s, 2H), 3.71-3.63 (m, 1H), 3.41 (quintet, J=6.0 Hz, 1H), 3.26-3.17 (m, 2H), 3.13-3.02 (m, 2H), 2.55 (quartet, J=7.2 Hz, 2H), 1.15 (t, J=7.6 Hz, 3H); M+Na+ 421.

Example 18

(2R,3R,4S,5S,6R)-2-(5-chloro-4-(4-propylbenzyl)thiophen-2-yl)-6-(hydroxymethyl)-tetrahydro-2H-pyran-3,4,5-triol

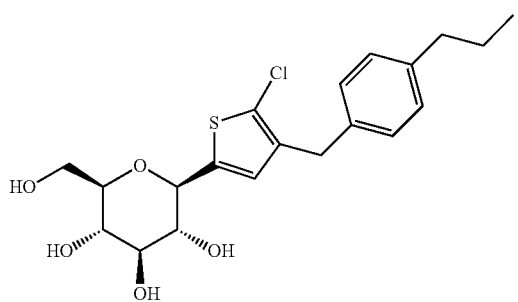

The title compound was obtained in the same manner as in Preparation Example of the compound 41 by using a corresponding starting compound.

$^1$H NMR (400 MHz, DMSO-d$_6$) δ 7.11 (s, 4H), 6.84 (s, 1H), 5.17 (d, J=6.0 Hz, 1H), 4.97 (d, J=5.2 Hz, 1H), 4.93 (d, J=5.2 Hz, 1H), 4.44 (t, J=6.0 Hz, 1H), 4.17 (d, J=9.2 Hz, 1H), 3.80 (s, 2H), 3.66 (quartet and doublet, J=5.6, 1.6 Hz, 1H), 3.41 (quintet, J=6.0 Hz, 1H), 3.24-3.17 (m, 2H), 3.12-3.02 (m, 2H), 2.54-2.45 (m, 2H), 1.55 (sextet, J=7.2 Hz, 2H), 0.88 (t, J=7.2 Hz, 3H); M+Na+ 435.

Example 19

(2R,3R,4S,5S,6R)-2-(4-(4-ethoxybenzyl)-5-methylthiophen-2-yl)-6-(hydroxymethyl)-tetrahydro-2H-pyran-3,4,5-triol

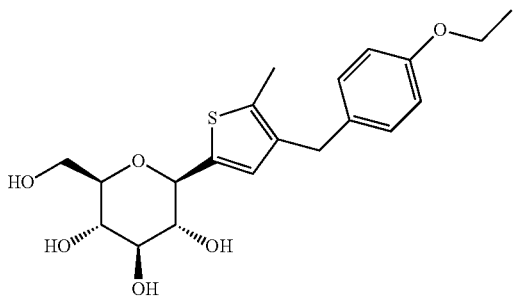 [SMILES: CCOc1ccc(Cc2cc([C@@H]3O[C@H](CO)[C@@H](O)[C@H](O)[C@H]3O)sc2C)cc1]

The title compound was obtained in the same manner as in Preparation Example of the compound 20 by using a corresponding starting compound.

$^1$H NMR (400 MHz, DMSO-d$_6$) δ 7.07 (d, J=8.4 Hz, 2H), 6.83 (d, J=8.4 Hz, 2H), 6.69 (s, 1H), 4.94-4.87 (m, 3H), 4.43 (t, J=6.0 Hz, 1H), 4.12 (d, J=9.2 Hz, 1H), 3.96 (quartet, J=7.2 Hz, 2H), 3.68 (s, 2H), 3.65 (quartet and doublet, J=5.6, 1.6 Hz, 1H), 3.40 (quintet, J=6.0 Hz, 1H), 3.23-3.14 (m, 2H), 3.13-3.05 (m, 2H), 2.32 (s, 3H), 1.29 (t, J=7.2 Hz, 3H); M+Na+ 417.

Example 20

(2R,3S,4S,5R,6R)-2-(hydroxymethyl)-6-(4-(4-methoxybenzyl)-5-methylthiophen-2-yl)-tetrahydro-2H-pyran-3,4,5-triol

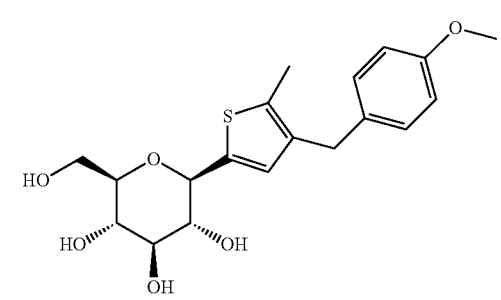 [SMILES: COc1ccc(Cc2cc([C@@H]3O[C@H](CO)[C@@H](O)[C@H](O)[C@H]3O)sc2C)cc1]

The title compound was obtained in the same manner as in Preparation Example of the compound 20 by using a corresponding starting compound.

$^1$H NMR (400 MHz, DMSO-d$_6$) δ 7.09 (d, J=8.4 Hz, 2H), 6.83 (d, J=8.4 Hz, 2H), 6.69 (s, 1H), 4.95-4.87 (m, 3H), 4.42 (t, J=5.6 Hz, 1H), 4.12 (d, J=9.2 Hz, 1H), 3.73-3.62 (m, 6H), 3.39 (quintet, J=6.0 Hz, 1H), 3.23-3.13 (m, 2H), 3.12-3.03 (m, 2H), 2.33 (s, 3H); M+Na+ 403.

Example 21

(2R,3R,4S,5S,6R)-2-(4-((5-(4-fluorophenyl)thiophen-2-yl)methyl)-5-methylthiophen-2-yl)-6-(hydroxymethyl)-tetrahydro-2H-pyran-3,4,5-triol

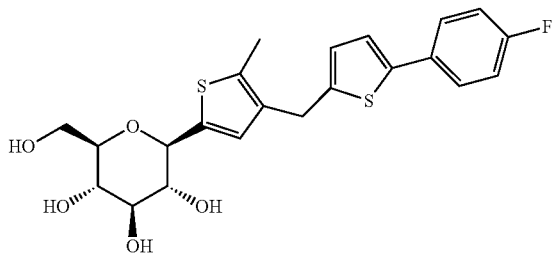 [SMILES: Cc1sc([C@@H]2O[C@H](CO)[C@@H](O)[C@H](O)[C@H]2O)cc1Cc1ccc(-c2ccc(F)cc2)s1]

The title compound was obtained in the same manner as in Preparation Example of the compound 20 by using a corresponding starting compound.

$^1$H NMR (400 MHz, DMSO-$d_6$) δ 7.63-7.56 (m, 2H), 7.27 (d, J=3.2 Hz, 1H), 7.24-7.17 (m, 2H), 6.86 (d, J=3.6 Hz, 1H), 6.82 (s, 1H), 4.96 (d, J=6.0 Hz, 1H), 4.94 (d, J=4.8 Hz, 1H), 4.90 (d, J=5.2 Hz, 1H), 4.43 (t, J=5.6 Hz, 1H), 4.16 (d, J=9.2 Hz, 1H), 4.00 (s, 2H), 3.66 (quartet and doublet, J=5.6, 1.6 Hz, 1H), 3.39 (quintet, J=6.0 Hz, 1H), 3.25-3.17 (m, 2H), 3.15-3.05 (m, 2H), 2.36 (s, 3H); M+Na+ 473.

Example 22

(2R,3R,4S,5S,6R)-2-(4-(4-(allyloxy)benzyl)-5-methylthiophen-2-yl)-6-(hydroxymethyl)-tetrahydro-2H-pyran-3,4,5-triol

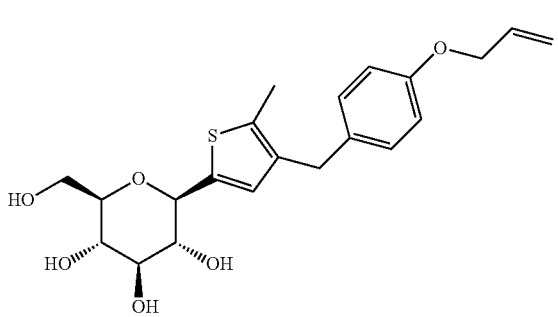 [SMILES: C=CCOc1ccc(Cc2cc([C@@H]3O[C@H](CO)[C@@H](O)[C@H](O)[C@H]3O)sc2C)cc1]

The title compound was obtained in the same manner as in Preparation Example of the compound 30 by using a corresponding starting compound.

$^1$H NMR (400 MHz, DMSO-$d_6$) δ 7.08 (d, J=8.8 Hz, 2H), 6.84 (d, J=8.4 Hz, 2H), 6.70 (s, 1H), 6.09-5.97 (m, 1H), 5.37 (quartet and doublet, J=17.6, 1.6 Hz, 1H), 5.23 (quartet and doublet, J=17.6, 1.6 Hz, 1H), 4.98-4.87 (m, 3H), 4.51 (doublet and triplet, J=5.2, 1.6 Hz, 2H), 4.40 (t, J=5.2 Hz, 1H), 4.12 (d, J=9.2 Hz, 1H), 3.71 (s, 2H), 3.69-3.62 (m, 1H), 3.40 (quintet, J=6.0 Hz, 1H), 3.26-3.15 (m, 2H), 3.14-3.03 (m, 2H), 2.31 (s, 3H); M+Na+ 429.

Example 23

(2R,3R,4S,5S,6R)-2-(4-(4-hydroxybenzyl)-5-methylthiophen-2-yl)-6-(hydroxymethyl)-tetrahydro-2H-pyran-3,4,5-triol

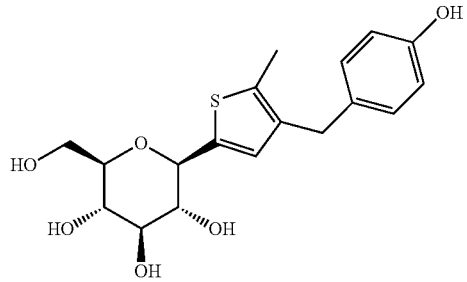 [SMILES: Cc1sc([C@@H]2O[C@H](CO)[C@@H](O)[C@H](O)[C@H]2O)cc1Cc1ccc(O)cc1]

The title compound was obtained in the same manner as in Preparation Example of the compound 29 by using a corresponding starting compound.

$^1$H NMR (400 MHz, DMSO-$d_6$) δ 9.15 (s, 1H), 6.96 (d, J=8.4 Hz, 2H), 6.66 (d, J=8.4 Hz, 2H), 6.64 (s, 1H), 4.97-4.88 (m, 3H), 4.41 (t, J=6.0 Hz, 1H), 4.12 (d, J=9.2 Hz, 1H), 3.71-3.61 (m, 3H), 3.41 (quintet, J=6.0 Hz, 1H), 3.24-3.14 (m, 2H), 3.13-3.03 (m, 2H), 2.31 (s, 3H); M+Na+ 389.

Example 24

(2R,3S,4S,5R,6R)-2-(hydroxymethyl)-6-(4-methyl-5-(4-propylbenzyl)thiophen-2-yl)tetrahydro-2H-pyran-3,4,5-triol

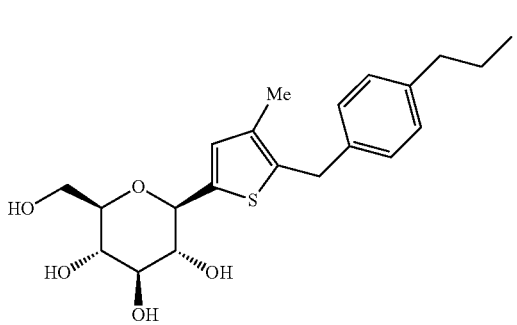 [SMILES: CCCc1ccc(Cc2sc([C@@H]3O[C@H](CO)[C@@H](O)[C@H](O)[C@H]3O)cc2C)cc1]

The title compound was obtained in the same manner as in Preparation Example of the compound 51.

$^1$H NMR (400 MHz, CD$_3$OD) δ 6.97 (s, 4H), 6.73 (s, 1H), 4.19 (d, J=9.6 Hz, 1H), 3.89 (s, 2H), 3.75 (d, J=10.0 Hz, 1H), 3.57-3.51 (m, 1H), 3.33-3.24 (m, 4H), 2.44 (t, J=7.6 Hz, 2H), 2.03 (s, 3H), 1.54-1.46 (m, 2H), 0.82 (t, J=7.2 Hz, 3H); [M-OH]+375.

Example 25

(2R,3R,4S,5S,6R)-2-(5-(4-ethylbenzyl)-4-methylthiophen-2-yl)-6-(hydroxymethyl)tetrahydro-2H-pyran-3,4,5-triol

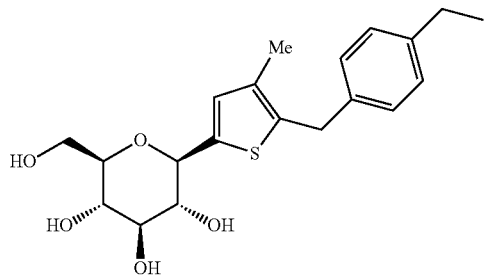 [SMILES: CCc1ccc(Cc2sc([C@@H]3O[C@H](CO)[C@@H](O)[C@H](O)[C@H]3O)cc2C)cc1]

The title compound was obtained in the same manner as in Preparation Example of the compound 51 by using a corresponding starting compound.

$^1$H NMR (400 MHz, CD$_3$OD) δ 7.07 (s, 4H), 6.80 (s, 1H), 4.26 (d, J=9.2 Hz, 1H), 3.96 (s, 2H), 3.83 (d, J=12.0 Hz, 1H), 3.63-3.59 (m, 1H), 3.41-3.32 (m, 4H), 2.57 (q, J=7.6 Hz, 2H), 2.11 (s, 3H), 1.18 (t, J=7.6 Hz, 3H); [M-OH]+361.

Example 26

(2R,3S,4S,5R,6R)-2-(hydroxymethyl)-6-(4-methyl-5-(4-methylbenzyl)thiophen-2-yl)tetrahydro-2H-pyran-3,4,5-triol

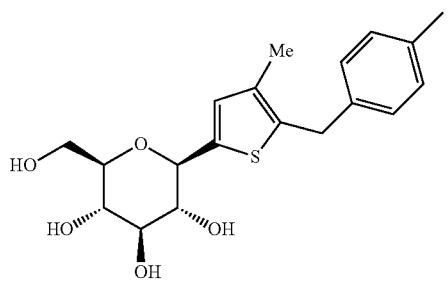 [SMILES: Cc1ccc(Cc2sc([C@@H]3O[C@H](CO)[C@@H](O)[C@H](O)[C@H]3O)cc2C)cc1]

The title compound was obtained in the same manner as in Preparation Example of the compound 51 by using a corresponding starting compound.

6 Hz, 1H), 3.95 (s, 2H), 3.83 (d, J=11.6 Hz, 1H), 3.63-3.59 (m, 1H), 3.41-3.30 (m, 4H), 2.26 (s, 3H), 2.10 (s, 3H); [M—OH]-347.

Example 27

(2R,3R,4S,5S,6R)-2-(5-(4-tert-butylbenzyl)-4-methylthiophen-2-yl)-6-(hydroxymethyl)tetrahydro-2H-pyran-3,4,5-triol

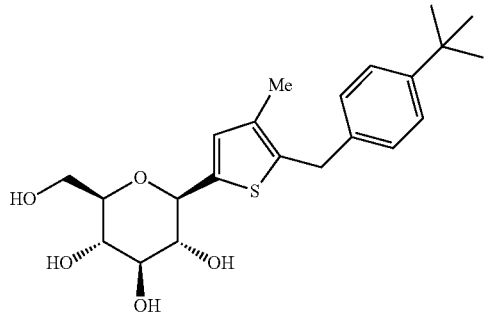 [SMILES: Cc1cc([C@@H]2O[C@H](CO)[C@@H](O)[C@H](O)[C@H]2O)sc1Cc1ccc(C(C)(C)C)cc1]

The title compound was obtained in the same manner as in Preparation Example of the compound 51 by using a corresponding starting compound.

$^1$H NMR (400 MHz, CD$_3$OD) δ 7.27 (d, J=8.4 Hz, 2H), 7.09 (d, J=8.4 Hz, 2H), 6.80 (s, 1H), 4.26 (d, J=9.2 Hz, 1H), 3.96 (s, 2H), 3.83 (d, J=12.0 Hz, 1H), 3.63-3.59 (m, 1H), 3.39-3.32 (m, 4H), 2.12 (s, 3H), 1.27 (s, 9H); [M-OH]+389.

Example 28

(2R,3R,4S,5S,6R)-2-(5-(4-chlorobenzyl)-4-methylthiophen-2-yl)-6-(hydroxymethyl)tetrahydro-2H-pyran-3,4,5-triol

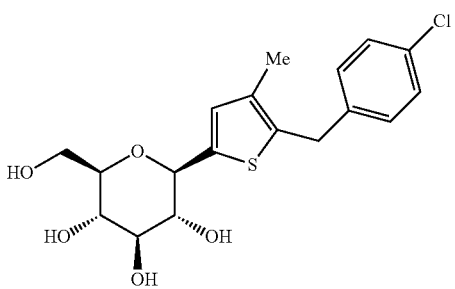 [SMILES: Cc1cc([C@@H]2O[C@H](CO)[C@@H](O)[C@H](O)[C@H]2O)sc1Cc1ccc(Cl)cc1]

The title compound was obtained in the same manner as in Preparation Example of the compound 51 by using a corresponding starting compound.

$^1$H NMR (400 MHz, CD$_3$OD) δ 7.23 (d, J=8.8 Hz, 2H), 7.15 (d, J=8.8 Hz, 2H), 6.82 (s, 1H), 4.27 (d, J=9.6 Hz, 1H), 4.00 (s, 2H), 3.83 (d, J=12.0 Hz, 1H), 3.62-3.59 (m, 1H), 3.39-3.30 (m, 4H), 2.10 (s, 3H); [M-OH]+367.

Example 29

(2R,3R,4S,5S,6R)-2-(5-(4-fluorobenzyl)-4-methylthiophen-2-yl)-6-(hydroxymethyl)tetrahydro-2H-pyran-3,4,5-triol

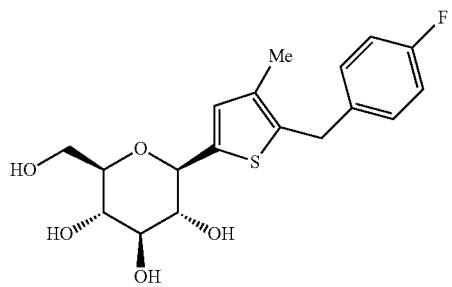 [SMILES: Cc1cc([C@@H]2O[C@H](CO)[C@@H](O)[C@H](O)[C@H]2O)sc1Cc1ccc(F)cc1]

The title compound was obtained in the same manner as in Preparation Example of the compound 51 by using a corresponding starting compound.

$^1$H NMR (400 MHz, CD$_3$OD) δ 7.19-7.16 (m, 2H), 6.98-6.94 (m, 2H), 6.82 (s, 1H), 4.27 (d, J=9.6 Hz, 1H), 4.00 (s, 2H), 3.83 (d, J=12.0 Hz, 1H), 3.64-3.59 (m, 1H), 3.41-3.32 (m, 4H), 2.10 (s, 3H); [M-OH]+351.

Example 30

(2R,3S,4S,5R,6R)-2-(hydroxymethyl)-6-(5-(4-methoxybenzyl)-4-methylthiophen-2-yl)tetrahydro-2H-pyran-3,4,5-triol

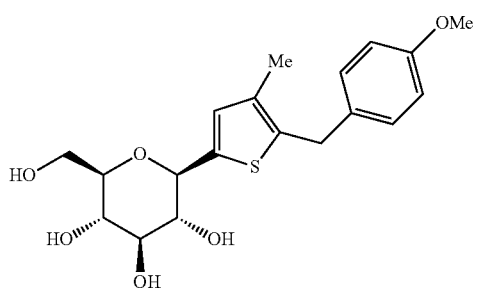 [SMILES: COc1ccc(Cc2sc([C@@H]3O[C@H](CO)[C@@H](O)[C@H](O)[C@H]3O)cc2C)cc1]

The title compound was obtained in the same manner as in Preparation Example of the compound 51 by using a corresponding starting compound.

$^1$H NMR (400 MHz, CD$_3$OD) δ 7.08 (d, J=8.8 Hz, 2H), 6.81 (s, 1H), 6.79 (d, J=8.8 Hz, 2H), 4.26 (d, J=9.6 Hz, 1H), 3.93 (s, 2H), 3.83 (d, J=11.6 Hz, 1H), 3.73 (s, 3H), 3.63-3.59 (m, 1H), 3.41-3.30 (m, 4H), 2.10 (s, 3H); [M-OH]+363.

Example 31

(2R,3R,4S,5S,6R)-2-(5-(4-ethoxybenzyl)-4-methylthiophen-2-yl)-6-(hydroxymethyl)tetrahydro-2H-pyran-3,4,5-triol

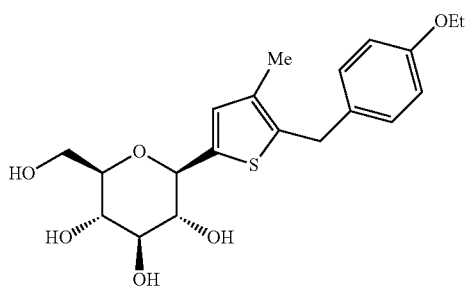 [SMILES: CCOc1ccc(Cc2sc([C@@H]3O[C@H](CO)[C@@H](O)[C@H](O)[C@H]3O)cc2C)cc1]

The title compound was obtained in the same manner as in Preparation Example of the compound 51 by using a corresponding starting compound.

$^1$H NMR (400 MHz, CD$_3$OD) δ 7.18 (d, J=8.8 Hz, 2H), 6.92 (s, 1H), 6.90 (d, J=8.8 Hz, 2H), 4.38 (d, J=9.6 Hz, 1H), 4.09 (q, J=7.2 Hz, 2H), 4.05 (s, 2H), 3.95 (d, J=11.6 Hz, 1H), 3.76-3.71 (m, 1H), 3.53-3.42 (m, 4H), 2.22 (s, 3H), 1.45 (t, J=7.2 Hz, 3H); [M-OH]+377.

Example 32

(2R,3R,4S,5S,6R)-2-(3-bromo-5-(4-ethylbenzyl)-4-methylthiophen-2-yl)-6-(hydroxymethyl)tetrahydro-2H-pyran-3,4,5-triol

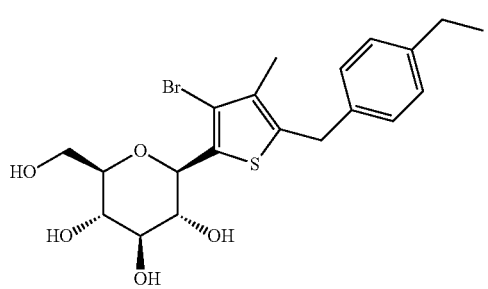 [SMILES: CCc1ccc(Cc2sc([C@@H]3O[C@H](CO)[C@@H](O)[C@H](O)[C@H]3O)c(Br)c2C)cc1]

The title compound was obtained in the same manner as in Preparation Example of the compound 58.

$^1$H NMR (400 MHz, CD$_3$OD) δ 7.18 (d, J=8.8 Hz, 2H), 6.92 (s, 1H), 6.90 (d, J=8.8 Hz, 2H), 4.38 (d, J=9.6 Hz, 1H), 4.09 (q, J=7.2 Hz, 2H), 4.05 (s, 2H), 3.95 (d, J=11.6 Hz, 1H), 3.76-3.71 (m, 1H), 3.53-3.42 (m, 4H), 2.22 (s, 3H), 1.45 (t, J=7.2 Hz, 3H); [M-OH]+377.

Example 33

(2R,3R,4S,5S,6R)-2-(5-(4-ethylbenzyl)-3-methoxy-4-methylthiophen-2-yl)-6-(hydroxymethyl)tetrahydro-2H-pyran-3,4,5-triol

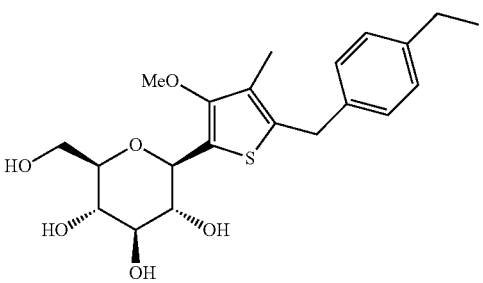

The title compound was obtained in the same manner as in Preparation Example of the compound 59.

$^1$H NMR (400 MHz, CD$_3$OD) δ 7.18 (d, J=8.8 Hz, 2H), 6.92 (s, 1H), 6.90 (d, J=8.8 Hz, 2H), 4.38 (d, J=9.6 Hz, 1H), 4.09 (q, J=7.2 Hz, 2H), 4.05 (s, 2H), 3.95 (d, J=11.6 Hz, 1H), 3.76-3.71 (m, 1H), 3.53-3.42 (m, 4H), 2.22 (s, 3H), 1.45 (t, J=7.2 Hz, 3H); [M-OH]+377.

Example 34

(2R,3R,4S,5S,6R)-2-(5-(4-ethylbenzyl)-3,4-dimethylthiophen-2-yl)-6-(hydroxymethyl)tetrahydro-2H-pyran-3,4,5-triol

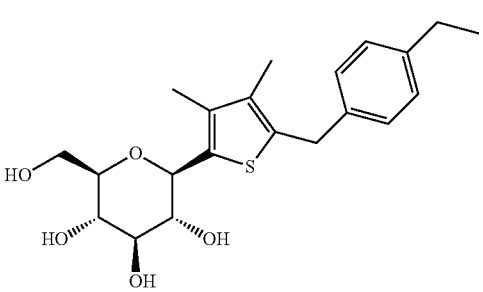 [SMILES: CCc1ccc(Cc2sc([C@@H]3O[C@H](CO)[C@@H](O)[C@H](O)[C@H]3O)c(C)c2C)cc1]

The title compound was obtained in the same manner as in Preparation Example of the compound 60.

$^1$H NMR (400 MHz, CD$_3$OD) δ 7.18 (d, J=8.8 Hz, 2H), 6.92 (s, 1H), 6.90 (d, J=8.8 Hz, 2H), 4.38 (d, J=9.6 Hz, 1H), 4.09 (q, J=7.2 Hz, 2H), 4.05 (s, 2H), 3.95 (d, J=11.6 Hz, 1H), 3.76-3.71 (m, 1H), 3.53-3.42 (m, 4H), 2.22 (s, 3H), 1.45 (t, J=7.2 Hz, 3H); [M-OH]+377.

In Vitro Assay
Test 1: Cloning and Cell Line Construction for Human SGLT2

Human SGLT2 (hSGLT2) gene was amplified by PCR from cDNA-Human Adult Normal Tissue Kidney (Invitrogen). The hSGLT2 sequence was cloned into pcDNA3.1(+) for mammalian expression and were stably transfected into chinese hamster ovary (CHO) cells. SGLT2-expressing clones were selected based on resistance to G418 antibiotic (Geneticin) and activity in the $^{14}$C-α-methyl-D-glucopyranoside ($^{14}$C-AMG) uptake assay.

Test 2: Inhibitory Effects on Human SGLT2 Activities

For sodium-dependent glucose transport assay, cells expressing hSGLT2 were seeded into a 96-well culture plate at a density of $5 \times 10^4$ cells/well in RPMI medium 1640 containing 10% fetal bovine serum. The cells were used 1 day after plating. They were incubated in pretreatment buffer (10 mM HEPES, 5 mM Tris, 140 mM choline chloride, 2 mM KCl, 1 mM CaCl$_2$, and 1 mM MgCl$_2$, pH 7.4) at 37° C. for 10 min. They were then incubated in uptake buffer (10 mM HEPES, 5 mM Tris, 140 mM NaCl, 2 mM KCl, 1 mM CaCl$_2$, 1 mM MgCl$_2$, and 1 mM $^{14}$C-nonlabeled AMG pH 7.4) containing $^{14}$C-labeled (8 μM) and inhibitor or DMSO vehicle at 37° C. for 2 h. Cells were washed twice with washing buffer (pretreatment buffer containing 10 mM AMG at room temperature) and then the radioactivity was measured using a liquid scintillation counter. IC$_{50}$ was determined by nonlinear regression analysis using GraphPad PRISM [Katsuno, K. et al. *J. Pharmacol. Exp. Ther.* 2007, 320, 323-330; Han, S. et al. *Deabetes*, 2008, 57, 1723-1729].

TABLE 1

| | hSGLT2 Inhibitory Activity | | |
| --- | --- | --- | --- |
| Example | Structure | Name | IC$_{50}$ (nM) |
| 1 | | (2R,3R,4S,5S,6R)-2-(5-chloro-4-(4-ethoxybenzyl)thiophen-2-yl)-6-(hydroxymethyl)-tetrahydro-2H-pyran-3,4,5-triol | 34.6 |
| 2 | | (2R,3R,4S,5S,6R)-2-(5-chloro-4-(4-methoxybenzyl)thiophen-2-yl)-6-(hydroxymethyl)-tetrahydro-2H-pyran-3,4,5-triol | 86.5 |
| 3 | | (2R,3R,4S,5S,6R)-2-(5-chloro-4-((5-(4-fluorophenyl)thiophen-2-yl)methyl)thiophen-2-yl)-6-(hydroxymethyl)-tetrahydro-2H-pyran-3,4,5-triol | 91.3 |

TABLE 1-continued hSGLT2 Inhibitory Activity

| Example | Structure | Name | IC$_{50}$ (nM) |
|---|---|---|---|
| 4 | 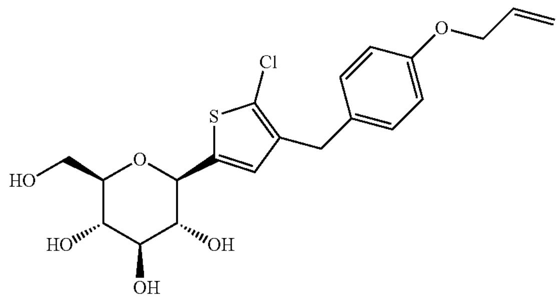 [SMILES: C=CCOc1ccc(Cc2cc([C@@H]3O[C@H](CO)[C@@H](O)[C@H](O)[C@H]3O)sc2Cl)cc1] | (2R,3R,4S,5S,6R)-2-(4-(4-(allyloxy)benzyl)-5-chlorothiophen-2-yl)-6-(hydroxymethyl)-tetrahydro-2H-pyran-3,4,5-triol | 54.6 |
| 5 | 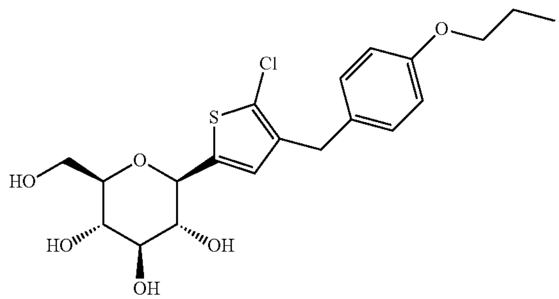 [SMILES: CCCOc1ccc(Cc2cc([C@@H]3O[C@H](CO)[C@@H](O)[C@H](O)[C@H]3O)sc2Cl)cc1] | (2R,3R,4S,5S,6R)-2-(5-chloro-4-(4-propoxybenzyl)thiophen-2-yl)-6-(hydroxymethyl)-tetrahydro-2H-pyran-3,4,5-triol | 65.0 |
| 6 | 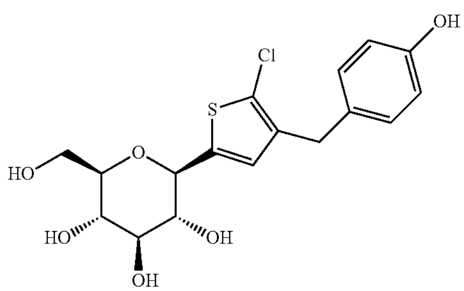 [SMILES: OC[C@H]1O[C@@H](c2cc(Cc3ccc(O)cc3)c(Cl)s2)[C@H](O)[C@@H](O)[C@@H]1O] | (2R,3R,4S,5S,6R)-2-(5-chloro-4-(4-hydroxybenzyl)thiophen-2-yl)-6-(hydroxymethyl)-tetrahydro-2H-pyran-3,4,5-triol | 140 |
| 7 | 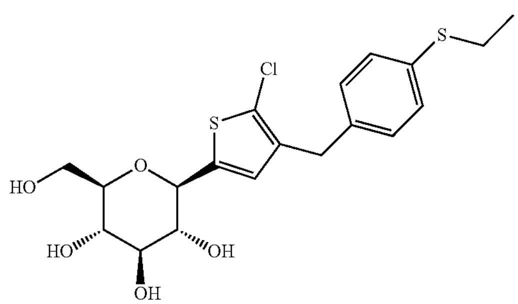 | (2R,3R,4S,5S,6R)-2-(5-chloro-4-(4-(ethylthio)benzyl)thiophen-2-yl)-6-(hydroxymethyl)-tetrahydro-2H-pyran-3,4,5-triol | 48.4 |
| 8 | 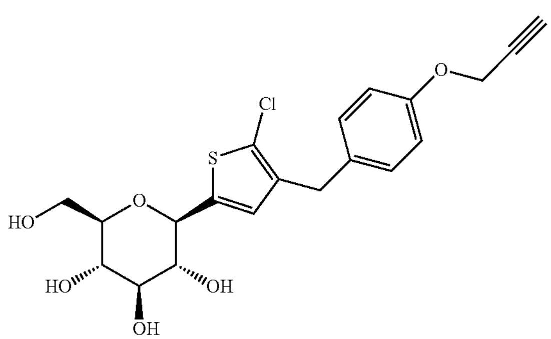 [SMILES: C#CCOc1ccc(Cc2cc([C@@H]3O[C@H](CO)[C@@H](O)[C@H](O)[C@H]3O)sc2Cl)cc1] | (2R,3R,4S,5S,6R)-2-(5-chloro-4-(4-(prop-2-ynyloxy)benzyl)thiophen-2-yl)-6-(hydroxymethyl)tetrahydro-2H-pyran-3,4,5-triol | 111 |

TABLE 1-continued hSGLT2 Inhibitory Activity

| Example | Structure | Name | IC$_{50}$ (nM) |
|---|---|---|---|
| 9 | 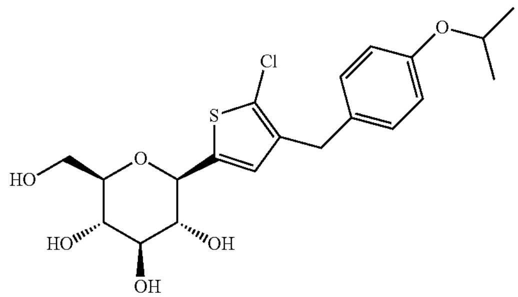 [SMILES: CC(C)Oc1ccc(Cc2cc([C@@H]3O[C@H](CO)[C@@H](O)[C@H](O)[C@H]3O)sc2Cl)cc1] | (2R,3R,4S,5S,6R)-2-(5-chloro-4-(4-isopropoxybenzyl)thiophen-2-yl)-6-(hydroxymethyl)-tetrahydro-2H-pyran-3,4,5-triol | 11.9 |
| 10 | 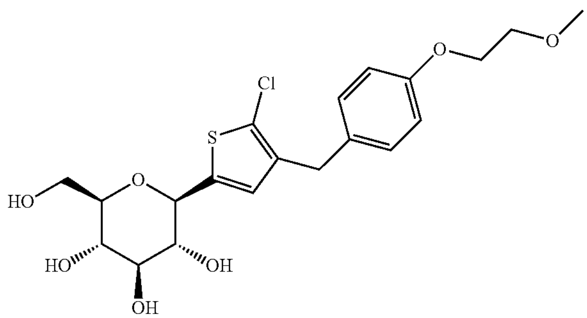 [SMILES: COCCOc1ccc(Cc2cc([C@@H]3O[C@H](CO)[C@@H](O)[C@H](O)[C@H]3O)sc2Cl)cc1] | (2R,3R,4S,5S,6R)-2-(5-chloro-4-(4-(2-methoxyethoxy)benzyl)thiophen-2-yl)-6-(hydroxymethyl)-tetrahydro-2H-pyran-3,4,5-triol | 115 |
| 11 | 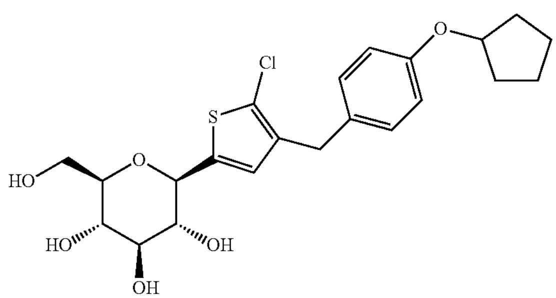 [SMILES: OC[C@H]1O[C@@H](c2cc(Cc3ccc(OC4CCCC4)cc3)c(Cl)s2)[C@H](O)[C@@H](O)[C@@H]1O] | (2R,3R,4S,5S,6R)-2-(5-chloro-4-(4-(cyclopentyloxy)benzyl)thiophen-2-yl)-6-(hydroxymethyl)-tetrahydro-2H-pyran-3,4,5-triol | 57.2 |
| 12 | 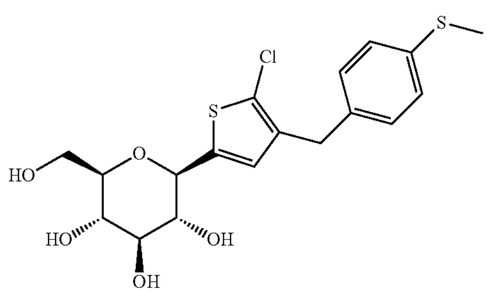 | (2R,3R,4S,5S,6R)-2-(5-chloro-4-(4-(methylthio)benzyl)thiophen-2-yl)-6-(hydroxymethyl)-tetrahydro-2H-pyran-3,4,5-triol | 12.8 |
| 13 | 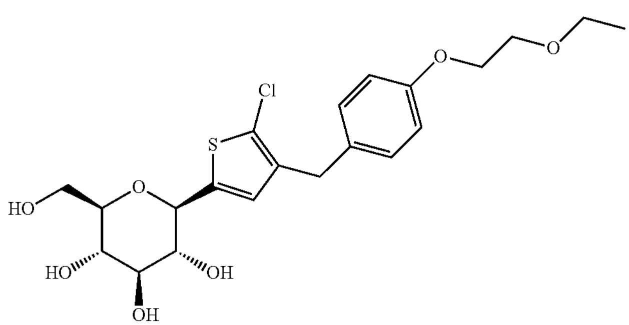 [SMILES: CCOCCOc1ccc(Cc2cc([C@@H]3O[C@H](CO)[C@@H](O)[C@H](O)[C@H]3O)sc2Cl)cc1] | (2R,3R,4S,5S,6R)-2-(5-chloro-4-(4-(2-ethoxyethoxy)benzyl)thiophen-2-yl)-6-(hydroxymethyl)-tetrahydro-2H-pyran-3,4,5-triol | 70.7 |

TABLE 1-continued hSGLT2 Inhibitory Activity

| Example | Structure | Name | IC$_{50}$ (nM) |
|---|---|---|---|
| 14 | 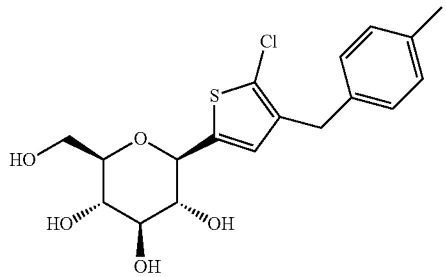 [SMILES: Cc1ccc(Cc2cc([C@@H]3O[C@H](CO)[C@@H](O)[C@H](O)[C@H]3O)sc2Cl)cc1] | (2R,3R,4S,5S,6R)-2-(5-chloro-4-(4-methylbenzyl)thiophen-2-yl)-6-(hydroxymethyl)-tetrahydro-2H-pyran-3,4,5-triol | 60.2 |
| 15 | 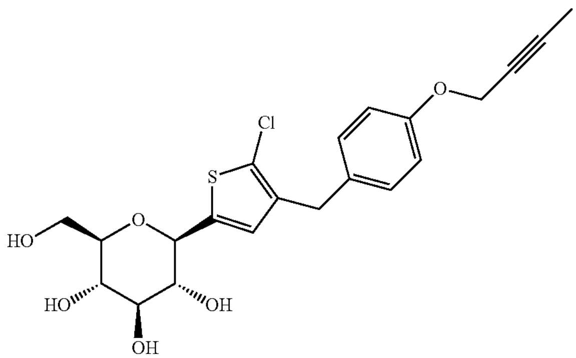 [SMILES: CC#CCOc1ccc(Cc2cc([C@@H]3O[C@H](CO)[C@@H](O)[C@H](O)[C@H]3O)sc2Cl)cc1] | (2R,3R,4S,5S,6R)-2-(4-(4-(but-2-ynyloxy)benzyl)-5-chlorothiophen-2-yl)-6-(hydroxymethyl)-tetrahydro-2H-pyran-3,4,5-triol | 94.0 |
| 16 | 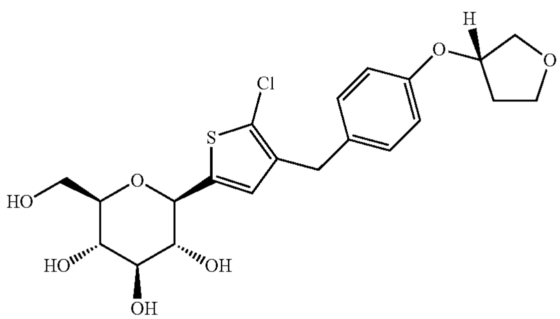 [SMILES: OC[C@H]1O[C@@H](c2cc(Cc3ccc(O[C@H]4CCOC4)cc3)c(Cl)s2)[C@H](O)[C@@H](O)[C@@H]1O] | (2R,3R,4S,5S,6R)-2-(5-chloro-4-(4-(tetrahydrofuran-3-yloxy)benzyl)thiophen-2-yl)-6-(hydroxymethyl)-tetrahydro-2H-pyran-3,4,5-triol | 162 |
| 17 | 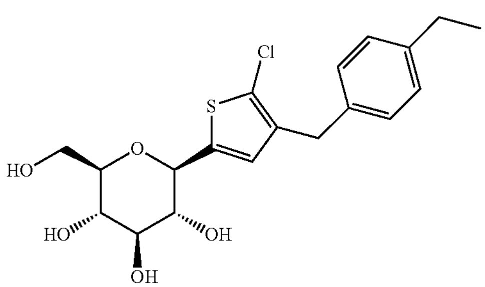 [SMILES: CCc1ccc(Cc2cc([C@@H]3O[C@H](CO)[C@@H](O)[C@H](O)[C@H]3O)sc2Cl)cc1] | (2R,3R,4S,5S,6R)-2-(5-chloro-4-(4-ethylbenzyl)thiophen-2-yl)-6-(hydroxymethyl)-tetrahydro-2H-pyran-3,4,5-triol | 4.47 |
| 18 | 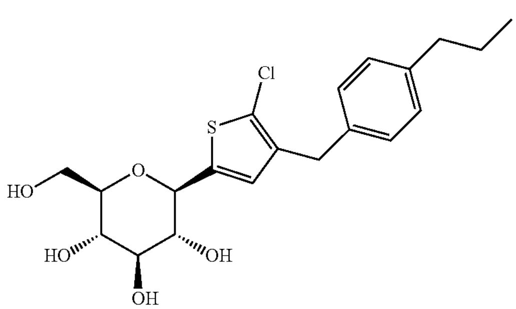 [SMILES: CCCc1ccc(Cc2cc([C@@H]3O[C@H](CO)[C@@H](O)[C@H](O)[C@H]3O)sc2Cl)cc1] | (2R,3R,4S,5S,6R)-2-(5-chloro-4-(4-propylbenzyl)thiophen-2-yl)-6-(hydroxymethyl)-tetrahydro-2H-pyran-3,4,5-triol | 10.3 |

TABLE 1-continued hSGLT2 Inhibitory Activity

| Example | Structure | Name | IC$_{50}$ (nM) |
|---|---|---|---|
| 19 | 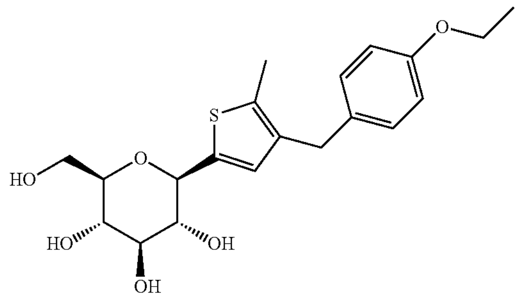 [SMILES: CCOc1ccc(Cc2cc([C@@H]3O[C@H](CO)[C@@H](O)[C@H](O)[C@H]3O)sc2C)cc1] | (2R,3R,4S,5S,6R)-2-(4-(4-ethoxybenzyl)-5-methylthiophen-2-yl)-6-(hydroxymethyl)-tetrahydro-2H-pyran-3,4,5-triol | 8.73 |
| 20 | 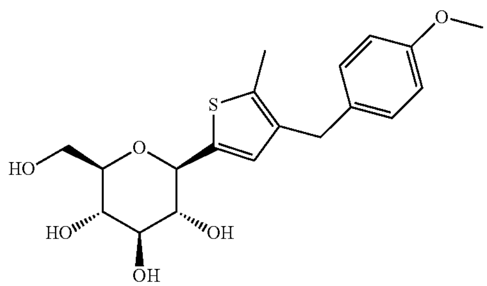 [SMILES: COc1ccc(Cc2cc([C@@H]3O[C@H](CO)[C@@H](O)[C@H](O)[C@H]3O)sc2C)cc1] | (2R,3S,4S,5R,6R)-2-(hydroxymethyl)-6-(4-(4-methoxybenzyl)-5-methylthiophen-2-yl)-tetrahydro-2H-pyran-3,4,5-triol | 11.5 |
| 21 | 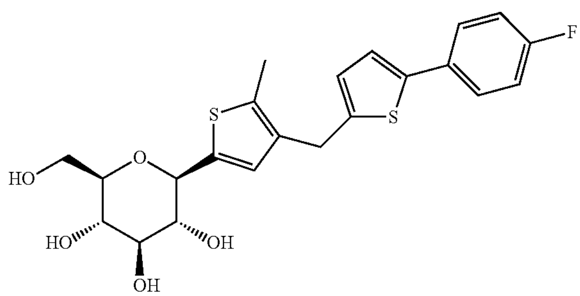 [SMILES: Cc1sc([C@@H]2O[C@H](CO)[C@@H](O)[C@H](O)[C@H]2O)cc1Cc1ccc(-c2ccc(F)cc2)s1] | (2R,3R,4S,5S,6R)-2-(4-((5-(4-fluorophenyl)thiophen-2-yl)methyl)-5-methylthiophen-2-yl)-6-(hydroxymethyl)-tetrahydro-2H-pyran-3,4,5-triol | 21.1 |
| 22 | 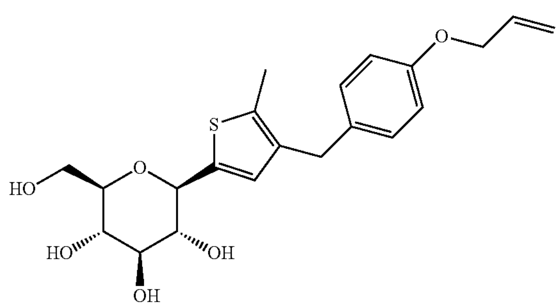 [SMILES: C=CCOc1ccc(Cc2cc([C@@H]3O[C@H](CO)[C@@H](O)[C@H](O)[C@H]3O)sc2C)cc1] | (2R,3R,4S,5S,6R)-2-(4-(4-(allyloxy)benzyl)-5-methylthiophen-2-yl)-6-(hydroxymethyl)-tetrahydro-2H-pyran-3,4,5-triol | 27.5 |
| 23 | 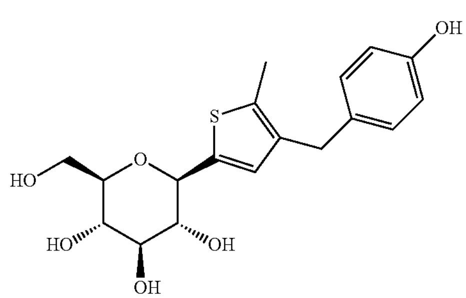 [SMILES: Cc1sc([C@@H]2O[C@H](CO)[C@@H](O)[C@H](O)[C@H]2O)cc1Cc1ccc(O)cc1] | (2R,3R,4S,5S,6R)-2-(4-(4-hydroxybenzyl)-5-methylthiophen-2-yl)-6-(hydroxymethyl)-tetrahydro-2H-pyran-3,4,5-triol | 50.2 |

TABLE 1-continued hSGLT2 Inhibitory Activity

| Example | Structure | Name | IC$_{50}$ (nM) |
|---|---|---|---|
| 24 | 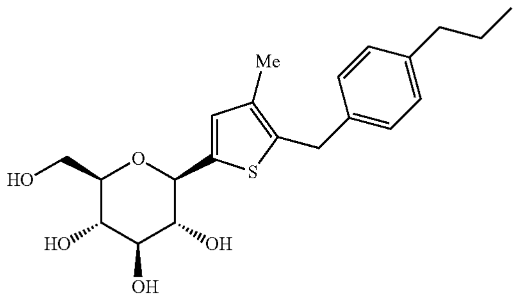 | (2R,3S,4S,5R,6R)-2-(hydroxymethyl)-6-(4-methyl-5-(4-propylbenzyl)thiophen-2-yl)tetrahydro-2H-pyran-3,4,5-triol | 59.8 |
| 25 | 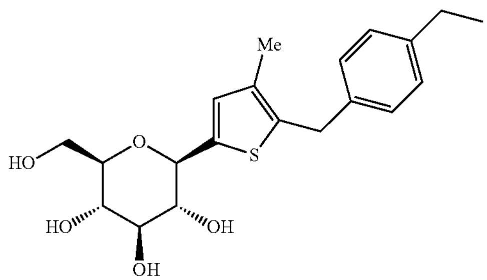 [SMILES: CCc1ccc(Cc2sc([C@@H]3O[C@H](CO)[C@@H](O)[C@H](O)[C@H]3O)cc2C)cc1] | (2R,3R,4S,5S,6R)-2-(5-(4-ethylbenzyl)-4-methylthiophen-2-yl)-6-(hydroxymethyl)tetrahydro-2H-pyran-3,4,5-triol | 24.8 |
| 26 | 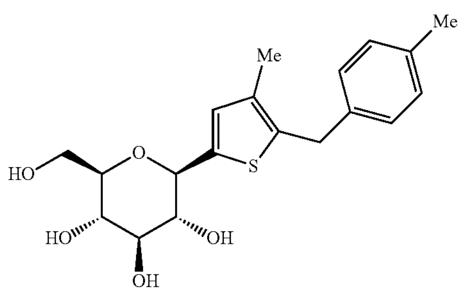 [SMILES: Cc1ccc(Cc2sc([C@@H]3O[C@H](CO)[C@@H](O)[C@H](O)[C@H]3O)cc2C)cc1] | (2R,3S,4S,5R,6R)-2-(hydroxymethyl)-6-(4-methyl-5-(4-methylbenzyl)thiophen-2-yl)tetrahydro-2H-pyran-3,4,5-triol | 69.6 |
| 27 | 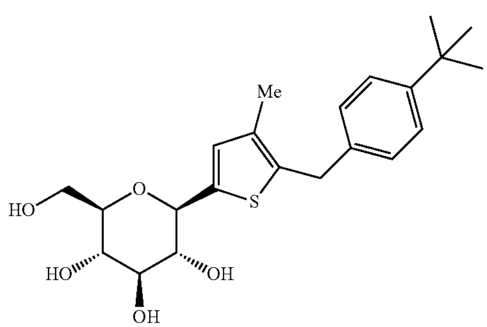 [SMILES: Cc1cc([C@@H]2O[C@H](CO)[C@@H](O)[C@H](O)[C@H]2O)sc1Cc1ccc(C(C)(C)C)cc1] | (2R,3R,4S,5S,6R)-2-(5-(4-tert-butylbenzyl)-4-methylthiophen-2-yl)-6-(hydroxymethyl)tetrahydro-2H-pyran-3,4,5-triol | 88.3 |
| 28 | 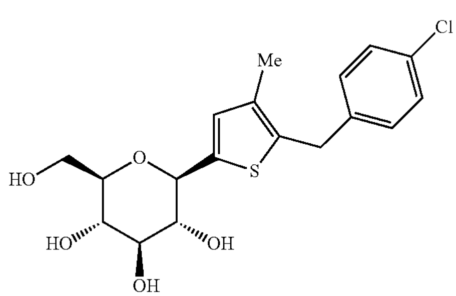 [SMILES: Cc1cc([C@@H]2O[C@H](CO)[C@@H](O)[C@H](O)[C@H]2O)sc1Cc1ccc(Cl)cc1] | (2R,3R,4S,5S,6R)-2-(5-(4-chlorobenzyl)-4-methylthiophen-2-yl)-6-(hydroxymethyl)tetrahydro-2H-pyran-3,4,5-triol | 451 |

TABLE 1-continued hSGLT2 Inhibitory Activity

| Example | Structure | Name | IC$_{50}$ (nM) |
|---|---|---|---|
| 29 | 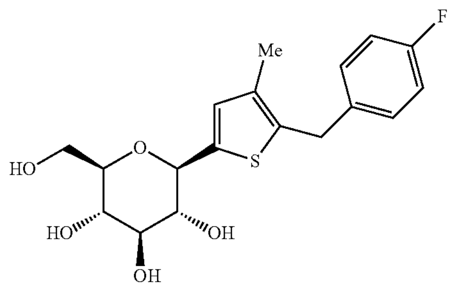 [SMILES: Cc1cc([C@@H]2O[C@H](CO)[C@@H](O)[C@H](O)[C@H]2O)sc1Cc1ccc(F)cc1] | (2R,3R,4S,5S,6R)-2-(5-(4-fluorobenzyl)-4-methylthiophen-2-yl)-6-(hydroxymethyl)tetrahydro-2H-pyran-3,4,5-triol | >10,000 |
| 30 | 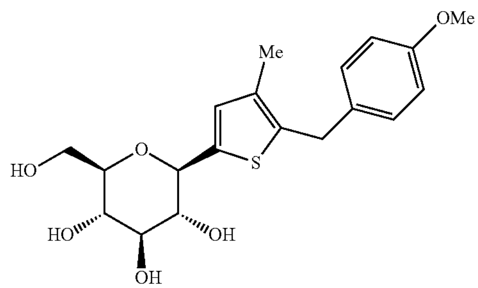 [SMILES: COc1ccc(Cc2sc([C@@H]3O[C@H](CO)[C@@H](O)[C@H](O)[C@H]3O)cc2C)cc1] | (2R,3S,4S,5R,6R)-2-(hydroxymethyl)-6-(5-(4-methoxybenzyl)-4-methylthiophen-2-yl)tetrahydro-2H-pyran-3,4,5-triol | 68.9 |
| 31 | 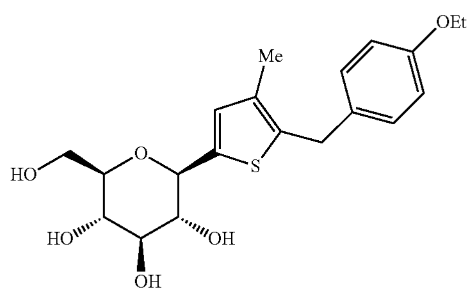 [SMILES: CCOc1ccc(Cc2sc([C@@H]3O[C@H](CO)[C@@H](O)[C@H](O)[C@H]3O)cc2C)cc1] | (2R,3R,4S,5S,6R)-2-(5-(4-ethoxybenzyl)-4-methylthiophen-2-yl)-6-(hydroxymethyl)tetrahydro-2H-pyran-3,4,5-triol | 71.4 |
| 32 | 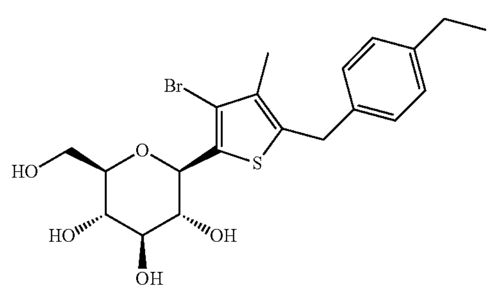 [SMILES: CCc1ccc(Cc2sc([C@@H]3O[C@H](CO)[C@@H](O)[C@H](O)[C@H]3O)c(Br)c2C)cc1] | (2R,3R,4S,5S,6R)-2-(3-bromo-5-(4-ethylbenzyl)-4-methylthiophen-2-yl)-6-(hydroxymethyl)tetrahydro-2H-pyran-3,4,5-triol | 12.4 |
| 33 | 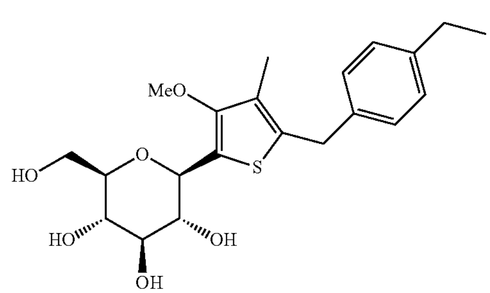 [SMILES: CCc1ccc(Cc2sc([C@@H]3O[C@H](CO)[C@@H](O)[C@H](O)[C@H]3O)c(OC)c2C)cc1] | (2R,3R,4S,5S,6R)-2-(5-(4-ethylbenzyl)-3-methoxy-4-methylthiophen-2-yl)-6-(hydroxymethyl)tetrahydro-2H-pyran-3,4,5-triol | 49.5 |

TABLE 1-continued hSGLT2 Inhibitory Activity

| Example | Structure | Name | IC$_{50}$ (nM) |
|---|---|---|---|
| 34 | 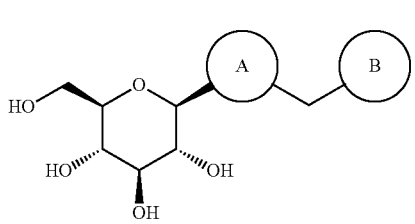 | (2R,3R,4S,5S,6R)-2-(5-(4-ethylbenzyl)-3,4-dimethylthiophen-2-yl)-6-(hydroxymethyl)tetrahydro-2H-pyran-3,4,5-triol | 29.3 |

*Reference compound dapagliflozin IC$_{50}$ = 1.27 ± 0.04 nM (in-house assay).
**These data were obtained by single determinations.

As shown in Table 1, the inventive compounds exhibit an inhibitory activity against sodium-dependent glucose cotransporter 2 (SGLT2) and are effective as SGLT2 inhibitors.

While the invention has been described with respect to the above specific embodiments, it should be recognized that various modifications and changes may be made to the invention by those skilled in the art which also fall within the scope of the invention as defined by the appended claims.

What is claimed is:

1. A compound of formula (I), or a pharmaceutically acceptable salt, carboxylate, or aminoacetate thereof:

(I)

wherein,
ring A is thiophene; and
ring B is benzene, 5 to 10-membered heterocycloalkyl, or 5 to 13-membered heteroaryl,
in which said ring A is substituted with at least one substituent selected from the group consisting of hydroxy, mercapto, cyano, carboxy, nitro, guanidino, ureido, amino, $C_{1-7}$ alkyl, $C_{2-7}$ alkenyl, $C_{2-7}$ alkynyl, $C_{1-7}$ alkoxy-$C_{1-7}$ alkyl, $C_{1-7}$alkoxy, $C_{1-7}$alkoxy-$C_{1-7}$ alkoxy, $C_{2-7}$ alkenyloxy, $C_{2-7}$ alkynyloxy, 5 to 10-membered heterocycloalkyloxy, $C_{3-10}$ cycloalkyl, $C_{5-10}$ cycloalkenyl, $C_{3-10}$ cycloalkyloxy, phenyl-$C_{1-7}$ alkoxy, mono- or di-$C_{1-7}$ alkylamino, aminocarbonyl, $C_{2-8}$ acylamino, $C_{2-8}$ acyl, $C_{1-7}$ alkoxycarbonyl, mono- or di-$C_{1-7}$ alkylcarbamoyl, $C_{1-7}$alkylsulfonylamino, phenylsulfonylamino, $C_{1-7}$ alkylsulfanyl, $C_{1-7}$alkylsulfinyl, $C_{1-7}$alkylsulfonyl, $C_{6-14}$ arylsulfanyl, $C_{6-14}$ alkylsulfonyl, $C_{6-14}$ aryl, $C_{7-15}$ aroyl, 5 to 13-membered heteroaryl, 6 to 14-membered heteroaroyl, $C_{7-15}$ aroyloxy, $C_{2-8}$ acyloxy, 6 to 14-membered heteroaroyloxy, and 5 to 10-membered heterocycloalkyl,
in which said ring B is substituted with at least one substituent selected from the group consisting of halogen, hydroxy, mercapto, cyano, carboxy, nitro, guanidino, ureido, amino, $C_{1-7}$alkyl, $C_{2-7}$ alkenyl, $C_{2-7}$ alkynyl, $C_{1-7}$ alkoxy-$C_{1-7}$ alkyl, $C_{1-7}$ alkoxy, $C_{1-7}$ alkoxy-$C_{1-7}$ alkoxy, $C_{2-7}$ alkenyloxy, $C_{2-7}$ alkynyloxy, 5 to 10-membered heterocycloalkyloxy, $C_{3-10}$ cycloalkyl, $C_{5-10}$ cycloalkenyl, $C_{3-10}$ cycloalkyloxy, phenyl-$C_{1-7}$ alkoxy, mono- or di-$C_{1-7}$ alkylamino, aminocarbonyl, $C_{2-8}$ acylamino, $C_{2-8}$ acyl, $C_{1-7}$ alkoxycarbonyl, mono- or di-$C_{1-7}$ alkylcarbamoyl, $C_{1-7}$ alkylsulfonylamino, phenylsulfonylamino, $C_{1-7}$ alkylsulfanyl, $C_{1-7}$ alkylsulfinyl, $C_{1-7}$ alkylsulfonyl, $C_{6-14}$ arylsulfanyl, $C_{6-14}$ arylsulfonyl, $C_{6-14}$ aryl, $C_{7-15}$ aroyl, 5 to 13-membered heteroaryl, 6 to 14-membered heteroaroyl, $C_{7-15}$ aroyloxy, $C_{2-8}$ acyloxy, 6 to 14-membered heteroaroyloxy, and 5 to 10-membered heterocycloalkyl,
in which
said alkyl, alkenyl, alkynyl, alkoxy, or acyl is optionally substituted with a substituent selected from the group consisting of halogen, hydroxy, cyano, nitro, amino, and mercapto;
said cycloalkyl, cycloalkenyl, aryl, aroyl, heteroaryl, heteroaroyl, or heterocycloalkyl is optionally substituted with a substituent selected from the group consisting of halogen, hydroxy, cyano, nitro, amino, mercapto, $C_{1-4}$ alkyl, and $C_{1-4}$ alkoxy; and
said heterocycloalkyl, heteroaryl, and heteroaroyl each independently contains at least one heteroatom selected from the group consisting of N, O and S.

2. The compound according to claim 1, wherein
the ring B is thiophene, oxazole, thiazole, oxadiazole, or thiadiazaole,
in which said ring B is substituted with at least one substituent selected from the group consisting of halogen, hydroxy, mercapto, cyano, carboxy, amino, mono- or di-$C_{1-7}$ alkylamino, guanidino, ureido, $C_{1-7}$alkoxy, $C_{1-7}$ alkoxy-$C_{1-7}$ alkoxy, $C_{2-7}$ alkenyloxy, $C_{2-7}$ alkynyloxy, $C_{3}$-$_{10}$cycloalkyloxy, 5 to 10-membered heterocycloalkyloxy, $C_{1-7}$alkylsulfanyl, $C_{6-14}$ arylsulfanyl, $C_{1-7}$ alkyl, $C_{2-7}$ alkenyl, $C_{2-7}$ alkynyl, $C_{3-10}$ cycloalkyl, $C_{5-10}$ cycloalkenyl, $C_{6-14}$ aryl, 5 to 13-membered heteroaryl, $C_{2-8}$ acyl, $C_{2-8}$ acyloxy, 6 to 14-membered heteroaroyloxy, $C_{7-15}$ aroyl, $C_{7-15}$ aroyloxy, and 5 to 10-membered heterocycloalkyl,
in which
said alkyl, alkenyl, alkynyl, alkoxy, or acyl is optionally substituted with a substituent selected from the group consisting of halogen, hydroxy, cyano, nitro, amino, and mercapto;

said cycloalkyl, cycloalkenyl, aryl, aroyl, heteroaryl, heteroaroyl, or heterocycloalkyl is optionally substituted with a substituent selected from the group consisting of halogen, hydroxy, cyano, nitro, amino, mercapto, $C_{1-4}$ alkyl, and $C_{1-4}$ alkoxy; and said heterocycloalkyl, heteroaryl, and heteroaroyl each independently contains at least one heteroatom selected from the group consising of N, O and S.

3. The compound according to claim 1, wherein the ring A is

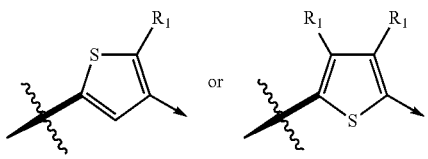

wherein $R_1$ is hydroxy, mercapto, cyano, carboxy, nitro, guanidino, ureido, amino, $C_{1-7}$alkyl, $C_{2-7}$ alkenyl, $C_{2-7}$ alkynyl, hydroxyalkyl, $C_{1-7}$alkoxy-$C_{1-7}$ alkyl, $C_{1-7}$alkoxy, $C_{3-10}$ cycloalkyl, $C_{5-10}$ cycloalkenyl, $C_{3-10}$ cycloalkyloxy, phenyl-$C_{1-7}$ alkoxy, mono- or di-$C_{1-7}$ alkylamino, aminocarbonyl, $C_{2-8}$ acylamino, $C_{2-8}$ acyl, $C_{1-7}$alkoxycarbonyl, mono- or di-$C_{1-7}$alkylcarbamoyl, $C_{1-7}$alkylsulfonylamino, phenylsulfonylamino, $C_{1-7}$alkylsulfanyl, $C_{1-7}$alkylsulfinyl, $C_{1-7}$alkylsulfonyl, phenylsulfonyl, $C_{6-14}$ aryl, $C_{7-15}$ aroyl, 5 to 13-membered heteroaryl, 6 to 14-membered heteroaroyl, $C_{7-15}$ aroyloxy, $C_{2-8}$ acyloxy, 6 to 14-membered heteroaroyloxy, or 5 to 10-membered heterocycloalkyl; and the ring B is

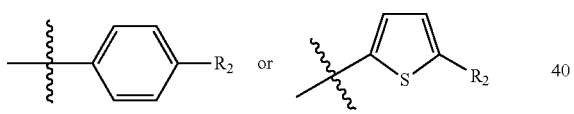

wherein $R_2$ is halogen, hydroxy, mercapto, cyano, carboxy, amino, mono- or di-$C_{1-7}$ alkylamino, guanidino, ureido, $C_{1-7}$alkoxy, $C_{1-7}$alkoxy-$C_{1-7}$ alkoxy, $C_{2-7}$ alkenyloxy, $C_{2-7}$alkynyloxy, $C_{3-10}$ cycloalkyloxy, 5 to 10-membered heterocycloalkyloxy, $C_{1-7}$alkylsulfanyl, $C_{6-14}$arylsulfanyl, $C_{1-7}$alkyl, $C_{2-7}$ alkenyl, $C_{2-7}$ alkynyl, $C_{3-10}$ cycloalkyl, $C_{5-10}$ cycloalkenyl, $C_{6-14}$ aryl, 5 to 13-membered heteroaryl, $C_{2-8}$ acyl, $C_{2-8}$ acyloxy, 6 to 14-membered heteroaroyloxy, $C_{7-15}$ aroyl, $C_{7-15}$aroyloxy, or 5 to 10-membered heterocycloalkyl, in which said alkyl, alkenyl, alkynyl, alkoxy, or acyl is optionally substituted with a substituent selected from the group consisting of halogen, hydroxy, cyano, nitro, amino, and mercapto;

said cycloalkyl, cycloalkenyl, aryl, aroyl, heteroaryl, heteroaroyl, or heterocycloalkyl is optionally substituted with a substituent selected from the group consisting of halogen, hydroxy, cyano, nitro, amino, mercapto, $C_{1-4}$ alkyl, and $C_{1-4}$ alkoxy; and said heterocycloalkyl, heteroaryl, and heteroaroyl each independently contains at least one heteroatom selected from the group consisting of N, O and S.

4. The compound according to claim 3, wherein $R_1$ is $C_{1-7}$alkyl, or $C_{1-7}$alkoxy; and $R_2$ is halogen, hydroxy, $C_{1-7}$alkyl, $C_{1-7}$alkoxy, $C_{1-7}$alkoxy-$C_{1-7}$ alkoxy, $C_{2-7}$ alkenyloxy, $C_{2-7}$alkynyloxy, $C_{1-7}$ alkylsulfanyl, $C_{6-14}$ aryl, $C_{3-10}$ cycloalkyloxy, or 5 to 10-membered heterocycloalkyloxy, in which said alkyl or alkoxy is optionally substituted with a substituent selected from the group consisting of halogen, hydroxy, cyano, nitro, amino, and mercapto;

said aryl, cycloalkyl, or heterocycloalkyl is optionally substituted with a substituent selected from the group consisting of halogen, hydroxy, cyano, nitro, amino, mercapto, $C_{1-4}$ alkyl, and $C_{1-4}$alkoxy; and said heterocycloalkyl contains at least one heteroatom selected from the group consisting of N, O and S.

5. The compound according to claim 1, wherein the ring A is

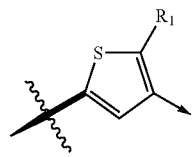

in which $R_1$ is $C_{1-7}$alkyl; or

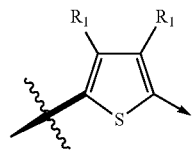

in which $R_1$ is $C_{1-7}$ alkyl, or $C_{1-7}$ alkoxy; and the ring B is

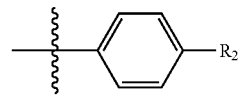

in which $R_2$ is hydroxy, halogen, $C_{1-7}$ alkyl, $C_{1-7}$alkoxy, $C_{1-7}$alkoxy-$C_{1-7}$ alkoxy, $C_{1-7}$alkenyloxy, $C_{1-7}$alkynyloxy, $C_{1-7}$alkylthio, $C_{3-7}$ cycloalkyloxy, or 5 to 7-membered heterocycloalkyloxy; or

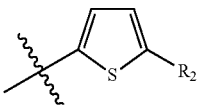

in which $R_2$ is $C_{6-14}$ aryl substituted or unsubstituted with halogen, in which said heterocycloalkyl contains at least one heteroatom selected from the group consisting of N, O and S.

6. A compound of Formula (I), or a pharmaceutically acceptable salt, carboxylate, or aminoacetate thereof:

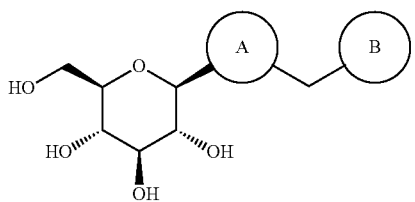

wherein
ring A is thiophene; and
ring B is benzene, 5 to 10-membered heterocycloalkyl, or 5 to 13-membered heteroaryl,
in which said ring A and ring B are each substituted with at least one substituent selected from the group consisting of halogen, hydroxy, mercapto, cyano, carboxy, nitro, guanidino, ureido, amino, $C_{1-7}$ alkyl, $C_{2-7}$ alkenyl, $C_{2-7}$ alkynyl, $C_{1-7}$ alkoxy-$C_{1-7}$ alkyl, $C_{1-7}$ alkoxy, $C_{1-7}$ alkoxy-$C_{1-7}$ alkoxy, $C_{2-7}$ alkenyloxy, $C_{2-7}$ alkynyloxy, 5 to 10-membered heterocycloalkyloxy, $C_{3-10}$ cycloalkyl, $C_{5-10}$ cycloalkenyl, $C_{3-10}$ cycloalkyloxy, phenyl-$C_{1-7}$ alkoxy, mono- or di-$C_{1-7}$ alkylamino, aminocarbonyl, $C_{2-8}$ acylamino, $C_{2-8}$ acyl, $C_{1-7}$ alkoxycarbonyl, mono- or di-$C_{1-7}$ alkylcarbamoyl, $C_{1-7}$ alkylsulfonylamino, phenylsulfonylamino, $C_{1-7}$ alkylsulfanyl, $C_{1-7}$ alkylsulfinyl, $C_{1-7}$ alkylsulfonyl, $C_{6-14}$ arylsulfanyl, $C_{6-14}$ arylsulfonyl, $C_{6-14}$ aryl, $C_{7-15}$ aroyl, 5 to 13-membered heteroaryl, 6 to 14-membered heteroaroyl, $C_{7-15}$ aroyloxy, $C_{2-8}$ acyloxy, 6 to 14-membered heteroaroyloxy, and 5 to 10-membered heterocycloalkyl,
in which
said alkyl, alkenyl, alkynyl, alkoxy, or acyl is optionally substituted with a substituent selected from the group consisting of halogen, hydroxy, cyano, nitro, amino, and mercapto;
said cycloalkyl, cycloalkenyl, aryl, aroyl, heteroaryl, heteroaroyl, or heterocycloalkyl is optionally substituted with a substituent selected from the group consisting of halogen, hydroxy, cyano, nitro, amino, mercapto, $C_{1-4}$ alkyl, and $C_{1-4}$ alkoxy; and
said heterocycloalkyl, heteroaryl, and heteroaroyl each independently contains at least one heteroatom selected from the group consisting of N, O and S,
wherein the compound of Formula (I) is selected from the group consisting of:
(1) (2R,3R,4S,5S,6R)-2-(5-chloro-4-(4-ethoxybenzyl)thiophen-2-yl)-6-(hydroxymethyl)-tetrahydro-2H-pyran-3,4,5-triol;
(2) (2R,3R,4S,5S,6R)-2-(5-chloro-4-(4-methoxybenzyl)thiophen-2-yl)-6-(hydroxymethyl)-tetrahydro-2H-pyran-3,4,5-triol;
(3) (2R,3R,4S,5S,6R)-2-(5-chloro-4-((5-(4-fluorophenyl)thiophen-2-yl)methyl)thiophen-2-yl)-6-(hydroxymethyl)-tetrahydro-2H-pyran-3,4,5-triol;
(4) (2R,3R,4S,5S,6R)-2-(4-(4-(allyloxy)benzyl)-5-chlorothiophen-2-yl)-6-(hydroxymethyl)-tetrahydro-2H-pyran-3,4,5-triol;
(5) (2R,3R,4S,5S,6R)-2-(5-chloro-4-(4-propoxybenzyl)thiophen-2-yl)-6-(hydroxymethyl)-tetrahydro-2H-pyran-3,4,5-triol;
(6) (2R,3R,4S,5S,6R)-2-(5-chloro-4-(4-hydroxybenzyl)thiophen-2-yl)-6-(hydroxymethyl)-tetrahydro-2H-pyran-3,4,5-triol;
(7) (2R,3R,4S,5S,6R)-2-(5-chloro-4-(4-(ethylthio)benzyl)thiophen-2-yl)-6-(hydroxymethyl)-tetrahydro-2H-pyran-3,4,5-triol;
(8) (2R,3R,4S,5S,6R)-2-(5-chloro-4-(4-(prop-2-ynyloxy)benzyl)thiophen-2-yl)-6-(hydroxymethyl)-tetrahydro-2H-pyran-3,4,5-triol;
(9) (2R,3R,4S,5S,6R)-2-(5-chloro-4-(4-isopropoxybenzyl)thiophen-2-yl)-6-(hydroxymethyl)-tetrahydro-2H-pyran-3,4,5-triol;
(10) (2R,3R,4S,5S,6R)-2-(5-chloro-4-(4-(2-methoxyethoxy)benzyl)thiophen-2-yl)-6-(hydroxymethyl)-tetrahydro-2H-pyran-3,4,5-triol;
(11) (2R,3R,4S,5S,6R)-2-(5-chloro-4-(4-(cyclopentyloxy)benzyl)thiophen-2-yl)-6-(hydroxymethyl)-tetrahydro-2H-pyran-3,4,5-triol;
(12) (2R,3R,4S,5S,6R)-2-(5-chloro-4-(4-(methylthio)benzyl)thiophen-2-yl)-6-(hydroxymethyl)-tetrahydro-2H-pyran-3,4,5-triol;
(13) (2R,3R,4S,5S,6R)-2-(5-chloro-4-(4-(2-ethoxyethoxy)benzyl)thiophen-2-yl)-6-(hydroxymethyl)-tetrahydro-2H-pyran-3,4,5-triol;
(14) (2R,3R,4S,5S,6R)-2-(5-chloro-4-(4-methylbenzyl)thiophen-2-yl)-6-(hydroxymethyl)-tetrahydro-2H-pyran-3,4,5-triol;
(15) (2R,3R,4S,5S,6R)-2-(4-(4-(but-2-ynyloxy)benzyl)-5-chlorothiophen-2-yl)-6-(hydroxymethyl)-tetrahydro-2H-pyran-3,4,5-triol;
(16) (2R,3R,4S,5S,6R)-2-(5-chloro-4-(4-(tetrahydrofuran-3-yloxy)benzyl)thiophen-2-yl)-6-(hydroxymethyl)-tetrahydro-2H-pyran-3,4,5-triol;
(18) (2R,3R,4S,5S,6R)-2-(5-chloro-4-(4-propylbenzyl)thiophen-2-yl)-6-(hydroxymethyl)-tetrahydro-2H-pyran-3,4,5-triol;
(19) (2R,3R,4S,5S,6R)-2-(4-(4-ethoxybenzyl)-5-methylthiophen-2-yl)-6-(hydroxymethyl)-tetrahydro-2H-pyran-3,4,5-triol;
(20) (2R,3S,4S,5R,6R)-2-(hydroxymethyl)-6-(4-(4-methoxybenzyl)-5-methylthiophen-2-y1)-tetrahydro-2H-pyran-3,4,5-triol;
(21) (2R,3R,4S,5S,6R)-2-((5-(4-fluorophenyl)thiophen-2-yl)methyl)-5-methylthiophen-2-yl)-6-(hydroxymethyl)-tetrahydro-2H-pyran-3,4,5-triol;
(22) (2R,3R,4S,5S,6R)-2-(4-(4-(allyloxy)benzyl)-5-methylthiophen-2-yl)-6-(hydroxymethyl)-tetrahydro-2H-pyran-3,4,5-triol;
(23) (2R,3R,4S,5S,6R)-2-(4-(4-hydroxybenzyl)-5-methylthiophen-2-yl)-6-(hydroxymethyl)-tetrahydro-2H-pyran-3,4,5-triol;
(24) (2R,3S,4S,5R,6R)-2-(hydroxymethyl)-6-(4-methyl-5-(4-propylbenzyl)thiophen-2-yl)tetrahydro-2H-pyran-3,4,5-triol;
(25) (2R,3R,4S,5S,6R)-2-(5-(4-ethylbenzyl)-4-methylthiophen-2-yl)-6-(hydroxymethyl)tetrahydro-2H-pyran-3,4,5-triol;
(26) (2R,3S,4S,5R,6R)-2-(hydroxymethyl)-6-(4-methyl-5-(4-methylbenzyl)thiophen-2-yl)-tetrahydro-2H-pyran-3,4,5-triol;
(27) (2R,3R,4S,5S,6R)-2-(5-(4-tert-butylbenzyl)-4-methylthiophen-2-yl)-6-(hydroxymethyl)tetrahydro-2H-pyran-3,4,5-triol;
(28) (2R,3R,4S,5S,6R)-2-(5-(4-chlorobenzyl)-4-methylthiophen-2-yl)-6-(hydroxymethyl)tetrahydro-2H-pyran-3,4,5-triol;

(29) (2R,3R,4S,5S,6R)-2-(5-(4-fluorobenzyl)-4-methylthiophen-2-yl)-6-(hydroxymethyl)tetrahydro-2H-pyran-3,4,5-triol;

(30) (2R,3S,4S,5R,6R)-2-(hydroxymethyl)-6-(5-(4-methoxybenzyl)-4-methylthiophen-2-yl)tetrahydro-2H-pyran-3,4,5-triol;

(31) (2R,3R,4S,5S,6R)-2-(5-(4-ethoxybenzyl)-4-methylthiophen-2-yl)-6-(hydroxymethyl)tetrahydro-2H-pyran-3,4,5-triol;

(32) (2R,3R,4S,5S,6R)-2-(3-bromo-5-(4-ethylbenzyl)-4-methylthiophen-2-yl)-6-(hydroxymethyl)tetrahydro-2H-pyran-3,4,5-triol;

(33) (2R,3R,4S,5S,6R)-2-(5-(4-ethylbenzyl)-3-methoxy-4-methylthiophen-2-yl)-6-(hydroxymethyl)tetrahydro-2H-pyran-3,4,5-triol; and

(34) (2R,3R,4S,5S,6R)-2-(5-(4-ethylbenzyl)-3,4-dimethylthiophen-2-yl)-6-(hydroxymethyl)tetrahydro-2H-pyran-3,4,5-triol.

7. A method for preparing the compound of formula (I) of claim 1, comprising
(a) reacting a compound of formula (III) with a compound of formula (IV), followed by reduction, to obtain a compound of formula (V); and
(b) reacting the compound of formula (V) with a compound of formula (II), followed by deprotection, to obtain the compound of formula (I) of claim 1:

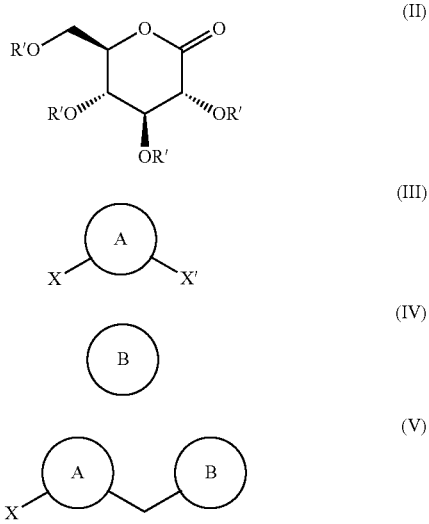

wherein R' is tetramethylsilane or benzyl; X is halogen; X' is —C(═O)X" or —CH$_2$X"; X" is hydroxy, halogen, or C$_{1-7}$alkoxy; and ring A and ring B have the same meanings as defined in claim 1.

8. A method for preparing the compound of formula (I) of claim 1, comprising
(a) reacting a compound of formula (III) with a compound of formula (II), followed by reduction, to obtain a compound of formula (VI); and
(b) reacting the compound of formula (VI) with a compound of formula (IV), followed by deprotection, to obtain the compound of formula (I) of claim 1:

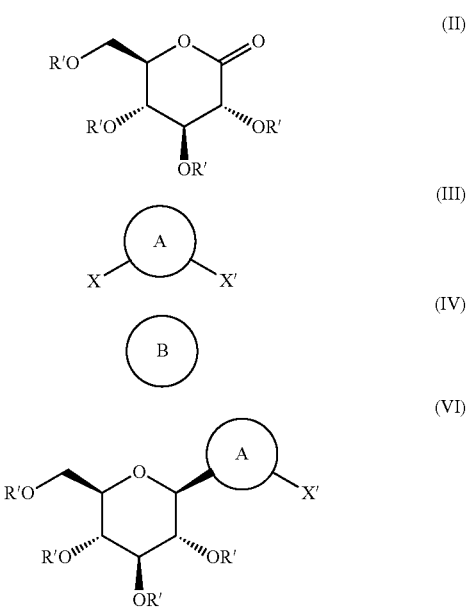

wherein R' is tetramethylsilane or benzyl; X is halogen; X' is —C(═O)X" or —CH$_2$X"; X" is hydroxy, halogen, or C$_{1-7}$alkoxy; and ring A and ring B are the same meanings as defined in claim 1.

9. A pharmaceutical composition comprising the compound of formula (I) of claim 1, or a pharmaceutically acceptable salt, carboxylate, or aminoacetate thereof, as an active ingredient, and a pharmaceutically acceptable carrier.

10. A method for treating a metabolic disorder in a mammal, which comprises administering the compound of formula (I) of claim 1 or a pharmaceutically acceptable salt, carboxylate, or aminoacetate thereof to the mammal, wherein the metabolic disorder is selected from the group consisting of diabetes, hyperglycemia, cardiovascular disease and hypertension.

11. A method for inhibiting sodium-dependent glucose cotransporter 2 (SGLT2) in a mammal, which comprises administering the compound of formula (I) of claim 1 or a pharmaceutically acceptable salt, carboxylate, or aminoacetate thereof to the mammal.

12. A method for preparing the compound of claim 6, comprising
(a) reacting a compound of formula (III) with a compound of formula (IV), followed by reduction, to obtain a compound of formula (V); and
(b) reacting the compound of formula (V) with a compound of formula (II), followed by deprotection, to obtain the compound of formula (I) of claim 6:

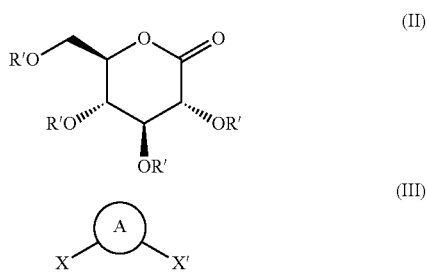

-continued

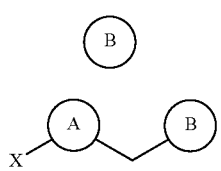
(IV)

(V)

wherein R' is tetramethylsilane or benzyl; X is halogen; X' is —C(=O)X" or —CH$_2$X"; X" is hydroxy, halogen, or C$_{1-7}$alkoxy; and ring A and ring B have the same meanings as defined in claim 6.

13. A method for preparing the compound of claim 6, comprising
    (a) reacting a compound of formula (III) with a compound of formula (II), followed by reduction, to obtain a compound of formula (VI); and
    (b) reacting the compound of formula (VI) with a compound of formula (IV), followed by deprotection, to obtain the compound of formula (I) of claim 6:

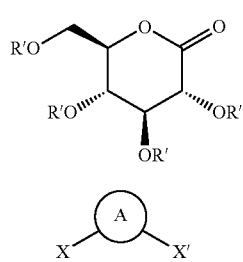
(II)

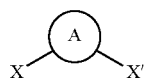
(III)

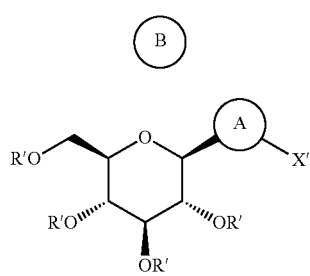
(IV)

(VI)

wherein R' is tetramethylsilane or benzyl; X is halogen; X' is —C(=O)X" or —CH$_2$X"; X" is hydroxy, halogen, or C$_{1-7}$alkoxy; and ring A and ring B are the same meanings as defined in claim 6.

14. A pharmaceutical composition comprising the compound of claim 6, or a pharmaceutically acceptable salt, carboxylate, or aminoacetate thereof, as an active ingredient, and a pharmaceutically acceptable carrier.

15. A method for treating a metabolic disorder in a mammal, which comprises administering the compound of claim 6 or a pharmaceutically acceptable salt, carboxylate, or aminoacetate thereof to the mammal, wherein the metabolic disorder is selected from the group consisting of diabetes, hyperglycemia, cardiovascular disease and hypertension.

16. A method for inhibiting sodium-dependent glucose cotransporter 2 in a mammal, which comprises administering the compound of claim 6 or a pharmaceutically acceptable salt, carboxylate, or aminoacetate thereof to the mammal.

\* \* \* \* \*